US010029011B2

(12) United States Patent
Hagendorf et al.

(10) Patent No.: US 10,029,011 B2
(45) Date of Patent: Jul. 24, 2018

(54) PHARMACEUTICAL COMPOSITION COMPRISING A GLP-1 AGONIST, AN INSULIN AND METHIONINE

(75) Inventors: Annika Hagendorf, Frankfurt am Main (DE); Gerrit Hauck, Frankfurt am Main (DE); Werner Mueller, Frankfurt am Main (DE); Isabell Schoettle, Frankfurt am Main (DE); Verena Siefke-Henzler, Frankfurt am Main (DE); Katrin Tertsch, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 13/509,542

(22) PCT Filed: Nov. 11, 2010

(86) PCT No.: PCT/EP2010/067250
§ 371 (c)(1),
(2), (4) Date: Aug. 2, 2012

(87) PCT Pub. No.: WO2011/058083
PCT Pub. Date: May 19, 2011

(65) Prior Publication Data
US 2012/0295846 A1  Nov. 22, 2012

(30) Foreign Application Priority Data

Nov. 13, 2009  (DE) .................. 10 2009 052 831
May 18, 2010  (DE) .................. 10 2010 020 902

(51) Int. Cl.
*A61K 38/28* (2006.01)
*A61P 5/50* (2006.01)
*C07K 14/62* (2006.01)
*A61K 33/30* (2006.01)
*A61K 38/00* (2006.01)
*A61P 3/08* (2006.01)
*A61P 3/10* (2006.01)
*A61K 38/26* (2006.01)
*A61P 7/12* (2006.01)
*C07K 14/605* (2006.01)
*A61K 47/10* (2017.01)
*A61K 9/00* (2006.01)
*A61K 47/18* (2017.01)

(52) U.S. Cl.
CPC ............ *A61K 47/10* (2013.01); *A61K 9/0019* (2013.01); *A61K 38/26* (2013.01); *A61K 38/28* (2013.01); *A61K 47/183* (2013.01); *C07K 14/605* (2013.01); *C07K 14/62* (2013.01)

(58) Field of Classification Search
None
See application file for complete search history.

(56) References Cited

U.S. PATENT DOCUMENTS

| | | |
|---|---|---|
| 3,758,683 A | 9/1973 | Jackson |
| 3,868,358 A | 2/1975 | Jackson |
| 3,984,696 A | 10/1976 | Collica et al. |
| 4,153,689 A | 5/1979 | Hirai et al. |
| 4,258,134 A | 3/1981 | Yoshida et al. |
| 4,367,737 A | 1/1983 | Kozam et al. |
| 4,608,364 A | 8/1986 | Grau |
| 4,614,730 A | 9/1986 | Hansen et al. |
| 4,644,057 A | 2/1987 | Bicker et al. |
| 4,689,042 A | 8/1987 | Sarnoff et al. |
| 4,701,440 A | 10/1987 | Grau |
| 4,731,405 A | 3/1988 | Kirsch et al. |
| 4,783,441 A | 11/1988 | Thurow |
| 4,839,341 A | 6/1989 | Massey et al. |
| 4,863,902 A | 9/1989 | Amagase et al. |
| 4,885,164 A | 12/1989 | Thurow |
| 4,923,162 A | 5/1990 | Fleming et al. |
| 4,959,351 A | 9/1990 | Grau |
| 4,960,702 A | 10/1990 | Rice et al. |
| 4,994,439 A | 2/1991 | Longenecker et al. |
| 5,006,718 A | 4/1991 | Lenhart |
| 5,008,241 A | 4/1991 | Markussen et al. |
| 5,034,415 A | 7/1991 | Rubin |
| 5,070,186 A | 12/1991 | Joergensen |
| 5,101,013 A | 3/1992 | Dorschug et al. |
| 5,177,058 A | 1/1993 | Dorschug |
| 5,187,177 A | 2/1993 | Garzaran |

(Continued)

FOREIGN PATENT DOCUMENTS

| | | |
|---|---|---|
| AU | 1986-62066 | 3/1987 |
| AU | 1987-75916 | 1/1988 |

(Continued)

OTHER PUBLICATIONS

Noble, et al., "Insulin Lispro: A Fast-Acting Insulin Analog," Am. Fam. Physician 57:279-286 (1998).*
Tews, D. et al., "Enhanced Protection against Cytokine- and Fatty Acid-induced Apoptosis in Pancreatic Beta Cells by Combined Treatment with Glucagon-like Peptide-1 Receptor Agonists and Insulin Analogues," Hormone and Metabolic Research (2008), vol. 40, No. 3, pp. 172-180.
Arnolds, Sabine et al., "Insulin Glargine (GLAR) plus Metformin (MET): An Efficacious and Safe Regimen That Can Be Combined with Exenatide (EXE) or Sitagliptin (SITA)," Diabetes, American Diabetes Association (2009), vol. 58, pp. A141.
International Search Report dated Mar. 23, 2011 issued in PCT/EP2010/067250.

(Continued)

*Primary Examiner* — Hasan Ahmed
*Assistant Examiner* — Thea D'Ambrosio
(74) *Attorney, Agent, or Firm* — McDonnell Boehnen Hulbert & Berghoff LLP

(57) ABSTRACT

A liquid composition comprising a GLP-1 agonist or/and a pharmacologically tolerable salt thereof, an insulin or/and a pharmacologically tolerable salt thereof, and, optionally, at least one pharmaceutically acceptable excipient, wherein the composition comprises methionine, as add-on therapy with metformin where appropriate.

9 Claims, 4 Drawing Sheets

(56) References Cited

U.S. PATENT DOCUMENTS

| | | | |
|---|---|---|---|
| 5,227,293 A | 7/1993 | Stengelin et al. | |
| 5,253,785 A | 10/1993 | Haber et al. | |
| 5,272,135 A * | 12/1993 | Takruri | 514/2.4 |
| 5,358,708 A | 10/1994 | Patel | |
| 5,358,857 A | 10/1994 | Stengelin et al. | |
| 5,370,629 A | 12/1994 | Michel et al. | |
| 5,397,771 A | 3/1995 | Bechgaard et al. | |
| 5,407,609 A | 4/1995 | Tice et al. | |
| 5,424,286 A | 6/1995 | Eng | |
| 5,428,006 A | 6/1995 | Bechgaard et al. | |
| 5,473,049 A | 12/1995 | Obermeier et al. | |
| 5,474,978 A | 12/1995 | Bakaysa et al. | |
| 5,478,323 A | 12/1995 | Westwood et al. | |
| 5,496,924 A | 3/1996 | Habermann et al. | |
| 5,506,203 A | 4/1996 | Backstrom et al. | |
| 5,509,905 A | 4/1996 | Michel et al. | |
| 5,514,646 A | 5/1996 | Chance et al. | |
| 5,524,286 A | 6/1996 | Chiesa et al. | |
| 5,534,488 A | 7/1996 | Hoffmann | |
| 5,545,618 A | 8/1996 | Buckley et al. | |
| 5,547,929 A | 8/1996 | Anderson, Jr. et al. | |
| 5,559,094 A | 9/1996 | Brems et al. | |
| 5,595,756 A | 1/1997 | Bally et al. | |
| 5,597,796 A | 1/1997 | Brange | |
| 5,614,219 A | 3/1997 | Wunderlich et al. | |
| 5,614,492 A | 3/1997 | Habener | |
| 5,631,224 A | 5/1997 | Efendic et al. | |
| 5,654,008 A | 8/1997 | Herbert et al. | |
| 5,656,722 A | 8/1997 | Dorschug | |
| 5,663,291 A | 9/1997 | Obermeier et al. | |
| 5,670,360 A | 9/1997 | Thorens | |
| 5,693,608 A | 12/1997 | Bechgaard et al. | |
| 5,700,662 A | 12/1997 | Chance et al. | |
| 5,707,641 A | 1/1998 | Gertner et al. | |
| 5,783,556 A | 7/1998 | Clark et al. | |
| 5,824,638 A | 10/1998 | Burnside et al. | |
| 5,846,747 A | 12/1998 | Thorens et al. | |
| 5,846,937 A | 12/1998 | Drucker | |
| 5,879,584 A | 3/1999 | Bianchetti et al. | |
| 5,948,751 A | 9/1999 | Kimer et al. | |
| 5,952,297 A | 9/1999 | DeFelippis et al. | |
| 5,981,964 A | 11/1999 | Mc Auley et al. | |
| 5,985,309 A | 11/1999 | Edwards et al. | |
| 5,986,048 A | 11/1999 | Rubroeder et al. | |
| 6,006,753 A | 12/1999 | Efendic | |
| 6,034,054 A | 3/2000 | DeFelippis et al. | |
| 6,043,214 A | 3/2000 | Jensen et al. | |
| 6,051,551 A | 4/2000 | Hughes et al. | |
| 6,051,689 A | 4/2000 | Thorens | |
| 6,100,376 A | 8/2000 | Dorschug | |
| 6,110,703 A | 8/2000 | Egel-Mitani et al. | |
| 6,174,856 B1 | 1/2001 | Langballe et al. | |
| 6,191,102 B1 | 2/2001 | DiMarchi et al. | |
| 6,197,926 B1 | 3/2001 | Gaur et al. | |
| 6,211,144 B1 | 4/2001 | Havelund | |
| 6,227,819 B1 | 5/2001 | Gettel et al. | |
| 6,248,363 B1 | 6/2001 | Patel et al. | |
| 6,267,981 B1 | 7/2001 | Okamoto et al. | |
| 6,268,335 B1 | 7/2001 | Brader | |
| 6,268,343 B1 | 7/2001 | Knudsen et al. | |
| 6,271,241 B1 | 8/2001 | DeSimone et al. | |
| 6,284,725 B1 | 9/2001 | Coolidge et al. | |
| 6,309,663 B1 | 10/2001 | Patel et al. | |
| 6,310,038 B1 | 10/2001 | Havelund | |
| 6,329,336 B1 | 12/2001 | Bridon et al. | |
| 6,335,316 B1 | 1/2002 | Hughes et al. | |
| 6,344,180 B1 | 2/2002 | Holst et al. | |
| 6,358,924 B1 | 3/2002 | Hoffmann | |
| 6,384,016 B1 | 5/2002 | Kaarsholm | |
| 6,388,053 B1 | 5/2002 | Galloway et al. | |
| 6,395,767 B2 | 5/2002 | Robl et al. | |
| 6,410,508 B1 | 6/2002 | Isales et al. | |
| 6,417,164 B1 | 7/2002 | Kolterman | |
| 6,444,641 B1 | 9/2002 | Flora | |
| 6,468,959 B1 | 10/2002 | Wunderlich et al. | |
| 6,489,292 B1 | 12/2002 | Havelund et al. | |
| 6,528,486 B1 | 3/2003 | Larsen et al. | |
| 6,734,162 B2 | 5/2004 | Van Antwerp et al. | |
| 6,767,887 B1 | 7/2004 | Hoffmann et al. | |
| 6,818,738 B2 | 11/2004 | Havelund | |
| 6,852,694 B2 | 2/2005 | Van Antwerp et al. | |
| 6,875,589 B2 | 4/2005 | Dorschug et al. | |
| 6,908,610 B1 | 6/2005 | Sato | |
| 6,908,897 B2 | 6/2005 | Brandenburg et al. | |
| 6,960,561 B2 | 11/2005 | Boderke | |
| 6,969,702 B2 | 11/2005 | Bertilsson et al. | |
| 7,022,674 B2 | 4/2006 | DeFelippis | |
| 7,115,563 B2 | 10/2006 | Younis | |
| 7,119,086 B2 | 10/2006 | Di Malta et al. | |
| 7,192,919 B2 | 3/2007 | Tzannis et al. | |
| 7,205,276 B2 | 4/2007 | Boderke | |
| 7,205,277 B2 | 4/2007 | Boderke | |
| 7,238,663 B2 | 7/2007 | DeFelippis et al. | |
| 7,405,196 B2 | 7/2008 | Rosskamp et al. | |
| 7,476,652 B2 | 1/2009 | Brunner-Schwarz et al. | |
| 7,544,656 B2 | 6/2009 | Sabetsky | |
| 7,544,657 B2 | 6/2009 | Ebbehoj et al. | |
| 7,576,050 B2 | 8/2009 | Greig et al. | |
| 7,713,930 B2 | 5/2010 | Brunner-Schwarz et al. | |
| 7,803,763 B2 | 9/2010 | Thurow et al. | |
| 7,807,242 B2 | 10/2010 | Soerensen et al. | |
| 7,918,833 B2 | 4/2011 | Veasey et al. | |
| 7,939,293 B2 | 5/2011 | Habermann et al. | |
| 7,977,310 B2 | 7/2011 | Rosskamp et al. | |
| 8,048,854 B2 * | 11/2011 | Habermann et al. | 514/6.3 |
| 8,084,420 B2 | 12/2011 | Steiner et al. | |
| 8,092,421 B2 | 1/2012 | Seiferlein et al. | |
| 8,092,422 B2 | 1/2012 | Seiferlein et al. | |
| 8,178,495 B2 | 5/2012 | Chilkoti | |
| 8,574,214 B2 | 11/2013 | Kuhn et al. | |
| 8,633,156 B2 | 1/2014 | Habermann et al. | |
| 8,735,349 B2 | 5/2014 | Silvestre et al. | |
| 2001/0012829 A1 | 8/2001 | Anderson et al. | |
| 2001/0033868 A1 | 10/2001 | Rossling et al. | |
| 2001/0039260 A1 | 11/2001 | Havelund | |
| 2001/0047084 A1 | 11/2001 | Knudsen et al. | |
| 2002/0107265 A1 | 8/2002 | Chen et al. | |
| 2002/0132760 A1 | 9/2002 | Van Antwerp et al. | |
| 2002/0177151 A1 | 11/2002 | Gimeno | |
| 2002/0198140 A1 | 12/2002 | Havelund | |
| 2003/0004096 A1 | 1/2003 | Boderke | |
| 2003/0026872 A1 | 2/2003 | Dake et al. | |
| 2003/0104983 A1 | 6/2003 | DeFelippis et al. | |
| 2003/0170691 A1 | 9/2003 | Gimeno | |
| 2004/0037893 A1 | 2/2004 | Hansen et al. | |
| 2004/0048783 A1 | 3/2004 | Brunner-Schwarz et al. | |
| 2004/0092590 A1 | 5/2004 | Arterburn et al. | |
| 2004/0097410 A1 | 5/2004 | Zheng et al. | |
| 2004/0106547 A1 | 6/2004 | Larsen et al. | |
| 2004/0186046 A1 | 9/2004 | Burgess et al. | |
| 2004/0229774 A1 | 11/2004 | Rosskamp et al. | |
| 2004/0235710 A1 | 11/2004 | DeFelippis et al. | |
| 2004/0242853 A1 | 12/2004 | Greig et al. | |
| 2005/0014679 A1 | 1/2005 | Beals et al. | |
| 2005/0079996 A1 | 4/2005 | Horiguchi et al. | |
| 2005/0106147 A1 | 5/2005 | Jordan et al. | |
| 2005/0171009 A1 | 8/2005 | Brunner-Schwarz et al. | |
| 2005/0209142 A1 | 9/2005 | Bertilsson et al. | |
| 2006/0004049 A1 | 1/2006 | Yao et al. | |
| 2006/0014678 A1 | 1/2006 | Cowley et al. | |
| 2006/0019347 A1 | 1/2006 | Cho et al. | |
| 2006/0057137 A1 | 3/2006 | Steiness | |
| 2006/0073213 A1 | 4/2006 | Hotamisligil et al. | |
| 2006/0093576 A1 | 5/2006 | Chen et al. | |
| 2006/0194719 A1 | 8/2006 | Ebbehoj et al. | |
| 2006/0239933 A1 | 10/2006 | Nilsson et al. | |
| 2006/0287221 A1 | 12/2006 | Knudsen et al. | |
| 2007/0027063 A1 | 2/2007 | Boss et al. | |
| 2007/0111940 A1 | 5/2007 | Larsen et al. | |
| 2007/0128193 A1 | 6/2007 | O'Neil et al. | |
| 2007/0135338 A1 | 6/2007 | O'Neil et al. | |
| 2007/0155653 A1 | 7/2007 | Boderke | |
| 2007/0191271 A1 | 8/2007 | Mayhew et al. | |
| 2007/0237827 A1 | 10/2007 | Sung et al. | |

(56) References Cited

U.S. PATENT DOCUMENTS

| | | | |
|---|---|---|---|
| 2008/0064856 A1 | 3/2008 | Warne et al. | |
| 2008/0146490 A1 | 6/2008 | Joabsson et al. | |
| 2008/0234200 A1 | 9/2008 | Quay et al. | |
| 2008/0248999 A1* | 10/2008 | Steiner | 514/4 |
| 2008/0260840 A1 | 10/2008 | Alessi et al. | |
| 2008/0267907 A1 | 10/2008 | Poulsen | |
| 2009/0082255 A1 | 3/2009 | Brunner-Schwarz et al. | |
| 2009/0088369 A1 | 4/2009 | Steiness | |
| 2009/0099064 A1 | 4/2009 | Lougheed | |
| 2009/0142338 A1 | 6/2009 | Levetan | |
| 2009/0175840 A1 | 7/2009 | Kashyap et al. | |
| 2009/0176692 A1 | 7/2009 | Habermann et al. | |
| 2009/0180953 A1 | 7/2009 | Gotthardt et al. | |
| 2009/0186819 A1* | 7/2009 | Carrier et al. | 514/12 |
| 2009/0208565 A1 | 8/2009 | Ebbehoj et al. | |
| 2009/0214468 A1 | 8/2009 | Lin et al. | |
| 2009/0214657 A1 | 8/2009 | Qazi | |
| 2009/0304665 A1* | 12/2009 | Frost et al. | 424/94.5 |
| 2009/0312236 A1 | 12/2009 | Beals et al. | |
| 2009/0324701 A1* | 12/2009 | Williams | 424/450 |
| 2010/0029558 A1 | 2/2010 | Bristow | |
| 2010/0055049 A1 | 3/2010 | Kuo et al. | |
| 2010/0057194 A1 | 3/2010 | Ryan | |
| 2010/0069292 A1 | 3/2010 | Pohl et al. | |
| 2010/0069293 A1 | 3/2010 | Bolotin et al. | |
| 2010/0227816 A1 | 9/2010 | Fiatt et al. | |
| 2010/0279931 A1 | 11/2010 | Garibay et al. | |
| 2010/0311112 A1 | 12/2010 | Rissom et al. | |
| 2011/0020294 A1 | 1/2011 | Hammerman | |
| 2011/0021423 A1 | 1/2011 | Olsen et al. | |
| 2011/0077197 A1 | 3/2011 | Habermann et al. | |
| 2011/0118178 A1 | 5/2011 | Silvestre et al. | |
| 2011/0118180 A1 | 5/2011 | Silvestre et al. | |
| 2011/0144008 A1 | 6/2011 | Larsen et al. | |
| 2011/0152185 A1 | 6/2011 | Plum et al. | |
| 2011/0173722 A1 | 7/2011 | Habermann et al. | |
| 2011/0230402 A1 | 9/2011 | Johansen et al. | |
| 2011/0236925 A1 | 9/2011 | Hazra et al. | |
| 2011/0245165 A1 | 10/2011 | Larsen et al. | |
| 2011/0281790 A1 | 11/2011 | Pohl et al. | |
| 2011/0301081 A1 | 12/2011 | Becker et al. | |
| 2012/0021978 A1 | 1/2012 | Werner et al. | |
| 2012/0121611 A1 | 5/2012 | Lodie et al. | |
| 2012/0122774 A1 | 5/2012 | Becker et al. | |
| 2012/0183616 A1 | 7/2012 | Sprogoe et al. | |
| 2012/0232002 A1* | 9/2012 | Schoettle et al. | 514/6.2 |
| 2012/0241356 A1 | 9/2012 | Pfenninger et al. | |
| 2012/0252724 A1* | 10/2012 | Schoettle et al. | 514/6.2 |
| 2012/0277147 A1 | 11/2012 | Boka et al. | |
| 2012/0283179 A1* | 11/2012 | Brunner-Schwarz et al. | 514/5.3 |
| 2012/0316108 A1 | 12/2012 | Chen et al. | |
| 2013/0005649 A1 | 1/2013 | Niemoeller et al. | |
| 2013/0012433 A1 | 1/2013 | Rosskamp et al. | |
| 2013/0023467 A1 | 1/2013 | Silvestre et al. | |
| 2013/0040878 A1 | 2/2013 | Silvestre et al. | |
| 2013/0065828 A1 | 3/2013 | Ruus et al. | |
| 2013/0079279 A1 | 3/2013 | Becker et al. | |
| 2013/0085102 A1 | 4/2013 | Silvestre et al. | |
| 2013/0096059 A1 | 4/2013 | Stechl et al. | |
| 2013/0096060 A1 | 4/2013 | Stechl et al. | |
| 2013/0203666 A1 | 8/2013 | Niemoeller et al. | |
| 2013/0284912 A1 | 10/2013 | Vogel et al. | |
| 2013/0296236 A1 | 11/2013 | Silvestre et al. | |
| 2013/0317477 A1 | 11/2013 | Edwards et al. | |
| 2014/0148384 A1 | 5/2014 | Boka et al. | |
| 2014/0206611 A1 | 7/2014 | Becker et al. | |
| 2014/0248365 A1 | 9/2014 | Rademacher et al. | |

FOREIGN PATENT DOCUMENTS

| | | |
|---|---|---|
| CA | 1 173 388 | 8/1984 |
| CA | 1 341 203 | 11/1986 |
| CA | 1 258 427 | 8/1989 |
| CA | 1 336 329 | 7/1995 |
| CA | 2 662 084 | 3/2008 |
| CN | 1276731 | 12/2000 |
| CN | 1413582 | 4/2003 |
| CN | 101366692 A | 2/2009 |
| CN | 101444618 A | 6/2009 |
| CN | 101454019 | 6/2009 |
| CN | 101670096 A | 3/2010 |
| DE | 196 37 230 | 3/1998 |
| DE | 10 2008 003 566 | 7/2009 |
| DE | 10 2008 003 568 | 7/2009 |
| DE | 10 2008 053 048 | 4/2010 |
| EP | 0 046 979 | 8/1981 |
| EP | 0 132 769 | 2/1985 |
| EP | 0 140 084 | 5/1985 |
| EP | 0 166 529 | 1/1986 |
| EP | 0 194 864 | 3/1986 |
| EP | 0 200 383 | 11/1986 |
| EP | 0 211 299 | 2/1987 |
| EP | 0 214 826 | 3/1987 |
| EP | 0 224 885 | 6/1987 |
| EP | 0 227 938 | 7/1987 |
| EP | 0 229 998 | 7/1987 |
| EP | 0 254 516 | 1/1988 |
| EP | 0 368 187 | 5/1990 |
| EP | 0 375 437 | 6/1990 |
| EP | 0 383 472 | 8/1990 |
| EP | 0419504 A1 | 4/1991 |
| EP | 0 419 504 | 1/1994 |
| EP | 0 600 372 | 6/1994 |
| EP | 0 668 282 | 8/1995 |
| EP | 0 678 522 | 10/1995 |
| EP | 0 837 072 | 4/1998 |
| EP | 0 845 265 | 6/1998 |
| EP | 0 885 961 | 12/1998 |
| EP | 1 076 066 | 2/2001 |
| EP | 1 172 114 | 1/2002 |
| EP | 1 222 207 | 7/2002 |
| EP | 1 523 993 | 4/2005 |
| EP | 1364029 B1 | 12/2005 |
| EP | 2 112 161 | 10/2009 |
| EP | 2 324 853 | 5/2011 |
| EP | 2 329 848 | 6/2011 |
| EP | 2 389 945 | 11/2011 |
| EP | 0 921 812 | 12/2011 |
| EP | 2 387 989 | 7/2014 |
| FR | 2 456 522 | 12/1980 |
| GB | 0 835 638 | 5/1960 |
| GB | 0 840 870 | 7/1960 |
| GB | 1 527 605 | 10/1978 |
| GB | 1 554 157 | 10/1979 |
| JP | 61-212598 | 9/1986 |
| JP | 63-99096 | 9/1988 |
| JP | 2-218696 | 8/1990 |
| JP | 2-264798 | 10/1990 |
| JP | 3-504240 | 9/1991 |
| JP | 6-506444 | 7/1994 |
| JP | 2001-521004 | 11/2001 |
| JP | 2002-516880 | 6/2002 |
| JP | 2007-204498 | 8/2007 |
| JP | 2009-091363 | 4/2009 |
| RU | 2386631 C2 | 9/2008 |
| TW | 157005 | 5/1991 |
| TW | 562806 | 11/2003 |
| WO | WO 83/00288 | 2/1983 |
| WO | WO 88/06599 | 9/1988 |
| WO | WO 89/10937 | 11/1989 |
| WO | WO 90/07522 | 7/1990 |
| WO | WO 90/11299 | 10/1990 |
| WO | WO 91/03550 | 3/1991 |
| WO | WO 91/16929 | 11/1991 |
| WO | WO 92/00321 | 1/1992 |
| WO | WO 92/12999 | 8/1992 |
| WO | 9318786 | 9/1993 |
| WO | WO 94/14461 | 7/1994 |
| WO | WO 95/00550 | 1/1995 |
| WO | WO 95/24183 | 9/1995 |
| WO | WO 96/04307 | 2/1996 |
| WO | WO 96/07399 | 3/1996 |
| WO | WO 96/11705 | 4/1996 |
| WO | WO 96/32414 | 10/1996 |

(56) References Cited

FOREIGN PATENT DOCUMENTS

| | | |
|---|---|---|
| WO | WO 96/34882 | 11/1996 |
| WO | WO 96/41606 | 12/1996 |
| WO | WO 97/01331 | 1/1997 |
| WO | WO 97/48413 | 12/1997 |
| WO | WO 98/05351 | 2/1998 |
| WO | WO 98/08531 | 3/1998 |
| WO | WO 98/08871 | 3/1998 |
| WO | WO 98/08873 | 3/1998 |
| WO | WO 98/19698 | 5/1998 |
| WO | WO 98/30231 | 7/1998 |
| WO | WO 98/35033 | 8/1998 |
| WO | WO 98/39022 | 9/1998 |
| WO | WO 98/42749 | 10/1998 |
| WO | WO 98/56406 | 12/1998 |
| WO | WO 98/56418 | 12/1998 |
| WO | WO 99/07404 | 2/1999 |
| WO | WO 99/21573 | 5/1999 |
| WO | WO 99/21578 | 5/1999 |
| WO | WO 99/24071 | 5/1999 |
| WO | WO 99/25727 | 5/1999 |
| WO | WO 99/25728 | 5/1999 |
| WO | WO 99/40788 | 8/1999 |
| WO | WO 99/43708 | 9/1999 |
| WO | WO 99/46283 | 9/1999 |
| WO | WO 99/62558 | 12/1999 |
| WO | WO 00/23098 | 4/2000 |
| WO | WO 00/23099 | 4/2000 |
| WO | WO 00/29013 | 5/2000 |
| WO | WO 00/41546 | 7/2000 |
| WO | WO 00/66629 | 11/2000 |
| WO | WO 00/74736 | 12/2000 |
| WO | WO 01/00223 | 1/2001 |
| WO | WO 01/02039 | 1/2001 |
| WO | WO 01/04156 | 1/2001 |
| WO | WO 01/12155 | 2/2001 |
| WO | WO 01/21154 | 3/2001 |
| WO | WO 01/25278 | 4/2001 |
| WO | WO 01/28555 | 4/2001 |
| WO | WO-0124814 A1 | 4/2001 |
| WO | WO 01/37808 | 5/2001 |
| WO | WO 0132157 | 5/2001 |
| WO | WO 01/43762 | 6/2001 |
| WO | WO 01/51071 | 7/2001 |
| WO | WO 01/52937 | 7/2001 |
| WO | WO 01/93837 | 12/2001 |
| WO | WO 02/00243 | 1/2002 |
| WO | WO 02/24214 | 3/2002 |
| WO | WO 02/064115 | 8/2002 |
| WO | WO 02/065985 | 8/2002 |
| WO | WO 02/066628 | 8/2002 |
| WO | WO 02/068660 | 9/2002 |
| WO | WO 02/070722 | 9/2002 |
| WO | WO 02/076495 | 10/2002 |
| WO | WO 02/079250 | 10/2002 |
| WO | WO 03/002021 | 1/2003 |
| WO | 03020201 A2 | 3/2003 |
| WO | WO 03/035028 | 5/2003 |
| WO | WO 03/035051 | 5/2003 |
| WO | WO 03/044210 | 5/2003 |
| WO | WO 03/053339 | 7/2003 |
| WO | WO03/066084 A1 | 8/2003 |
| WO | WO 03/094951 | 11/2003 |
| WO | WO 03/094956 | 11/2003 |
| WO | WO 03/101395 | 12/2003 |
| WO | WO 03/105888 | 12/2003 |
| WO | WO 2004/005342 | 1/2004 |
| WO | 2004035623 A2 | 4/2004 |
| WO | WO 2004/045592 | 6/2004 |
| WO | WO-2004050115 A2 | 6/2004 |
| WO | WO 2004/064862 | 8/2004 |
| WO | WO 2004/078196 | 9/2004 |
| WO | WO 2004/078197 | 9/2004 |
| WO | WO 2004/078198 | 9/2004 |
| WO | WO 2004/080480 | 9/2004 |
| WO | WO 2004/096854 | 11/2004 |
| WO | WO 2004/105781 | 12/2004 |
| WO | WO 2004/107979 | 12/2004 |
| WO | WO 2005/021022 | 3/2005 |
| WO | WO 2005/023291 | 3/2005 |
| WO | WO 2005/028516 | 3/2005 |
| WO | WO2005/028516 A2 | 3/2005 |
| WO | 2005046716 A1 | 5/2005 |
| WO | 2005048950 A2 | 6/2005 |
| WO | 2005112949 A1 | 12/2005 |
| WO | WO 2005/117948 | 12/2005 |
| WO | WO 2006/000567 | 1/2006 |
| WO | WO 2006/015879 | 2/2006 |
| WO | 2006029634 A | 3/2006 |
| WO | 2006051103 A2 | 5/2006 |
| WO | WO 2006/051110 | 5/2006 |
| WO | WO 2006/058620 | 6/2006 |
| WO | 2006083952 A2 | 8/2006 |
| WO | 2006110551 A2 | 10/2006 |
| WO | WO 2007/001150 | 1/2007 |
| WO | WO 2007/006307 | 1/2007 |
| WO | WO 2007/024700 | 3/2007 |
| WO | WO 2007/028394 | 3/2007 |
| WO | WO 2007/031187 | 3/2007 |
| WO | WO 2007/035665 | 3/2007 |
| WO | WO-2007035665 A1 | 3/2007 |
| WO | WO 2007/036299 | 4/2007 |
| WO | WO 2007/037607 | 4/2007 |
| WO | WO 2007/044867 | 4/2007 |
| WO | WO 2007/050656 | 5/2007 |
| WO | WO 2007/075534 | 7/2007 |
| WO | WO 2007/081824 | 7/2007 |
| WO | WO-2007081792 A2 | 7/2007 |
| WO | WO 2007082381 A1 * | 7/2007 ............ A61K 31/27 |
| WO | WO 2007/095288 | 8/2007 |
| WO | WO2007/104786 A1 | 9/2007 |
| WO | WO 2007/109221 | 9/2007 |
| WO | 2007113205 A1 | 10/2007 |
| WO | WO 2007/120899 | 10/2007 |
| WO | WO 2008/006496 | 1/2008 |
| WO | WO 2008/013938 | 1/2008 |
| WO | WO 2008/021560 | 2/2008 |
| WO | WO 2008/023050 | 2/2008 |
| WO | WO 2008/028914 | 3/2008 |
| WO | WO 2008/034881 | 3/2008 |
| WO | WO 2008/124522 | 10/2008 |
| WO | WO2008/133908 A2 | 11/2008 |
| WO | WO 2008/145323 | 12/2008 |
| WO | WO 2009/004627 | 1/2009 |
| WO | WO 2009/030498 | 3/2009 |
| WO | WO 2009/030499 | 3/2009 |
| WO | WO 2009/039963 | 4/2009 |
| WO | WO 2009/048959 | 4/2009 |
| WO | WO 2009/056569 | 5/2009 |
| WO | WO 2009/063072 | 5/2009 |
| WO | WO 2009/087082 | 7/2009 |
| WO | WO 2009/089181 | 7/2009 |
| WO | 2009102467 A2 | 8/2009 |
| WO | WO 2009/098318 | 8/2009 |
| WO | WO 2009087081 A3 * | 9/2009 ............ C07K 14/62 |
| WO | WO 2009/134380 | 11/2009 |
| WO | WO 2009/143014 | 11/2009 |
| WO | 2010030670 A2 | 3/2010 |
| WO | 2010044867 A1 | 4/2010 |
| WO | WO 2010/043566 | 4/2010 |
| WO | WO 2010/092163 | 8/2010 |
| WO | WO-2010089304 A1 | 8/2010 |
| WO | WO-2010138671 A1 | 12/2010 |
| WO | WO 2011/003822 A2 | 1/2011 |
| WO | WO 2011/003823 A1 | 1/2011 |
| WO | WO 2011/017554 | 2/2011 |
| WO | 2011029892 A2 | 3/2011 |
| WO | WO 2011/012719 | 3/2011 |
| WO | WO 2011/089203 | 7/2011 |
| WO | WO 2011/103575 | 8/2011 |
| WO | WO 2011/122921 | 10/2011 |
| WO | WO 2011/128374 | 10/2011 |
| WO | WO 2011/144673 | 11/2011 |
| WO | WO 2011/144674 | 11/2011 |
| WO | WO 2011/147980 | 12/2011 |

(56) References Cited

FOREIGN PATENT DOCUMENTS

| WO | WO 2011/157402 | 12/2011 |
|---|---|---|
| WO | WO 2011/160066 | 12/2011 |
| WO | WO 2012/012352 | 1/2012 |
| WO | WO 2012/028172 | 3/2012 |
| WO | WO 2012/055967 | 5/2012 |
| WO | WO 2012/065996 | 5/2012 |
| WO | WO 2012/066086 | 5/2012 |
| WO | WO 2012/080320 | 6/2012 |
| WO | WO 2012/104342 | 8/2012 |
| WO | WO 2012/125569 | 9/2012 |
| WO | WO 2012/156296 | 11/2012 |
| WO | WO 2012/156299 | 11/2012 |
| WO | WO 2012/177929 | 12/2012 |
| WO | WO 2013/060850 | 5/2013 |
| WO | WO 2014/017849 | 1/2014 |
| WO | WO 2014/118355 | 8/2014 |
| WO | WO 2014/202483 | 12/2014 |
| WO | WO-2015059302 A1 | 4/2015 |

OTHER PUBLICATIONS

English Translation of a Notice of Opposition filed against the parallel application EC SP-12-11890-PCT.
English translation of Office Action dated Aug. 26, 2013 issued in parallel Korean Patent Application No. 10-2012-7014976.
International Preliminary Report on Patentability and Written Opinion issued in PCT/EP2010/067249 dated Jun. 12, 2012.
International Search Report dated Feb. 4, 2011 issued in PCT/EP2010/067249.
English Translation of Notice of Reasons for Rejection from the Japanese Patent Office dated Oct. 21, 2014 for Japanese Patent Application No. 2012-538332, pp. 1-4.
U.S. Appl. No. 13/509,507, filed Jul. 30, 2014 to Brunner-Schwarz et al.
U.S. Appl. No. 13/382,442, filed Mar. 21, 2012 to Schoettle et al.
U.S. Appl. No. 13/382,772, filed May 29, 2012 to Schoettle et al.
Non-Final Rejection issued in U.S. Appl. No. 13/509,507; dated Feb. 19, 2015, pp. 1-10.
Non-Final Rejection issued in U.S. Appl. No. 13/509,507; dated Sep. 19, 2014, pp. 1-9.
Non-Final Rejection issued in U.S. Appl. No. 13/509,507; dated Aug. 6, 2013, pp. 1-11.
Non-Final Rejection issued in U.S. Appl. No. 13/382,442; dated Feb. 5, 2015, pp. 1-31.
Final Rejection issued in U.S. Appl. No. 13/382,442; dated Jun. 13, 2014, pp. 1-29.
Non-Final Rejection issued in U.S. Appl. No. 13/382,442; dated Dec. 19, 2013, pp. 1-29.
Final Rejection issued in U.S. Appl. No. 13/382,442; dated Jul. 17, 2013, pp. 1-30.
Non-Final Rejection issued in U.S. Appl. No. 13/382,442; dated Nov. 7, 2012, pp. 1-26.
Final Rejection issued in U.S. Appl. No. 13/382,772; dated Feb. 10, 2015, pp. 1-36.
Non-Final Rejection issued in U.S. Appl. No. 13/382,772; dated Sep. 29, 2014, pp. 1-33.
Final Rejection issued in U.S. Appl. No. 13/382,772; dated Jun. 3, 2014, pp. 1-34.
Non-Final Rejection issued in U.S. Appl. No. 13/382,772; dated Nov. 21, 2013, pp. 1-42.
Non-Final Rejection issued in U.S. Appl. No. 13/382,772; dated Apr. 10, 2013, pp. 1-48.
Arnolds & Rave, "Basal insulin glargine vs prandial insulin lispro in type 2 diabetes," Lancet 378(9636):370-71 (2008).
Brange, "Design of Insulin Analogues for Meal-Related Therapy", J. Diabetes Complications 7(2):106-112 (Apr.-Jun. 1993). Abstract provided.
Brange et al., "Toward Understanding Insulin Fibrillation," Journal of Pharmaceutical Sciences, 86(5):517-25 (1997).
Byrne et al., "Inhibitory Effects of Hyperglycaemia on Fed Jejunal Motility: Potential Role of Hyperinsulinaemia," Euro. J. Clin. Invest 28(1):72-78 (1998).
Campbell et al., "Insulin Glargine," Clin. Therapeutics 23(12):1938-57 (2001).
Chen & Drucker, "Tissue-specific Expression of Unique mRNAs That Encode Proglucagon-derived Peptides or Exendin 4 in the Lizard," J. Biol. Chem. 272(7):4108-15 (1997).
D'Alessio et al., "Glucagon-like Peptide 1 Enhances Glucose Tolerance Both by Stimulation of Insulin Release and by Increasing Insulin-independent Glucose Disposal," J. Clin. Invest. 93(5):2263-66 (1994).
Deacon et al., "Dipeptidyl Peptidase IV Inhibition Potentiates the Insulinotropic Effect of Glucagon-Like Peptide 1 in the Anesthetized Pig," Diabetes 47(5):764-69 (1998).
Deacon et al., "Dipeptidyl Peptidase IV Resistant Analogues of Glucagon-Like Peptide-1 Which Have Extended Metabolic Stability and Improved Biological Activity," Diabetologia 41(3):271-78 (1998).
Drucker, "The Biology of Incretin Hormones," Cell Metab. 3(3):153-65 (2006).
Drucker, "Glucagon-Like Peptides," Diabetes 47(2):159-69 (1998).
Drucker, "Mini review: The Glucagon-Like Peptides," Endocrinology 142(2):521-27 (2001).
DrugBank, "Insulin glargine," available online at http://www.drugbank.ca/drugs/DB00047, 16 pages (accessed online Sep. 25, 2014).
Eng et al., "Isolation and characterization of exendin-4, an exendin-3 analogue, from Heloderma suspectum venom. Further evidence for an exendin receptor on dispersed acini from guinea pig pancreas," J Biol Chem 267(11):7402-5 (1992).
Goke et al., "Distribution of GLP-1 Binding Sites in the Rat Brain: Evidence that Exendin-4 is a Ligand of Brain GLP-1 . Binding Sites," Eur. J. Neurosci. 7(11):2294-2300 (1995).
Goke et al., "Exendin-4 is a High Potency Agonist and Truncated Exendin-(9-39)-amide an Antagonist at the Glucagon-like Peptide 1-(7-36)-amide Receptor of Insulin-secreting beta-Cells," J. Biol. Chem. 268:19650-55 (1993).
Greig et al., "Once Daily Injection of Exendin-4 to Diabetic Mice Achieves Long-Term Beneficial Effects on Blood Glucose Concentrations." Diabetologia 42(1):45-50 (1999).
Gutniak et al., "Antidiabetogenic Effect of Glucagon-Like Peptide-1 (7-36) Amide in Normal Subjects and Patients with Diabetes Mellitus," N. Engl. J. Med. 326:1316-1322 (1992).
Heinrich et al., "Pre-proglucagon messenger ribonucleic acid: nucleotide and encoded amino acid sequences of the rat pancreatic complementary deoxyribonucleic acid," Endocrinol. 115(6):2176-81 (1984).
Holst, "Glucagon-like Peptide-1, A Gastrointestinal Hormone with a Pharmaceutical Potential," Current Medicinal Chemistry 6:1005-17 (1999).
Knudsen et al., "Potent Derivatives of Glucagon-Like Peptide-1 With Pharmacokinetic Properties Suitable for Once Daily Administration", J. Med. Chem. 43(9):1664-69 (2000).
Kolterman et al., "Synthetic Exendin-4 (Exenatide) Significantly Reduces Postprandial and Fasting Plasma Glucose in Subjects with Type 2 Diabetes," J. Clin. Endocrine. Metab. 88(7):3082-89 (2003).
Larsen & Holm, "Sequence-Assisted Peptide Synthesis (SAPS)," J. Pept. Res. 52(6):470-76 (1998).
Lopez-Delgado et al., "Effects of Glucagon-Like Peptide I on the Kinetics of Glycogen Synthase a in Hepatocytes from Normal and Diabetic Rats," Endocrinology 139(6):2811-2817 (1998).
Merrifield, "Solid Phase Synthesis." Science 232(4748):341-47 (1986).
Nathan et al., "Insulinotropic Action of Glucagon like Peptide-1-(7-37) in Diabetic and Nondiabetic Subjects," Diabetes Care 15(2):270-76 (1992).
Nauck et al., "Glucagon-like peptide 1 (GLP-1) as a new therapeutic approach for type 2-diabetes," Exp Clin Endocrinol. Diabetes 105(4):187-95 (1997).
Nauck et al., "Glucagon-Like Peptide 1 and its Potential in the Treatment of Non-Insulin-Dependent Diaetes Mellitus," Horm. Metab. Res. 29(9):411-16 (1997).

(56) References Cited

OTHER PUBLICATIONS

Needleman & Wunsch, "A General Method Applicable to the Search for Similarities in the Amino Acid Sequence of Two Proteins," J. Mol. Biol. 48:443-453 (1970).
Nielsen et al., "Pharmacology of Exenatide (Synthetic Exendin-4): A Potential Therapeutic for Improved Glycemic Control of Type 2 Diabetes," Regul. Pept. 117(2):77-88 (2004).
Orskov, "Glucagon-like Peptide-1, a New Hormone of the Enteroinsular Axis," Diabetologia 35(8):701-711 (1992).
Pederson et al., "Improved Glucose Tolerance in Zucker Fatty Rats by Oral Administration of the Dipeptidyl Peptidase IV Inhibitor Isoleucine Thiazolidide." Diabetes 47(8):1253-58 (1998).
Pohl & Wank, "Molecular Cloning of the Heloderman and Exendin-4 cDNAs in the Lizard," J. Biol. Chem. 273 (16):9778-84 (1998).
Raufman "Bioactive peptides from lizard venoms," Regul Pept 61(1):1-18 (1996).
Ritzel et al., "A Synthetic Glucagon-Like Peptide-1 Analog with Improved Plasma Stability," J. Endocrine. 159 (1):93-102 (1998).
Schubert-Zsilavecz & Wurglics, "Better blood sugar control in diabetics. Insulin glargin—a long acting insulin analogue," Pharmazie in Unserer Zeit 30(2):125-30 (2001). With English translation.
Tessari et al., "Insulin in Methionine and Homocysteine Kinetics in Healthy Humans: Plasma Vs. Intracellular Models", Am J. Physiol Endocrine Metab 288(6):E1270-E1276 (2005).
The Diabetes Control and Complications Trial Research Group, "The effect of intensive treatment of diabetes on the development and progression of long-term complications in insulin-dependent diabetes mellitus," N Engl J Med. 329 (14):977-86 (1993).
Uttenthel et al., "Molecular forms of flucagon-like peptide-1 in human pancreas and glucagonomas," J. Clin. Endocrinol. Metabol. 61(3):472-79 (1985).
Wan et al., "Enhancing the Activity of Insulin at the Receptor Interface: Crystal Structure and Photo-Cross-Linking of A8 Analogues," Biochemistry 43:16119-33 (2004).
Weiss et al., "Activities of Monomeric Insulin Analogs at Position A8 Are Uncorrelated With Their Thermodynamic Stabilities", The Journal of Biological Chemistry 276(43):40018-24 (2001).
Yu et al., "Effect of zinc sulphate and zinc methionine on growth, plasma growth hormone concentration, growth hormone receptor and insulin-like growth factor-I gene expression in mice," Clin Exp Pharmacol Physiol. 32(4):273-8 (2005). Abstract provided.
Nauck et al., "Effects of subcutaneous glucagon-like peptide 1 (GLP-1 [7-36 amide]) in patients with NIDDM," Diabetologia 39:1546-53 (1996).
"Suspension," Taber's Cyclopedic Medical Dictionary, 19th Edition, p. 2097 (F.A. Davis Co., Philadelphia 2001).
"Suspension," Stedman's Medical Dictionary, 20th Edition, p. 1450 (Williams & Wilkins Co., Baltimore 1961).
Sanofi Press Release "Positive Results for Investigational Compound Lyxumia (Lixisenatide) Presented at American Diabetes Association's 71st Annual Scientific Sessions," (Jun. 24, 2011), pp. 1-5.
Sanofi Press Release entitled "FDA Accepts Sanofi's New Drug Application for Basal Insulin Toujeo®," dated Jul. 8, 2014, pp. 1-2.
Sanofi Press Release entitled "Sanofi Receives FDA Approval of Once-Daily Basal Insulin Toujeo®," dated Feb. 26, 2015, pp. 1-4.
Schapira, "Causes of neuronal death in Parkinson's disease." Adv Neurol 86:155-162 (2001).
Schellenberger et al., "Attempts for Quantifying the S' Subsite Specificity of Serine Proteases," Selected Papers Presented at the 2nd International Meeting on the Molecular and Cellular Regulation of Enzyme Activity, Advances in the Biosciences, Peptides and Proteases: Recent Advances 65:159-66 (1987).
Schellenberger et al., "Protease-Catalyzed Kinetically Controlled Peptide Synthesis," Angewante Chemie, International Edition 30(11):1437-49 (1991).

Schindowski et al., "Impact of Aging: Sporadic, and Genetic Risk Factors on Vulnerability to Apoptosis in Alzheimer's Disease" NeuroMolecular Medicine, 4:161-177 (2003).
Schmitz et al., "Hippocampal Neuron Loss Exceeds Amyloid Plaque Load in a Transgenic Mouse Model of Alzheimer's Disease" American Journal of Pathology, 164(4):1495-1502 (2004).
Schwartz et al., "A superactive insulin: [B10-Aspartic acid]insulin(human)," Proc. Natl. Acad. Sci. USA, 84 (18):6408-11 (Sep. 1987).
Secnik Boye et al., "Patient-reported outcomes in a trial of exenatide and insulin glargine for the treatment of type 2 diabetes," Health and Quality of Life Outcomes, vol. 4, No. 80, pp. 1-8 (Oct. 2006).
Seino et al., "Randomized, double-blind, placebo-controlled trial of the once-daily GLP-1 receptor agonist lixisenatide in Asian patients with type 2 diabetes insufficiently controlled on basal insulin with or without a sulfonylurea (GetGoal-L-Asia)." Diabetes, Obesity and Metabolism 14(10):910-17 (2012).
Sharplin et al., "Improved glycaemic control by switching from insulin NPH to insulin glargine: a retrospective observational study," Cardiovascular Diabetology, 8(3):1-8 (published Jan. 19, 2009).
Sherer et al., "Subcutaneous Rotenone Exposure Causes Highly Selective Dopaminergic Degeneration and a-Synuclein Aggregation," Experimental Neurology, 179:9-16 (2003).
Sluzky et al., "Kinetics of Insulin Aggregation in Aqueous Solutions Upon Agitation in the Presence of Hydrophobic Surfaces," Proc. Natl. Acad. Sci. USA. 88(21):9377-81 (Nov. 1991).
Sporn & Suh, "Chemoprevention of cancer" Carcinogenesis, 21(3):535-530 (2000).
St. John Providence Health Center, "Preventing Obesity" http://www.stjohnprovidence.org/HealthInfolib/swarticle.aspx?type=85&id=P07863, Retrieved Aug. 22, 2013, pp. 1-2.
Starkova, ed., "Clinical Endocrinology", Guide for physicians, Moscow, "Medicine", 1991, p. 192-262.
Stolk et al., "Insulin and cognitive function in an elderly population. The Rotterdam Study." Diabetes Care, 20:792-95 (1997).
Summary of Product Characteristics Lyxumia 10 micrograms solution for injection, pp. 1-93, with European Medicines Agency product information, p. 94, published Mar. 14, 2013.
Sundby "Separation and Characterization of Acid-Induced Insulin Transformation Products by Paper Electrophoresis in 7 M Urea," J. Biol. Chem. 237(11):3406-11 (Nov. 1962).
Tanner et al., "Rotenone, Paraquat, and Parkinson's Disease," Environmental Health Perspectives,119:866-872 (2011).
Tempero, "How I treat Pancreatic Ductal Adenocarcinoma," Current Clinical Issues, Journal of Oncology Practice, vol. 4, Issue 1, pp. 46-47 (2008).
Teramoto et al., "Exendin-4, a glucagon-like peptide-1 receptor agonist, provides neuroprotection in mice transient focal cerebral ischemia" J Cerebr Blood Flow Metab (2011) pp. 1696-1705, vol. 31, No. 8.
Tetich et al., "Neuroprotective effects of (24R)-1,24-dihydroxycholecalciferol in human neuroblastoma SH-SY5Y cell line" J Steroid Biochemistry & Molecular Biology 89-90:365-70 (2004).
Tews et al., Abstract of Oral Presentation "Enhanced Protection Against Cytokine- and Fatty Acid-induced Apoptosis in Ins-1 Beta-Cells by Combined Treatment with Insulin Glargine and the Novel GLP-1 Receptor Agonist AVE0010" Diabetes, 56(Suppl. 1):A72-A73 (2007).
Thong et al., "Safety, efficacy and tolerability of exenatide in combination with insulin in the Association of British Clinical Diabetologists nationwide exenatide audit." Diabetes, Obesity and Metabolism 13:703-10 (2011).
Toth et al., "Neurite sprouting and synapse deterioration in the aging Caenorhabditis elegans nervous system" J Neurosci. 32(26):8778-90 (2012).
Turner et al., UK Prospective Diabetes Study (UKPDS) Group "Glycemic control with diet, sulfonylurea, metformin, or insulin in patients with type 2 diabetes mellitus: Progressive requirement for multiple therapies (UKPDS 49)." JAMA 281(21):2005-12 (1999).

(56) References Cited

OTHER PUBLICATIONS

Tyler-Cross Schirch, "Effects of amino acid sequence, buffers, and ionic strength on the rate and mechanism of deamidation of asparagine residues in small peptides," J Biol Chem. 266(33):22549-56 (1991).
UK Prospective Diabetes Study (UKPDS) Group "Intensive blood-glucose control with sulphonylureas or insulin compared with conventional treatment and risk of complications in patients with type 2 diabetes (UKPDS 33)" The Lancet vol. 352 p. 837-853 (Sep. 12, 1998).
UK Prospective Diabetes Study (UKPDS) Group, "Effect of intensive blood-glucose control with metformin on complications in overweight patients with type 2 diabetes (UKPDS 34)." Lancet 352(9131):854-65 (Sep. 1998).
Valle et al., "Cisplatin plus Gemcitabine versus Gemcitabine for Biliary Tract Cancer," N Engl J Med. 362 (14):1273-81 (Apr. 2010).
Van Delden, "Pancreas-Carcinoma, CT Assessment of Resectability," Radiology Department of the Academical Medical Centre, pp. 1-12 (Apr. 2006).
Varadarajan et al., "Review: Alzheimer's Amyloid b-Peptide-Associated Free Radical Oxidative Stress and Neurotoxicity," Journal of Structural Biology, 130:184-208 (2000).
Venezia et al., "Apoptotic cell death and amyloid precursor protein signaling in neuroblastoma SH-SY5Y cells," Ann NY Acad Sci., 1030:339-47 (2004).
Victoza Press Release, "Diabetes drugs show promise in Alzheimer's" published Jan. 17, 2011, pp. 1-2.
Victoza® Product information—European Medicines Agency, first published Aug. 7, 2009, pp. 1-2.
Victoza® ANNEX I—Summary of product characteristics. First published 2009, pp. 1-32.
Vora et al., "Incretin-based therapy in combination with basal insulin: A promising tactic for the treatment of type 2 diabetes." Diabetes & Metab. 39(1):6-15 (2013).
Wafa et al., "Use of U-500 Regular Insulin in Type 2 Diabetes", Diabetes Care, 29(9):2175-2176 (2006).
Wajchenberg, Chapter 23 "Clinical Approaches to preserve beta-cell function in Diabetes", Adv Exp Med Biol. 654:515-35 (2010).
Wang et al., "Real-world outcomes of US employees with type 2 diabetes mellitus treated with insulin glargine or neutral protamine Hagedorn insulin: a comparative retrospective database study." BMJ Open. 3:e002348 (2013), pp. 1-9.
Watson et al., "Insulin increases CSF Aβ42 levels in normal older adults" Neurology 60:1899-1903 (2003).
Werner et al., "Pharmacological profile of lixisenatide: A new GLP-1 receptor agonist for the treatment of type 2 diabetes." Regulatory Peptides 164(2-3):58-64 (Epub Jun. 2, 2010).
Werner et al., "Insulin Glargine U-100 Has a Favourable Time-Action Profile Compared to U-40 or NPH Insulin in Healthy, Normoglycaemic Dogs", Poster-Abstract 37th Annual Meeting of Endocrine Society of India, Tirupati, A.P., India ESICON (2007) (2 pages including Abstract and Poster).
Weyer et al., "Long-term changes in insulin action and insulin secretion associated with gain, loss, regain and maintenance of body weight", Diabetologia, (43)1:36-46 (Jan. 2000).
White et al., "Randomized clinical trials with added rescue medication: some approaches to their analysis and interpretation." Statistics in Medicine 20:2995-3008 (2001).
Whittingham et al., "Insulin at PH2: Structural Analysis of the Conditions Promoting Insulin Fibre Formation" J. Mol. Biol., (2002), vol. 318, pp. 479-490.
WHO BMI classification, accessed at URL apps.who.int/bmi/index.jsp?introPage=itrol_3.html, Sep. 9, 2013, one page.
WHO Drug Information vol. 22(2), list 99, p. 142 (lixisenatide) (Jul. 2008).
International Search Report by the ISA for International Application No. PCT/EP2012/051670; dated Mar. 26, 2012, pp. 1-6.
International Search Report by the ISA for International Application No. PCT/EP2012/055660; dated May 10, 2012, pp. 1-15.
International Search Report by the ISA for International Application No. PCT/EP2012/058745; dated Jul. 12, 2012, pp. 1-6.
International Search Report by the ISA for International Application No. PCT/EP2012/058747; dated Jul. 8, 2012, pp. 1-6.
International Search Report by the ISA for International Application No. PCT/EP2012/058749; dated Jul. 31, 2012, pp. 1-6.
International Search Report by the ISA for International Application No. PCT/EP2012/058779; dated Aug. 28, 2012, pp. 1-5.
International Search Report by the ISA for International Application No. PCT/EP2012/066617; dated Nov. 22, 2012, pp. 1-5.
International Search Report by the ISA for International Application No. PCT/EP2012/067144; dated Aug. 11, 2012, pp. 1-6.
International Search Report by the ISA for International Application No. PCT/EP2012/069485; dated Dec. 11, 2012, pp. 1-5.
International Search Report by the ISA for International Application No. PCT/EP2012/069483; dated Nov. 29, 2011, pp. 1-4.
International Search Report by the ISA for International Application No. PCT/EP2012/071271; dated Jan. 30, 2013, pp. 1-5.
International Search Report by the ISA for International Application No. PCT/EP2012/074150; dated Nov. 20, 2012, pp. 1-4.
International Search Report by the ISA for International Application No. PCT/EP2014/062418; dated Sep. 22, 2014, pp. 1-4.
International Search Report by the ISA for International Application No. PCT/EP2014/051976; dated Mar. 4, 2014, pp. 1-3.
International Search Report by the ISA for International Application No. PCT/EP2014/056498; dated Jun. 25, 2014, pp. 1-10.
Written Opinion of the ISA for International Application No. PCT/EP2011/058079, mailed Mar. 22, 2012, pp. 1-8.
Extended European Search Report for Euorpean Application No. 98 11 0889.7; dated Oct. 14, 1998, pp. 1-4.
Extended European Search Report for European Application No. 09 17 5876.3; dated Mar. 24, 2010, pp. 1-4.
Extended European Search Report for European Application No. 09 17 5877.1; dated Apr. 29, 2010, pp. 1-5.
Extended European Search Report for European Application No. 10 16 4368.2; dated Oct. 14, 2010, pp. 1-6.
Extended European Search Report for European Application No. 10 30 5780; dated Nov. 16, 2010, pp. 1-3.
Extended European Search Report for European Application No. 11 15 3106; dated Jul. 22, 2011, pp. 1-12.
Extended European Search Report for European Application No. 11 16 0270.2; dated Sep. 19, 2011, pp. 1-8.
Extended European Search Report for European Application No. 11 16 6415; dated Mar. 20, 2012, pp. 1-12.
Extended European Search Report for European Application No. 11 17 9149.7; dated Feb. 9, 2012, pp. 1-8.
Extended European Search Report for European Application No. 13 305 126; dated Apr. 23, 2013, pp. 1-7.
Extended European Search Report for European Application No. 13 305 432.0; dated Sep. 13, 2013, pp. 1-5.
Extended European Search Report for European Application No. 14 16 6877.2; of Aug. 18, 2014, pp. 1-6.
Extended European Search Report for European Application No. 14 19 7154.9: dated Apr. 8, 2015, pp. 1-7.
English translation of Search Report for Chinese Patent Application No. 20140220537.9; dated Feb. 13, 2015, pp. 1-2.
English translation of Search Report for Chinese Patent Application No. 201280053404.6; dated Feb. 10, 2015, pp. 1-3.
Search Report of the Intellectual Property Corporation of Malaysia for Malaysian Patent Application No. PI 2011006204; dated Sep. 15, 2015, pp. 1-3.
Search Report of the Indecopi for Patent Application in Peru No. 000643-2012/DIN, dated Jul. 23, 2015, pp. 1-2.
Final Rejection issued in U.S. Appl. No. 12/617,811; dated Jul. 31, 2015, pp. 1-15.
Non-Final Rejection issued in U.S. Appl. No. 14/220,562; dated Apr. 8, 2015, pp. 1-18.
Non-Final Rejection issued in U.S. Appl. No. 14/624,575; dated Mar. 26, 2015, pp. 1-14.
http://diabetes.emedtv.com/lantus/generic-lantus.html , 2 pages, accessed on Nov. 12, 2015.

(56) References Cited

OTHER PUBLICATIONS

18th World Health Congress (Helsinki). WMA Declaration of Helsinki—Ethical Principles for Medical Research Involving Human Subjects; WMA; Jun. 1964, pp. 1-8.
Abbas et al., "Impairment of synaptic plasticity and memory formation in GLP-1 receptor KO mice: Interaction between type 2 diabetes and Alzheimer's disease," Behav. Brain Res. 205:265-271 (2009).
Action to Control Cardiovascular Risk in Diabetes Study Group, "Effects of intensive glucose lowering in type 2 diabetes." N Engl J. Med. 358(24):2545-59 (2008).
Aderinwale et al., "Current therapies and new strategies for the management of Alzheimer's disease," Am J Alzheimers Dis Other Demen., 25(5):414-24 (2010).
Agholme et al., "An in Vitro Model for Neuroscience: Differentiation of SH-SY5Y Cells into Cells with Morphological and Biochemical Characteristics of Mature Neurons" J Alzheimer's Disease, 20:1069-82 (2010).
American Diabetes Association (ADA) Committee Report—The Expert Committee on the Diagnosis and Classification of Diabetes Mellitus—Report of the Expert Committee on the Diagnosis and Classification of Diabetes Mellitus, Diabetes Care, 21(Supplement 1): S5-S19 (Jan. 1998).
Akbar, "Sub-Optimal postprandial blood glucose level in diabetics attending the outpatient clinic of a University Hospital" Saudi Med Journal, 24(10):1109-1112 (Oct. 2003).
Ahren et al., Abstract "Efficacy and Safety of Lixisenatide QD Morning and Evening Injections vs Placebo in T2DM Inadequately Controlled on Metformin (GetGoal-M)" Oral presentation O-0591 presented at the World Diabetes Congress in Dubai, Dec. 5-8, 2011, one page.
Arnolds et al., "Further improvement in postprandial glucose control with addition of exenatide or sitagliptin to combination therapy with insulin glargine and metformin—a proof-of-concept study" Diabetes Care 33(7):1509-15 (2010).
Auerbach et al., "Angiogenesis assays: Problems and Pitfalls," Cancer and Metastasis Reviews, 19:167-72 (2000).
Bakaysa et al., "Physicochemical basis for the rapid time-action of Lys.sup.B28 and Pro.sup.B29-insulin: Dissociation of a protein-ligand complex," Protein Science 5:2521-31 (1996).
Banks et al., "Brain Uptake of the Glucagon-Like Peptide-1 Antagonist Exendin(9-39) after Intranasal Administration" Journal of Pharmacology and Experimental Therapeutics, 309:469-75 (2004).
Barnett & Owens, "Insulin Analogues," Lancet 349(9044):47-51 (1997).
Barnett et al., "Tolerability and efficacy of exenatide and titrated insulin glargine in adult patients with type 2 diabetes previously uncontrolled with metformin or a sulfonylurea: a multinational, randomized, open-label, two-period, crossover noninferiority trial." Clinical Therapeutics 29(11):2333-48 (Nov. 2007).
Barnett "Lixisenatide: evidence for its potential use in the treatment of type 2 diabetes." Core Evidence 6:67-79 (published online Sep. 8, 2011).
Barnett, "Insulin glargine in the treatment of type 1 and type 2 diabetes" Vascular Health and Risk Management 2:59-67 (published Jan. 25, 2006).
Barnett, "Dosing of Insulin Glargine in the Treatmetnt of Type 2 Diabetes," Clinical Ther. 29(6):987-99 (Jun. 2007).
Behar et al.. "Functional gallbladder and sphincter of oddi disorders." Gastroenterology 130(5):1498-1509 (2006).
Beintema & Campagne, "Molecular Evolution of Rodent Insulins," Mol. Biol. Evol. 4(1): 10-18, 1987.
Berlie et al., "Glucagon-like peptide-1 receptor agonists as add-on therapy to basal insulin in patients with type 2 diabetes: a systematic review." Diabetes, Metabolic Syndrome and Obesity: Targets and Therapy 5:165-74 (2012).
Bertram et al., "The Genetics of Alzheimer Disease: Back to the Future," Neuron, 68:270-81 (2010).
Bethel & Feinglos, "Basal insulin therapy in type 2 diabetes." J Am Board Fam Pract. 18(3):199-204 (May-Jun. 2005).

Bhatt et al., "Chemical pathways of peptide degradation. I. Deamidation of adrenocorticotropic hormone," Pharm Res. 7(6):593-9 (1990).
Bland and Altman, "Measurement error" BMJ 312:1654 (Jun. 29, 1996).
Best, Mathematics and Statistics, pp. 1-39 (1988).
Blanchard et al., "Time sequence of maturation of dystrophic neurites associate with Aβ deposits in APP/PS1 transgenic mice" Experimental Neurology, 184:247-63 (2003).
Bolen et al., "Systematic Review: Comparative Effectiveness and Safety of Oral Medications for Type 2 Diabetes Mellitus," Ann. Intern. Med. 147:386-399 (Epub Jul. 16, 2007).
Bolli et al., "Efficacy and safety of lixisenatide once-daily versus placebo in patients with type 2 diabetes mellitus insufficiently controlled on metformin (GetGoal-F1)." Presentation Abstract No. 784, EASD Meeting Sep. 12-16, 2014.
Bolli et al., "Efficacy and safety of lixisenatide once daily vs. placebo in people with Type 2 diabetes insufficiently controlled on metformin (GetGoal-F1)." Diabetic Medicine 31:176-184 (published online Oct. 24, 2013).
Boutajangout et al., "Characterisation of cytoskeletal abnormalities in mice transgenic for wild-type human tau and familial Alzheimer's disease mutants of APP and presenilin-1" Neurobiology of Disease, 15:47-60 (2004).
Boutajangout et al., "Increased tau phosphorylation but absence of formation of neurofibrillary tangles in mice double transgenic for human tau and Alzheimer mutant (M146L) presenilin-1" 318(1):29-33 (2003).
Brange & Langkjeer, "Chemical stability of insulin 3. Influence of excipients, formulation, and pH," Acta Pharma. Nord. 4(3):149-58 (1992).
Brange & Langkjaer, "Insulin Structure and Stability" Chapter 11; Pharm Biotechnol 5:315-50 (1993).
Brod et al., "Adherence patterns in patients with type 2 diabetes on basal insulin analogues: missed, mistimed and reduced doses." Curr Med Res Opin. 28(12):1933-46 (2012).
Brod et al., "Examining correlates of treatment satisfaction for injectable insulin in type 2 diabetes: lessons learned from a clinical trial comparing biphasic and basal analogues." Health Quality of Life Outcomes. 5:8 (2007), pp. 1-10.
Broderick et al., "Guidelines for the Management of Spontaneous Intracerebral Hemorrhage in Adults," Circulation 116:e391-e413 (2007).
Brown & Nichols, "Slow response to loss of glycemic control in type 2 diabetes mellitus," Am J Manag Care. 9 (3):213-17 (2003).
"Buffer" Oxford Dictionary of Biochemistry and Molecular Biology, Oxford University Press, 2001, p. 83.
Buse et al., "Use of twice-daily exenatide in Basal insulin-treated patients with type 2 diabetes: a randomized, controlled trial." Annals of Internal Medicine 154(2):103-12 (Jan. 2011).
Byetta—Summary of Product Characteristics, updated Jan. 27, 2015, last accessed Apr. 18, 2015, pp. 1-12.
Cadario, "Sitagliptin" Drug Information Perspectives, 30(4):1-6 (2010).
Campas et al., "AVE-0010 GLP-1 Receptor Agonist Treatment of Diabetes", Drugs of the Future 33(10):838-40 (Oct. 2008).
Casas et al., "Massive CA1/2 Neuronal Loss with Intraneuronal and N-Terminal Truncated Aβ 42 Accumulation in a Novel Alzheimer Transgenic Model" American Journal of Pathology 165(4):1289-1300 (2004).
Chancel, "Natixis Conference on Diabetes." Sanofi, Paris, pp. 1-23 (Nov. 8, 2011).
Chatterjee et al., "Insulin glargine and its place in the treatment of Types 1 and 2 diabetes mellitus." Expert Opin Pharmacother 7(10):1357-71 (2006).
Charles et al., "Prevention of Type 2 Diabetes Role of Metformin" Review Article, Drugs 1999; 58 Suppl. 1:71-73 (Sep. 1999).
Cheung et al., "Effects of all-trans-retinoic acid on human SH-SY5Y neuroblastoma as in vitro model in neurotoxicity research" NeuroToxicology, 30:127-35 (2009).
Childs et al., "Defining and Reporting Hypoglycemia in Diabetes," Diabetes Care 28(5):1245-9 (May 2005).

(56) References Cited

OTHER PUBLICATIONS

Cholangiocarcinoma, Johns Hopkins Medicine Webstite, https://gi.jhsps.org/GDL Disease.aspx?CurrentUDV=31&GDLCat_ID=AF793A59-B736-42CB-9E1FE79D2B9FC358&GDL_Disease_ID=A6D1OE80-887D-49A7-B3BB-0517D38CE757, accessed on May 14, 2014, pp. 1-12.
Non-Final Office Action issued in U.S. Appl. No. 13/123,835; dated May 28, 2015, pp. 1-11.
Non-Final Office Action issued in U.S. Appl. No. 13/123,835; dated Dec. 22, 2014, pp. 1-13.
Non-Final Office Action issued in U.S. Appl. No. 13/123,835; dated Jul. 19, 2012, pp. 1-14.
Non-Final Rejection issued in U.S. Appl. No. 13/382,772; dated Sep. 14, 2015, pp. 1-42.
Non-Final Rejection issued in U.S. Appl. No. 12/617,811; dated Jan. 14, 2015, pp. 1-15.
Final Rejection issued in U.S. Appl. No. 12/617,811; dated Jan. 4, 2013, pp. 1-6.
Non-Final Rejection issued in U.S. Appl. No. 12/617,811; dated Jun. 21, 2012, pp. 1-7.
Non-Final Rejection issued in U.S. Appl. No. 12/617,811; dated Oct. 27, 2011, pp. 1-13.
Non-Final Rejection issued in U.S. Appl. No. 12/617,811; dated Apr. 27, 2011, pp. 1-10.
Final Office Action from U.S. Appl. No. 12/617,805; dated Jan. 13, 2015, pp. 1-11.
Non-Final Office Action from U.S. Appl. No. 12/617,805; dated Jul. 24, 2014, pp. 1-12.
Final Office Action from U.S. Appl. No. 12/617,805; dated Feb. 11, 2013, pp. 1-13.
Non-Final Office Action from U.S. Appl. No. 12/617,805; dated May 2, 2012, pp. 1-11.
Non-Final Office Action from U.S. Appl. No. 12/617,805; dated May 10, 2011, pp. 1-12.
Final Rejection issued in U.S. Appl. No. 13/509,507; dated Jul. 23, 2015, pp. 1-11.
Non-Final Rejection issued in U.S. Appl. 14/172,151; dated Mar. 24, 2015, pp. 1-16.
Non-Final Rejection issued in U.S. Appl. No. 13/700,631; dated Apr. 22, 2013, pp. 1-27.
Non-Final Rejection issued in U.S. Appl. No. 13/700,631; dated Nov. 29, 2013, pp. 1-23.
Final Rejection issued in U.S. Appl. No. 13/700,631; dated Jun. 18, 2014, pp. 1-25.
Non-Final Rejection issued in U.S. Appl. No. 13/700,631; dated Nov. 18, 2014, pp. 1-22.
Non-Final Rejection issued in U.S. Appl. No. 13/819,114; dated Jul. 31, 2014, pp. 1-9.
Final Rejection issued in U.S. Appl. No. 13/819,114; dated Mar. 2, 2015, pp. 1-10.
Non-Final Rejection issued in U.S. Appl. No. 13/363,956; dated Apr. 10, 2013, pp. 1-15.
Non-Final Rejection issued in U.S. Appl. No. 13/363,956; dated Nov. 20, 2013, pp. 1-10.
Final Rejection issued in U.S. Appl. No. 13/363,956; dated May 20, 2014, pp. 1-16.
Non-Final Rejection issued in U.S. Appl. No. 13/363,956; dated Feb. 11, 2015, pp. 1-18.
Non-Final Rejection issued in U.S. Appl. No. 13/363,956; dated May 29, 2015, pp. 1-17.
Non-Final-Rejection issued in U.S. Appl. No. 13/432,811; dated Apr. 8, 2013, pp. 1-7.
Non-Final-Rejection issued in U.S. Appl. No. 13/432,811; dated Jul. 29, 2014, pp. 1-8.
Final-Rejection issued in U.S. Appl. No. 13/432,811; dated Sep. 6, 2014, pp. 1-8.
Final-Rejection issued in U.S. Appl. No. 13/432,811; dated Mar. 31, 2015, pp. 1-9.
Non-Final Rejection issued in U.S. Appl. No. 13/469,633; dated Mar. 27, 2013, pp. 1-39.
Non-Final Rejection issued in U.S. Appl. No. 13/469,633; dated Aug. 19, 2013, pp. 1-25.
Final Rejection issued in U.S. Appl. No. 13/469,633; dated Dec. 4, 2013, pp. 1-17.
Non-Final Rejection issued in U.S. Appl. No. 13/469,633; dated Aug. 22, 2014, pp. 1-23.
Non-Final Rejection issued in U.S. Appl. No. 13/467,707; dated Jul. 15, 2013, pp. 1-20.
Final Rejection issued in U.S. Appl. No. 13/467,707; dated Feb. 25, 2014, pp. 1-18.
Non-Final Rejection issued in U.S. Appl. No. 13/467,707; dated Jul. 25, 2014, pp. 1-22.
Final Rejection issued in U.S. Appl. No. 13/467,707; dated Jan. 7, 2015, pp. 1-8.
Non-Final Rejection issued in U.S. Appl. No. 13/467,707; dated Sep. 16, 2015, pp. 1-13.
Final Rejection issued in U.S. Appl. No. 13/110,568; dated Feb. 21, 2013, pp. 1-20.
Non-Final Rejection issued in U.S. Appl. No. 13/110,568; dated Mar. 19, 2012, pp. 1-18.
Non-Final Rejection issued in U.S. Appl. No. 13/467,757; dated Apr. 17, 2013, pp. 1-9.
Feinglos et al., "Effects of liraglutide (NN2211), a long-acting GLP-1 analogue, on glycaemic control and bodyweight in subjects with type 2 diabetes." Diabetic Medicine, 22(8):1016-23 (Jul. 2005).
NCT01146678, ClinicalTrials.gov "Relative Bioavailability and Activity of Different Formulations of Insulin Glargine and Lixisenatide in Patients With Diabetes Mellitus Type 1" last updated Sep. 10, 2010, pp. 1-4.
Non-Final Rejection issued in U.S. Appl. No. 13/700,631; dated Dec. 17, 2015, pp. 1-18.
EMA—Science Medicines Health "TOUJEO" EPAR Summary for the Public, first published Nov. 5, 2009, pp. 1-3.
NHSC—National Horizon Scanning Center, "AVE0010 (ZP10) for type 2 diabetes mellitus" University of Birmingham, England; pp. 1-6 (Dec. 2008).
Non-Final Rejection issued in U.S. Appl. No. 13/509,507; dated Dec. 8, 2015, pp. 1-14.
Non-Final Rejection issued in U.S. Appl. No. 13/819,114; dated Dec. 2, 2015, pp. 1-14.
Search Report of the Intellectual Property Office of Singapore for Patent Application No. 10201500871T, dated Nov. 2, 2015, pp. 1-3.
Nicklas et al.., "Inhibition of NADH-Linked Oxidation in Brain Mitochondria by 1-Methyl-4-Phenyl-Pyridine, a Metabolite of the Neurotoxin, 1-Methyl-4-Phenyl-1,2,5,6-Tetrahydropyridine" Life Sciences 36:2503-508 (1985).
Organization for Economic Co-Ooperation and Development; OECD Principles of Good Laboratory Practice and Compliance Monitoring (as revised in 1997); ENV/MC/Chem (98)17:1-41 (Jan. 21, 1998).
Ott et al., "Diabetes in Germany" (DIG) study. "A prospective 4-year-follow-up study on the quality of treatment for type 2 diabetes in daily practice." Dtsch Med Wochenschr. 134(7):291-7 (2009). English Absract submitted.
Park et al., "PPARalpha agonis fenofibrate improves diabetic nephropathy in db/db mice," Kidney International, 69:1511-17 (published online Mar. 1, 2006).
Parkin "Guideline for Management of Postmeal Glucose" International Diabetes Federation, pp. 1-32 (Oct. 2007).
Patel & Advance Collaborative Group, "Effects of a fixed combination of perindopril and indapamide on macrovascular and microvascular outcomes in patients with type 2 diabetes mellitus (the Advance trial): a randomised controlled trial." Lancet 370(9590):829-40 (2007).
Patel & Borchardt, "Chemical pathways of peptide degradation. II. Kinetics of deamidation of an asparaginyl residue in a model hexapeptide," Pharmaceutical Research 7(7):703-11 (1990).
Perfetti "Combining basal insulin analogs with glucagon-like peptide-1 mimetics." Diabetes Technology & Therapeutics 13(9):873-81 (2011).

(56) References Cited

OTHER PUBLICATIONS

Perry et al., "A novel neurotrophic property of glucagon-like peptide 1: a promoter of nerve cell growth factor mediated differentiation on PC12 cells" J Pharmacol Exp (2002) pp. 958-966, vol. 300.
Perry et al., "Protection and reversal of excitotoxic neuronal damage by glucagon-like peptide-1 and exendin-4" J Pharmacol Exp Ther (2002) pp. 881-888, vol. 302.
Perry et al., "Evidence of GLP-1-mediated neuroprotection in an animal model of pyridoxine-induced peripheral sensory neuropathy" Exp Neural (2007) pp. 293-301, vol. 203, No. 2.
Perry et al., "The glucagon-like peptides: a double-edged therapeutic sword" Trends in Pharmacological Sciences (2003) pp. 377-383, vol. 24.
Perry et al., "A new Alzheimer's disease interventive strategy: GLP-1." Current Drug Targets;5(6):565-71 (Aug. 2004).
Pinget et al., "Efficacy and Safety of Lixisenatide Once Daily Versus Placebo in Patients With Type 2 Diabetes Insufficiently Controlled on Pioglitazone (GetGoal-P)" Diabetes, 61(Supp 1):A258, Poster 1010-P (Jun. 2012).
Pi-Sunyer et al., "The effects of pharmacologic agents for type 2 diabetes mellitus on body weight". Postgrad Med. 120(2):5-17 (Jul. 2008).
Porter et al., "Four weeks administration of Liraglutide improves memory and learning as well as glycemic control in mice with high fat dietary-induced obesity and insulin resistance" Diab Obes Metab (2010) pp. 891-899.
Pradier L et al. "Animal Models of Alzheimer's disease." Demences (Dementias); eds. Duyckaerts C. and Pasquier F.; publisher Doin; 165-170 (Sep. 10, 2002; available Aug. 27, 2002).
Prandini "Methods of measuring gallbladder motor functions—the need for standardization: scintigraphy." Dig Liver Dis. 35 Suppl 3:S62-6 (2003).
"Preferable." Merriam-Webster.com. Merriam-Webster, n. d. Web. Sep. 7, 2015. http://www.merriamwebster.com/dictionary/preferable).
Pugeat et al., "Insulin Resistance, Polycystic Ovary Syndrome and Metformin" Review Article, Drugs 1999; 58(Suppl 1):41-46 (Sep. 1999).
Quianzon & Shomali, "Lixisentide—Once Daily Glucagon-like Peptide-1 receptor Agonist in the Management of Type 2 Diabetes", US Endocrinology, 7(2):104-9 (Winter 2011).
Raccah et al., "When Basal Insulin Therapy in Type 2 Diabetes Mellitus is Not Enough—What Next?" Diabetes Metabolism Research and Reviews 23:257-64 (published online Feb. 21, 2007).
Ramos et al., "Early neuropathology of somatostatin/NPY GABAergic cells in the hippocampus of a PS1×App transgenic model of Alzheimer's disease" Neurobiology of Aging, 27:1658-1672 (2006).
Rao et al., "Is the combination of sulfonylureas and metformin associated with an increased risk of cardiovascular disease or all-cause mortality? A meta-analysis of observational studies." Diabetes Care. 31(8):1672-8 (2008).
Raju et al., "Optimum Palliation of Inoperable Hilar Cholangiocarcinoma: Comparative Assessment of the Efficacy of Plastic and Self-Expanding Metal Stents," Dig Dis Sci. 56:1557-64 (published online, Jan. 11, 2011).
Ratner et al. Abstract 131 "Post-meal pharmacodynamics profile of AVE0010, a once-daily GLP-1 receptor agonist, in patiens with type 2 diabetes inadequately controlled on metformin" Diabetologia 52(Suppl. 1): S60, #131 (Sep. 2009).
Ratner et al. "Dose-dependent effects of the once-daily GLP-1 receptor agonist lixisenatide in patients with Type 2 diabetes inadequately controlled with metformin: a randomized double-blind, placebo-controlled trial," Diabetic Med. 27 (9):1024-1032 (Sep. 2010).
Ratner et al., Poster "A dose-finding study of the new GLP-1 agonist AVE0010 in Type 2 Diabetes insufficiently controlled with metformin.", Diabetes, 57:Suppl.1, A129, Abstract No. 433-P, 68th Annual Meeting of the American Diabetes Association, San Francisco, Jun. 6-10, 2008.
Request for "Type C" Meeting letter sent by Michael Lutz addressed to Mary Parks, dated Apr. 21, 2006, pp. 1-10.
Richter, von Margret, "Oldtimer as Newcomer" Pharmazie, pp. 1-9; http://www.pharmazeutische-zeitung.de/pza/2002-12/pharm1.htm (Feb. 2002), siguanide.
Riddle et al., Contributions of Basal and Postprandial Hyperglycemia Over a Wide Range of A 1 C Levels Before and After Treatment Intensification in Type 2 Diabetes, Diabetes Care 34:2508-2514 (published online Oct. 25, 2011).
Riddle et al., Adding once-daily Lixisenatide for Type 2 Diabetes inadequately controlled by established basal insulin: a 24-week, randomized, placebo-controlled comparison (GetGoal-L). Diabetes Care 36(9):2489-96 (Sep. 2013).
Riddle et al., "Adding Once-Daily Lixisenatide for Type 2 Diabetes Inadequately Controlled with Newly Initiated and Continuously Titrated Basal Insulin Glargine" Diabetes Care, pp. 2497-2503 (Sep. 2013).
Rohrmann, "Differential Diagnosis of Pancreatic and Biliary Duct Diseases," Diseases of the Abdomen and Pelvis Syllabus, pp. 170-174 (1999).
Rosenstock et al., Poster "Efficacy and safety of lixisenatide once daily vs exenatiide twice daily in type 2 DM inadequately controlled on metformin (GetGoal-X)." 71st Scientific Sessions (Nov. 2011).
Rosenstock et al., OP 25 GLP-1 Based therapies, Abstract 145 "Dose range effects of the new once daily GLP-1 receptor agonist AVE0010 added to metformin in type 2 diabetes," Diabetologia 51 (Supplement 1):S66 (Sep. 2008).
Rosenstock et al., Abstract, 564P "Post-meal effects of AVE0010, a once-daily GLP-1 receptor agonist, in type 2 diabetes inadequately controlled on metformin," Diabetes 58(Suppl.1):A151-A152 (Jun. 1, 2009).
Rubino et al., "Delayed initiation of subcutaneous insulin therapy after failure of oral glucose-lowering agents in patients with type 2 diabetes: a population-based analysis in the UK." Diabet Med. 24(12):1412-18 (2007).
Sampson et al., "Second symposium on the definition and management of anaphylaxis: summary report—Second National Institute of Allergy and Infectious Disease/Food Allergy and Anaphylaxis Network symposium." Journal of Allergy and Clinical Immunology, 117(2):391-397 (2006).
Sanger et al., The amide groups of insulin, Biochem J. 59(3):509-18 (1955).
Sanofi's Lantus Draft Prescribing Information/Package Insert: "NDA 21-081 Draft package insert" (Sponsor revision #5) Date of submission: Apr. 20, 2000; see http://www.drugbank.ca/system/fds_labels/DB00047.pdf 1265922812; pp. 1-14.
Sanofi Press Release; "Lyxumia (lixisenatide) in Combination with Basal insulin plus Oral Anti-Diabetics Significantly Reduced HbA1c and Post-Prandial Glucose"; Paris, France (Jun. 9, 2012) pp. 1-6.
Sanofi-aventis Press Release, "Once Daily Lixisenatide (AVE 0010) Given as Monotherapy Successfully Meets Phase III Study Endpoints in Diabetes" Paris, France (Apr. 15, 2010) pp. 1-2.
Sanofi Press Release (Peron and Schaeffer), "Sanofi GetGoal Program on Lyxumia®, as an Add-on to Basal Insulin, Shows Significant Positive Phase III Results," Paris, France (May 31, 2011) pp. 1-2.
Sanofi Press release (Peron and Schaeffer); "Sanofi Reports Positive Results for Once-daily Lyxumia® (lixisenatide) in Combination with Lantus® (insulin glargine) in Type 2 Diabetes" Paris, France (Dec. 6, 2011) pp. 1-3.
Sanofi-aventis Press Release (Gabriel), "New Diabetes Compound AVE0010 Showed Clear Dose Response Results With Once-a-Day Injection in Phase IIb Study" Paris, France (Jun. 7, 2008) pp. 1-2.
Sanofi-aventis Press Release (Peron and Schaeffer), "Sanofi-aventis Announces Positive Top-line Lixisentatide Phase III Results" Paris, France (Feb. 2, 2011) pp. 1-2.

(56) References Cited

OTHER PUBLICATIONS

Sanofi Press Release (Peron and Schaeffer), "Lyxumia® (lixisenatide) One-Step Regimen as Effective as Two-Step Regimen in Improving Glycemic Control in Type 2 Diabetes" Paris, France (Sep. 12, 2011) pp. 1-3.
Sanofi Press Release (Sigurd), "Lixisenatide Significantly Reduces HbA1c Without Increasing Hypoglycemia in Patients Uncontrolled on Sulfonylureas", Pressmeddelande (Apr. 12, 2011) pp. 1-2.
Sanofi and Zealand Pharma Press Release (Evaluate), "Additional Positive Results from Global Phase III Program With Lixisenatide for Type 2 Diabetes", (Apr. 12, 2011) pp. 1-3.
WHO Rational Use of Medicines,http://www.who.int/medicines/areas/rational_use/en/downloaded Dec. 18, 2014 10:02:48 AM (2012).
Widjaja et al., "UKPDS 20: plasma leptin, obesity, and plasma insulin in type 2 diabetic subjects." J Clin Endocrinol Metab. 82(2):654-7 (1997).
Wiernsperger, et al. "The Antihyperglycaemic Effect of Metformin Therapeutic and Cellular Mechanisms" Review Article, Drugs 1999:58(Suppl 1):31-39 (Sep. 1999).
Wirths et al., "Intraneuronal APP/Aβ Trafficking and Plaque Formation in β-Amyloid Precursor Protein and Presenilin-1 Transgenic Mice" Brain Pathol. 12:275-286 (2002).
Wirths et al., "Reelin in plaques of beta-amyloid precursor protein and presenilin-1 double-transgenic mice." Neurosci Lett. 316(3):145-48 (2001).
Wirths et al., "Intraneuronal Abeta accumulation precedes plaque formation in beta-amyloid precursor protein and presenilin-1 double-transgenic mice." Neurosci Lett. 306(1-2):116-20 (2001).
Wollen, Alzheimer's disease: the pros and cons of pharmaceutical, nutritional, botanical, and stimulatory therapies, with a discussion of treatment strategies from the perspective of patients and practitioners, Altern Med. Rev., 15:223-44 (2010).
Yki-Jarvinen et al., "Insulin glargine or NPH combined with metformin in type 2 diabetes: the LANMET study." Diabetologia 49(3):442-51 (Mar. 2006).
Yki-Jarvin et al., "Thiazolidinediones," N Engl J Med. 351(11):1106-18 (Sep. 2004).
Yoon et al., "Exenatide added to insulin therapy: a retrospective review of clinical practice over two years in an academic endocrinology outpatient setting." Clinical Therapeutics 31(7):1511-23 (2009).
Ziemer et al., "Clinical inertia contributes to poor diabetes control in a primary care setting" The Diabetes Educ 31 (4):564-71 (2005).
Ziessman et al., "Sincalide-stimulated cholescintigraphy: a multicenter investigation to determine optimal infusion methodology and gallbladder ejection fraction normal values." J Nucl Med. 51(2):277-81 (Feb. 2010).
Zimmet, et al. "Clinical Efficacy of Metformin against Insulin Resistance Parameters, Sinking the Iceberg" Review Article, Drugs 1999: 58(Suppl 1):21-28 (Sep. 1999).
Zinman et al., "Efficacy and safety of the human glucagon-like peptide-1 analog liraglutide in combination with metformin and thiazolidinedione in patients with type 2 diabetes (Lead-4 Met+ TZD)." Diabetes Care, 32 (7):1224-30 (Jul. 2009).
Translation of pp. 1109, 1116 and 1117 of "Clinical Effectiveness of Long-Term Administration of Bay g5421 (Acarbose) on Insulin-Treated Diabetes," Jpn. Pharmacal. Ther; 1996 vol. 24 No. 5: 1109-1129, pp. 1-4.
Translation of pp. 2346 and 2348 of Rinsho to Kenkyu, "Effectiveness of Combination Therapy Using Voglibose and Insulin in Patients with NIDDM," 1997, vol. 74, No. 9: 2346-2352, pp. 1-3.
Translation of pp. 121 and 124 of Igaku to Yakugaku, "Utility of Voglibose Long-term Combined Therapy in Non-Insulin Dependent Diabtetic Patients with Little Effective of Sulfonylureas," 1999, vol. 42, No. 1: 121-129, pp. 1-3.
Translation of pp. 750, 753 and 754 of Igaku No Ayumi, "Incretin Receptors," 2010, May, vol. 233; No. 9: 750-754, pp. 1-4.
Aoki et al., Hydrolysis of Nonionic Surfactants, Ann. Rept. Takeda Res. Lab. 27, 172-176 (1968).
Bolli "The pharmacokinetic basis of insulin therapy in diabetes mellitus," Diabetes Research and Clinical Practice, 6 (4):S3-15 (May 1989).
Brange et al., "Monomeric insulins and their experimental and clinical implications," Diabetes Care 13(9):923-45 (Sep. 1990).
Brange et al., "Neutral insulin solutions physically stabilized by addition of Zn2+," Diabetic Medicine 3:532-6 (Nov.-Dec. 1986).
Brange "Galenics of Insulin" 1987, p. 35-36.
Burgermeister et al. "The Isolation of Insulin from the Pancreas," Insulin, Part 2, 1975, p. 715-727.
Burke et al., "Nature of the B10 amino acid residue," Int. J. Peptide Protein Res., 23(4):394-401 (Apr. 1984).
Dixon et al., "Regeneration of Insulin Activity From the Separated and Inactive A and B Chains," Nature, vol. 188, No. 4752 (1960), pp. 721-724.
Drury et al., "Diabetic nephropathy," British Medical Bulletin, vol. 45, No. 1, 1989, pp. 127-147.
Garriques et al., "The Effect of Mutations on the Structure of Insulin Fibrils Studied by Fourier Transform Infrared (FTIR) Spectroscopy and Electron Microscopy," Journal of Pharmaceutical Sciences, 91(12):2473-80 (2002).
Geiger, Chem. Zeitung, 100(3), p. 54-56. (Jan. 1976).
Hinds et al., "Synthesis and characterization of poly(ethylene glycol)-insulin conjugates." Bioconjugate Chem. 11 (2):195-201 (Mar.-Apr. 2000).
Home et al., "Insulin treatment: a decade of change," British Medical Bulletin, 1989, vol. 45, No. 1, pp. 92-110.
Kadima "Role of Metal Ions in the T-to R-Allosteric Transition in the Insulin Hexamer," Biochem. 38(41):13443-53 (Oct. 1999).
Kang et al., "Subcutaneous Insulin Absorption Explained by Insulin's Physicochemical Properties—Evidence from Absorption Studies of Soluble Human Insulin and Insulin Analogues in Humans," Diabetes Care, 14(11):942-48 (Nov. 1991).
Kohner "Diabetic retinopathy," British Medical Bulletin, vol. 45, No. 1, 1989, pp. 148-173.
Lougheed et al., "Physical Stability of Insulin Formulations," Diabetes, 32(5):424-32 (May 1983).
Muller et al., "Insulin Signaling in the Yeast *Saccharomyces cerevisiae*. 1. Stimulation of Glucose Metabolism and Snf 1 Kinase by Human Insulin," Biochemistry, 37(24):8683-95 (Jun. 1998).
Pillion et al., "Dodecylmaltoside-mediated Nasal and Ocular Absorption of Lyspro-Insulin: Independence of Surfactant from Multimer Dissociation," Pharmaceutical Research, 15(10): 1637-39 (Oct. 1998).
Thurow & Geisen, "Stabilisation of dissolved proteins against denaturation at hydrophobic interfaces," Diabetologia, 27(2):212-18 (Aug. 1984).
Volund et al., "In Vitro and in Vivo Potency of Insulin Analogues Designed for Clinical Use," Diab. Med. 8(9):839-47 (Nov. 1991).
Ward "Diabetic neuropathy," British Medical Bulletin, 45(1):111-26 (Jan. 1989).
Zinman "The Physiologic Replacement of Insulin," New England J. Med. 321(6):363-70 (Aug. 1989).
Berger "Towards more physiological insulin therapy in the 1990s—A comment," Diabetes Research and Clinical Practice, 6(4): S25-31 (May 1989).
Hunter et al., "Drugs developed to treat diabetes. Liraglutide and lixisenatide, cross the blood brain barrier and enhance neurogenesis", BMC Neuroscience, (2012) vol. 13, p. 6.
Inpharma, Product News. "AVE0010 set to deliver in type 2 diabetes mellitus," Database Adisnews, retrieved from STN, Jun. 2008, pp. 1-3.
Insulinpraparat Wikipedia, http://de.wikipedia.org/wiki/Insulinpr%C3%A4parat, pp. 1-15 (Feb. 5, 2013).
"Insulin Aspart Injection." Formulated Preparations: Specific Monographs. British Pharmacopoeia 3. pp. 1-3 (2012).
Inzucchi et al. "Management of Hyperglycemia in Type 2 Diabetes: A Patient-Centered Approach" Diabetes Care, 35:1364-79 (Jun. 2012).
Isacson et al., "The glucagon-like peptide 1 receptor agonist exendin-4 improves reference memory performance and decreases immobility in the forced swim test" Eur J Pharmacal (2009) pp. 249-255, vol. 10, No. 650.

(56) References Cited

OTHER PUBLICATIONS

ISPAD, International Diabetes Federation; "Global/IDF/ISPAD Guideline for Diabetes in Childhood and Adolescence," pp. 1-132 (2011).
Jackson et al., "Neutral regular insulin," Diabetes 21(4):235-45 (1972).
Jain, "Barriers to Drug Delivery in Solid Tumors," Scientific American, 271(1):58-65 (Jul. 1994).
Jang et al., "Neuroprotective Effects of *Triticum aestivum* L. against β-Amyloid-induced Cell Death and Memory Impairments" Phytother. Res. 24:76-84 (2010).
Jekel et al., "Use of endoproteinase Lys-C from Lysobacter enzymogenes in protein sequence analysis," Anal Biochem. 134(2):347-54 (1983).
Jendle et al., "Insulin and GLP-1 analog combinations in type 2 diabetes mellitus: a critical review." Expert Opin. Investig. Drugs 21(10):1463-74 (2012).
Jimenez et al., "Inflammatory Response in the Hippocampus of PS1M146L/APP751SL Mouse Model of Alzheimer's Disease: Age-Dependent Switch in the Microglial Phenotype from Alternative to Classic" Neurobiology of Disease, 28 (45):11650-661 (2008).
Johnson et al., "When is a unit of insulin not a unit of insulin? Detemir dosing in type 2 diabetes" 2008. http://professional.diabetes.org/ContenUPosters/2008/p8-LB.pdf.
Jorgensen, K. H., et al., "Five fold increase of insulin concentration delays the absorption of subcutaneously injected human insulin suspension in pigs", Diabetes Research and Clinical Practice, 50:161-167 (2000).
Kaarsholm et al., "Engineering stability of the insulin monomer fold with application to structure-activity relationships," Biochemistry 32(40):10773-8 (1993).
Kaduszkiewicz et al.., "Cholinesterase inhibitors for patients with Alzheimer's disease: systematic review of randomised clinical trials." BMJ 331:321 (2005).
Kaech & Banker, "Culturing hippocampal neurons" Nat Protoc. 1(5):2406-15 (2006).
Kahn et al., "Glycemic durability of rosiglitazone, metformin, or glyburide monotherapy." N Engl J. Med. 355 (23):2427-43 (2006).
Kakhi et al., "Normal values of gallbladder ejection fraction using 99 mTc-sestamibi scintigraphy after a fatty meal formula." J Gastrointestin Liver Dis. 16(2):157-61 (Jun. 2007).
Kamisawa. et al., "Pancreatographic investigation of pancreatic duct system and pancreaticobiliary malformation" J. Anal. 212(2):125-34 (2008).
Kanazawa et al., "Criteria and Classification of Obesity in Japan and Asia-Oceania", Asia Pacific J. Clin Nutr. 11 (Suppl. 7):S732-S737 (Dec. 2002).
Kao et al., "The evaluation of gallbladder function by quantitative radionuclide cholescintigraphy in patients with noninsulin-dependent diabetes mellitus." Nucl. Med Commun.14(10):868-72 (1993).
Kapitza et al., Abstract "Pharmacodynamic Characteristics of Lixisenatide QD vs Liraglutide QD in Patients with T2DM Inadequately Controlled with Metformin" Abtract D-0740, presented at the World Diabetes Congress in Dubai, Dec. 5-8, 2011, one page.
Kastin et al., "Interactions of Glucagon-like peptide (GLP-1) with blood brain barrier" Journal of Molecular Neuroscience (2001) pp. 7-14, vol. 18, No. 2.
Kastin et al., "Entry of exedin-4 into brain is rapid but may be limited at high doses" International Journal of Obesity and Related Metabolic Disorders: Journal of the International Association for the Study of Obesity (2003) vol. 27 No. 3, pp. 313-318.
Kemmler et al., "Studies on the Conversion of Proinsulin to Insulin," The Journal of Biological Chemistry, 246 (22):6786-91 (1971).
Kendall et al., "Effets of Exenatide (Exendin-4) on Glycemic Control Over 30 Weeks in Patients With Type 2 Diabetes Treated With Metformin and a Sulfonylurea" Diabetes Care 28:1083-91 (May 2005).

Kielgast et al., "Treatment of type 1 diabetic patients with glucagon-like peptide-1 (GLP-1) and GLP-1R agonists." Curr Diabetes Rev. 5(4):266-75 (Nov. 2009).
Kim et al, "Exendin-4 protects dopaminergic neurons by inhibition of microglial activation and matrix metalloproteinase-3 expression in an animal model of Parkinson's disease," J. Endocrin. 202:431-439 (2009).
Knee et al., "A Novel Use of U-500 Insulin for Continuous Subcutaneous Insulin Infusion in Patients With Insulin Resistance: A Case Series", Endocrine Practice, 9(3):181-86 (May/Jun. 2003).
Kohn et al., "pi-shifted insulin analogs with extended in vivo time action and favorable receptor selectivity," Peptide 28:935-48 (2007).
Korczyn and Nussbaum, "Emerging Therapies in the Pharmacological Treatment of Parkinson's Disease," Drugs 62:775-766 (2002).
Krishnamurthy et al., Constancy and variability of gallbladder ejection fraction: impact on diagnosis and therapy. J Nucl Med. 45(11):1872-77 (Nov. 2004).
Lando, "The New 'Designer' Insulins", Clinical Diabetes, 18(4): Fall 2000 (http://journal.diabetes.org/clinicaldiabelesN18N42000/pg154.hlm; accessed Oct. 22, 2013, pp. 1-13).
Langston et al., "Chronic Parkinsonism in Humans Due to a Product of Meperedine-Analog Synthesis" Science 219 (4587):979-80 (1983).
Langui et al., "Subcellular Topography of Neuronal Aβ Peptide in APPxPS1 Transgenic Mice" American Journal of Pathology 165(5):1465-77 (2004).
Lantus® ANNEX I—Summary of product characteristics. Date of first authorisation: Jun. 9, 2000, pp. 1-164.
Lantus® Product Information—European Medicines Agency, first published Aug. 5, 2009, pp. 1-2.
Larsen et al., "Combination of the insulin sensitizer, pioglitazone, and the long-acting GLP-1 human analog, liraglutide, exerts potent synergistic glucose-lowering efficacy in severely diabetic ZDF rats," Diabetes, Obesity and Metabolism, 10:301-311 (2008).
Lee et al., "Ischemia-induced changes in glucagon-like peptide-1 receptor and neuroprotective effect of its agonist exendin-4, in experimental transient cerebral ischemia" J Neurosc Res (2009) pp. 1103-1113, vol. 89.
Lens, "The terminal carboxyl groups of insulin," Biochimica et Biophysica Acta 3:367-70 (1949).
Levene & Simms, "Calculation of isoelectric point," J Biol Chern. 55:801-13 (1923).
Levin et al., "Combination therapy with insulin glargine and exenatide: real-world outcomes in patients with type 2 diabetes." Current Medical Research & Opinion 28(2):1-8 (2012).
Leyer et al., "The role of the C-terminus of the insulin B-chain in modulating structural and functional properties of the hormone," Int J Pep Protein Res. 46(5):397-407 (1995).
Levine et al., "Oxidation of Methionine in Proteins: Roles in Antioxidant Defense and Cellular Regulation" IUBMB Life, 50:301-07 (Oct. 2000).
Li et al., "Chronic treatment of exendin-4 affects cell proliferation and neuroblast differentiation in the adult mouse hippocampal dentate gyrus." Neurosci Lett 19:1205-19 (2010).
Li et al., "GLP-1 Receptor Stimulation Reduces Amyloid-beta Peptide Accumulation and Cytotoxicity in Cellular and Animal Models of Alzheimer's Disease" J Alzheimers Dis (2010) pp. 1205-1219, vol. 19.
Li et al., "GLP-1 receptor stimulation preserves primary cortical and dopaminergic neurons in cellular and rodent models of stroke and Parkinsons" PNAS (2009) pp. 1285-1290, vol. 106, No. 4.
Li et al., "Enhancing the GLP-1 receptor signaling pathway leads to proliferation and neuroprotection in human neuroblastoma cells" Journal of Neurochemistry, 113:1621-631 (2010).
Actrapid® summary of product characteristics, Apr. 2011, pp. 1-11.
Actrapid® prescribing information, Apr. 2011, pp. 1-4.
Apidra® prescribing information, Apr. 2012, pp. 1-6.
Berlinsulin® H summary of product characteristics, Apr. 2012, pp. 1-11.
Berlinsulin® H prescribing information, Apr. 2012, pp. 1-4.
Humalog® prescribing information, Apr. 2012, pp. 1-6.

(56) References Cited

OTHER PUBLICATIONS

Insuman® Comb25 prescribing information, Feb. 2011, pp. 1-4.
Insuman® Infusat prescribing information, Feb. 2011, pp. 1-4.
Lantus® prescribing information, May 2012, pp. 1-6.
Levemir® prescribing information, Dec. 2011, pp. 1-6.
Novolog® product information, Oct. 2009, pp. 1-4.
NovoMix® prescribing information, Feb. 2011, pp. 1-5.
NovoRapid® prescribing infonnation, Jul. 2012, pp. 1-5.
Fonseca et al., "Efficacy and Safety of the Once-Daily GLP-1 Receptor Agonist Lixisenatide in Monotherapy" Diabetes Care, 35:1225-31 (Jun. 2012).
Fox et al., "Single amino acid substitutions on the surface of *Escherichia coli* maltose-binding protein can have a profound impact on the solubility of fusion proteins," Protein Science 10: 622-30 (2001).
Fransson et al., "Oxidation of Human Insulin-Like Growth Factor I in Formulation Studies: Kinetics of Methionine Oxidation in Aqueous Solution and in Solid State" Pharmaceutical Research 13(8):1252-57 (Aug. 1996).
Galloway & Root, "New forms of insulin," Diabetes 21 (2 Suppl):637-48 (1972).
Gallwitz, "Liraglutide. GLP-1 Receptor Agonist Treatment of Type 2 Diabetes Treatment of Obesity," Drugs of the Future, 33(1):13-20 (Jan. 2008).
Gandhi & Wood, "Molecular pathogenesis of Parkinson's disease." Hum Mol Genet 14:2749-55 (2005).
Garber et al., "Liraglutide versus glimepiride monotherapy for type 2 diabetes (Lead-3 Mono): a randomised, 52-week, phase III, double blind, parallel-treatment trial", The Lancet, 373(9662):473-81 (Feb. 7, 2009).
Garg, R., et al., "U-500 insulin: why, when and how to use in clinical practice", Diabetes/Metabolism Research and Reviews, 23:265-268 (2007).
Gault et al. "GLP-1 agonists facilitate hippocampal L TP and reverse the impairment oiL TP induced by beta-amyloid." Eur J Pharmacal; 587(1-3):112-7 (Jun. 10, 2008; published online Mar. 29, 2008).
Gavin—Committee Report, "Report of the Expert Committee on the Diagnosis and Classification of Diabetes Mellitus," Diabetes Care, 20(7):1183-97 (Jul. 1997).
Gengler et al., "Vai(8)GLP-1 rescues synaptic plasticity and reduces dense core plaques in APP/PS1 mice" Neurobiol Aging (2012) pp. 265-276, vol. 33.
Gerich et al., "Monotherapy with GLP-1 receptor agonist, Lixisenatide, significantly improves glycaemic control in type 2 diabetic patients," Presentation abstract 830, 46th Annual Meeting of EASD, Stockholm, Sweden, pp. 1-3 (Sep. 2010).
Giugliano et al., "Treatment regimens with insulin analogues and haemoglobin A1c target of <7% in type 2 diabetes: A systematic review." Diabetes Research and Clinical Practice 92(1):1-10 (2010).
Goldstein et al.. Tests of Glycemia in Diabetes. Diabetes Care 18(6):896-909 (Jun. 1995).
Gough, K. et al.; Assessment of Dose Proportionality: Report from the Statisticians in the Pharmaceutical Industry/Pharmacokinetics UK Joint Working Party; Drug Information Journal, vol. 29, 1995, pp. 1039-1048.
Goykhman et al., "Insulin Glargine: a review 8 years after its introduction." Expert Opin. Pharmacother. 10(4):705-18 (2009).
Gura, "Systems for Identifying New Drugs are Often Faulty," Science, 278(5340):1041-042 (1997).
Hamilton et al., "Novel GLP-1 mimetics developed to treat type 2 diabetes promote progenitor cell proliferation in the brain" J Neurosci Res (2011) pp. 481-489, vol. 89.
Hamilton et al., "Receptors for the incretin glucagon-like peptide-1 are expressed on neurons in the central nervous system" NeuroReport(2009) vol. 20 No. 13, pp. 1161-1166.
Hanas et al., "2010 Consensus Statement on the Worldwide Standardization of the Hemoglobin A1C Measurement." Diabetes Care 33(8):1903-04 (Aug. 2010).

Hanefeld & Temelkova-Kurktschiev, "The postprandial state and the risk of atherosclerosis." Diabet Med. 14 Suppl 3:S6-11 (1997).
Hanefeld M. Normnahe postprandiale Hyperglykamie-eine essenzielle Komponente guter Diabeteskontrolle und Pravention kardiovaskularer Erkrankungen (Near-normal postprandial hyperglycemia—an essential component of good diabetes control and prevention of cardiovascular diseases). Paul Langerhans lecture 2007. Diabetologie und Stoffwechsel 2007; 2:362-369. in German with English abstract.
Hanna et al., Canadian Diabetes Association Clinical Practice Guidelines Expert Committee "Pharmacologic Management of Type 2 Diabetes" Canadian Journal of Diabetes, 27(Supp 2):S37-S42 (Dec. 2003).
Harris "Clinical inertia in patients with T2DM requiring insulin in family practice." Can Earn Physician.56(12):e418-e424 (2010).
Harkavyi et al., "Glucagon-like peptide I receptor stimulation reverses key deficits in distinct rodent models of Parkinson's disease" J Neuroinftamm (2008) pp. 1-9, vol. 5, No. 19.
Hartmann et al., "Biological Activity of des-(B26-B30)-Insulinamide and Related Analogues in Rat Hepatocyte Cultures," Diabetologia 32(7):416-20 (1989).
Hellstrom et al., "T1388 GTP-010 As a Therapetuic Tool in IBS Pain Relief: Prospective, Randomized, Palebo-Controlled Study of a GLP-1 Analog", Gastroenterology, 134(4):A-544; Abstract T1388 (Apr. 2008).
Higgins et al., "Oxidative Stress: Emerging Mitochondrial and Cellular Themes and Variations in Neuronal Injury", Journal of Alzheimer's Disease, 20:S453-S473 (2010).
Himeno et al., "Beneficial effects of exendin-4 on experimental polyneuropathy in diabetic mice" Diabetes (2011) pp. 2397-2406, vol. 60.
HOE 901/2004 Study Investigators Group, "Safety and efficacy of insulin glargine (HOE 901) versus NPH insulin in combination with oral treatment in Type 2 diabetic patients," Diabetic Medicine (2003), vol. 20, pp. 545-551, XP002671079.
Holscher "Development of Beta-Amyloid-induced neurodegeneration in Alzheimer's disease and novel neuroprotective strategies," Reviews in Neuroscience, 16:181-212 (2005).
Holscher et al., "New roles for insulin-like hormones in neuronal signaling and protection: new hopes for novel treatments of Alzheimer's disease?" Neuro. Aging 31:1495-1502 (2008).
Holscher "The role of GLP-1 in neuronal activity and neurodegeneration" Vitamins and hormones 84:331-54 (2010).
Holscher "Incretin Analogues that have been Developed to Treat Type 2 Diabetes Hold Promise as a Novel Treatment Strategy for Alzheimer's Disease" Recent Patents on Cns Drug Discovery (2010) vol. 5 No. 2, pp. 109-117.
Holscher "Possible Causes of Alzheimer's Disease: Amyloid Fragments, Free Radical, and Calcium Homeostasis" Neurobiology of Disease 5:129-41 (1998).
Holst & Vilsboll. "Combining GLP-1 receptor agonists with insulin: therapeutic rationales and clinical findings." Diabetes, Obesity and Metabolism 15(1):3-14 (2013).
Holman et al., "10-Year Follow-up of Intensive Glucose Control in Type 2 Diabetes." N Engl J. Med. 359(15):1577-89 (2008).
Non-Final Rejection issued in U.S. Appl. No. 13/310,118, dated Mar. 25, 2015, pp. 1-15.
Non-Final Rejection issued in U.S. Appl. No. 13/310,118, dated Mar. 29, 2013, pp. 1-21.
Final Rejection issued in U.S. Appl. No. 13/310,118; dated Aug. 2, 2012, pp. 1-20.
Non-Final Rejection issued in U.S. Appl. No. 13/310,118; dated Mar. 19, 2012, pp. 1-19.
Non-Final Rejection issued in U.S. Appl. No. 13/595,590; dated Jun. 5, 2015, pp. 1-9.
Final Rejection issued in U.S. Appl. No. 13/595,590; dated Dec. 19, 2014, pp. 1-14.
Non-Final Rejection issued in U.S. Appl. No. 13/595,590; dated Sep. 5, 2014, pp. 1-10.
Final Rejection issued in U.S. Appl. No. 13/595,590; dated Apr. 2, 2014, pp. 1-7.
Non-Final Rejection issued in U.S. Appl. No. 13/595,590; dated Oct. 16, 2013, pp. 1-7.

(56) References Cited

OTHER PUBLICATIONS

Final Office Action issued in U.S. Appl. No. 13/602,913; dated Apr. 2, 2015, pp. 1-7.
Non-Final Office Action issued in U.S. Appl. No. 13/602,913; dated Dec. 2, 2014, pp. 1-12.
Final Office Action issued in U.S. Appl. No. 13/602,913; dated Jun. 20, 2014, pp. 1-27.
Non-Final Office Action issued in U.S. Appl. No. 13/602,913; dated Jan. 13, 2014, pp. 1-53.
Final Office Action issued in U.S. Appl. No. 13/602,913; dated Sep. 13, 2013, pp. 1-11.
Non-Final Office Action issued in U.S. Appl. No. 13/602,913; dated May 17, 2013, pp. 1-7.
Non-Final Rejection in U.S. Appl. No. 13/633,563; dated Jul. 1, 2013, pp. 1-56.
Final Rejection in U.S. Appl. No. 13/633,563; dated Dec. 16, 2013, pp. 1-58.
Non-Final Rejection in U.S. Appl. No. 13/633,563; dated Jun. 4, 2014, pp. 1-11.
Non-Final Rejection in U.S. Appl. No. 13/633,563; dated Dec. 1, 2014, pp. 1-9.
Final Rejection in U.S. Appl. No. 13/633,563; dated Apr. 22, 2015, pp. 1-12.
Non-Final Rejection in U.S. Appl. No. 13/633,496; dated Apr. 29, 2013, pp. 1-53.
Final Rejection in U.S. Appl. No. 13/633,496; dated Nov. 4, 2013, pp. 1-7.
Non-Final Rejection in U.S. Appl. No. 13/633,496; dated May 22, 2014, pp. 1-11.
Final Rejection in U.S. Appl. No. 13/633,496; dated Nov. 18, 2014, pp. 1-11.
Non-Final Rejection in U.S. Appl. No. 13/633,496; dated Apr. 6, 2015, pp. 1-14.
Non-Final Rejection issued in U.S. Appl. No. 13/468,422; dated Mar. 27, 2013, pp. 1-27.
Non-Final Rejection issued in U.S. Appl. No. 13/468,422; dated Sep. 16, 2013, pp. 1-19.
Final Rejection issued in U.S. Appl. No. 13/468,422; dated Jan. 6, 2014, pp. 1-21.
Non-Final Rejection issued in U.S. Appl. No. 13/468,422; dated Jun. 4, 2014, pp. 1-24.
Final Rejection issued in U.S. Appl. No. 13/468,422; dated Jan. 23, 2015, pp. 1-27.
Non-Final Rejection issued in U.S. Appl. No. 13/468,422; dated Nov. 4, 2015; pp. 1-27.
Non-Final Rejection issued in U.S. Appl. No. 13/661,476; dated Jun. 4, 2015, pp. 1-31.
Final Rejection issued in U.S. Appl. No. 13/661,476, dated Oct. 2, 2014, pp. 1-33.
Non-Final Rejection issued in U.S. Appl. No. 13/661,476, dated Mar. 6, 2014, pp. 1-28.
Non-Final Rejection issued in U.S. Appl. No. 13/661,476, dated Dec. 4, 2013, pp. 1-11.
Non-Final Rejection issued in U.S. Appl. No. 13/661,476, dated Sep. 16, 2013, pp. 1-19.
Non-Final Rejection issued in U.S. Appl. No. 13/692,640; dated Oct. 31, 2013, pp. 1-10.
Non-Final Rejection issued in U.S. Appl. No. 13/692,640; dated May 6, 2014, pp. 1-10.
Final Rejection issued in U.S. Appl. No. 13/692,640; dated Jan. 6, 2015, pp. 1-11.
Final Rejection issued in U.S. Appl. No. 13/692,640; dated Jun. 2, 2015, pp. 1-12.
Non-Final Rejection issued in U.S. Appl. No. 14/303,895; dated May 21, 2015, pp. 1-11.
International Search Report by the ISA for International Application No. PCT/EP2007/005932; dated Oct. 9, 2007, pp. 1-6.
International Search Report by the ISA for International Application No. PCT/EP2009/000017; dated Jun. 22, 2009, pp. 1-7.
International Search Report by the ISA for International Application No. PCT/EP2009/063195; dated May 6, 2010.
International Search Report by the ISA for International Application No. PCT/EP2010/059436; dated Jun. 17, 2011, pp. 1-5.
International Search Report by the ISA for International Application No. PCT/EP2010/059438; dated Oct. 4, 2010, pp. 1-3.
International Search Report by the ISA for International Application No. PCT/EP2010/062638; dated Mar. 18, 2011, pp 1-5.
International Search Report by the ISA for International Application No. PCT/EP2010/067250; dated Mar. 23, 2011, pp. 1-3.
International Search Report by the ISA for International Application No. PCT/EP2011/058079; dated Mar. 22, 2012, pp. 1-6.
International Search Report by the ISA for International Application No. PCT/EP2011/058764; dated Jun. 30, 2011, pp. 1-9.
U.S. Appl. No. 14/965,586, filed Dec. 10, 2015, Souhami et al.
U.S. Appl. No. 14/995,910, filed Jan. 14, 2016, Bergmann et al.
American Diabetes Association, "Type 2 diabetes in children and adolescents." Diabetes Care 23(3):381-89 (Mar. 2000).
Ahualli "The Double Duct Sign" Radiology 244(1):314-5 (Jul. 2007).
Aquiliante, "Sulfonylurea pharmacogenomics in type 2 diabetes: the influence of drug target and diabetes risk polymorphisms" Expert Rev Cardiovasc Ther. 8(3):359-72 (Mar. 2010).
Canadian Diabetes Association. Clinical Practice Guidelines Expert Committee. Canadian Diabetes Association 2008. Clinical Practice Guidelines for the Prevention and Management of Diabetes in Canada. Canadian Journal of Diabetes S162-S167 (2008).
Centers for Disease Control and Prevention. National diabetes fact sheet: general information and national estimates on diabetes in the United States, 2003. Rev ed. Atlanta, GA: U.S. Department of Health and Human Services, Centers for Disease Control and Prevention, pp. 1-8, 2004.
Chi et al., "Excipients and their Effects on the Quality of Biologics" pp. 1-9, (May 2012).
Definition of indication, Merriam-Webster online, accessed Oct. 22, 2015, 2 pages.
Druet et al., "Characterization of insulin secretion and resistance in type 2 diabetes of adolescents." J Clin Endocrinol Metab 91(2):401-404 (Feb. 2006; epub Nov. 15, 2005).
European Medicines Agency, "Toujeo (previously Optisulin) insulin glargine," <http://www.ema.europa.eu/ema/index.jsp?curl=pages/medicines/human/medicines/000309/human_med_000955.jsp&mid=WCOb01ac058001d124>, last updated Jan. 25, 2016, visited Feb. 3, 2016, pp. 1-6—screenshot of "About" tab of webpage and printouts of "About" tab of webpage with listed items collapsed and expanded.
Gygi et al., "Quantitative analysis of complex protein mixtures using isotope-coded affinity tags." Nat Biotechnol. 17 (10):994-99 (Oct. 1999).
IDF Clinical Guidelines Task Force. Global guideline for Type 2 diabetes. Brussels: International Diabetes Federation, pp. 1-82 (Aug. 2005).
Jones et al., "Effect of metformin in pediatric patients with type 2 diabetes: a randomized controlled trial." Diabetes Care 25(1):89-94 (Jan. 2002).
Kim et al., "Retinopathy in Monkeys with Spontaneous Type 2 Diabetes" Investigative Opth & Visual Science, 45 (12):4543-53 (Dec. 2004).
Lursen et al., "Enhanced monitoring of biopharmaceutical product purity using liquid chromatography-mass spectrometry." 1218(28):4340-48 (Jul. 2011; Epub May 2011).
Leib et al., "Direct quantitation of peptide mixtures without standards using clusters formed by electrospray ionization mass spectrometry." Anal Chem. 81(10):3965-72 (May 2009).
Nathan et al., "Medical Management of Hyperglycemia in Type 2 Diabetes: A Consensus Algorithm for the Initiation and Adjustment of Therapy" Diabetes Care 32(1):193-203 (Jan. 2009).
NCT00866658 ClinicalTrials.gov, "GLP-1 agonist AVE0010 in patients with type 2 diabetes for glycemic control and safety evaluation, on top of basil insulin +/-sulfonylurea" p. 1-3, accessed Mar. 16, 2016 (updated Jan. 19, 2010).

(56) References Cited

OTHER PUBLICATIONS

NCT01169779, Clinical Trials.gov, "Efficacy and Safety of Lixisenatide in Patients with Type 2 diabetes mellitus insufficiently controlled by metformin," pp. 1-3, accessed Mar. 16, 2016 (updated Mar. 28, 2011).

NCT00713830, Clinical Trials.gov "GLP-1 Agonist in Patients with Type 2 Diabetes for Glycemic Control and Safety valuation, on Top of Sulfonylurea" pp. 1-3, accessed Mar. 16, 2016 (updated Jul. 13, 2008).

NICE, National Institute for Health and Care Excellence, "Evidence summary: new medicine, ESNM26: Type 2 diabetes: lixisenatide; Key points from the evidence" pp. 1-26 (Sep. 24, 2013).

NIH, National Institute of Diabetes and Digestive and Kidney Disease, "Hypoglycimia" pp. 1-8, accessed Mar. 16, 2016.

Nilsson et al., "Effects of GI vs content of cereal fibre of the evening meal on glucose tolerance at a subsequent standardized breakfast." Eur. J Clin Nutr. 62:712-20 (2008; epub May 23, 2007).

Olansky "Do incretin-based therapies cause acute pancreatitis?" J Diabetes Technol. 4(1):228-29 (Jan. 2010).

Pinhas-Hamiel & Zeitler, "Clinical presentation and treatment of type 2 diabetes in children." Pediatric Diabetes 8 (9):16-27 (Dec. 2007).

Sanofi-aventis Press Release, "A promising R&D portfolio, well positioned to deliver future growth" (dated Sep. 17, 2007) pp. 1-11.

Schwartz et al., "New Equations to Estimate GFR in Children with CKD." J Am Soc Nephrol 20(3):629-37 (Mar. 2009; epub Jan. 21, 2009).

Smolka et al., "Optimization of the isotope-coded affinity tag-labeling procedure for quantitative proteome analysis." Anal Biochem. 297(1):25-31 (Oct. 2001). Abstract only submitted.

Srinivasan & Ramarao, "Animal models in type 2 diabetes research: An overview." Indian J Med Res. 125:451-472 (Mar. 2007).

Tanner et al., "Standards from birth to maturity for height, weight, height velocity, and weight velocity: British children, Part II" Arch Dis Child. 41(220):613-35 (1966).

World Health Organization, "Definition, Diagnosis and Classification of Diabetes Mellitus and its Complications. Part 1: Diagnosis and Classification of Diabetes Mellitus." WHO/NCD/NCS/99.2. Geneva; pp. 1-66, (1999).

Xie et al., "Characterization of protein impurities and site-specific modifications using peptide mapping with liquid chromatography and data independent acquisition mass spectrometry." Anal Chem. 81(14):5699-708 (Jul. 2009).

Non-Final Rejection issued in U.S. Appl. No. 13/382,442; dated Mar. 31, 2016, pp. 1-29.

Final Rejection issued in U.S. Appl. No. 13/382,442; dated Aug. 11, 2015, pp. 1-35.

Final Rejection issued in U.S. Appl. No. 13/382,772; dated Feb. 24, 2016, pp. 1-36.

Non-Final Office Action from U.S. Appl. No. 12/617,805; dated Sep. 15, 2015, pp. 1-12.

Non-Final-Rejection issued in U.S. Appl. No. 13/432,811; dated Sep. 9, 2015, pp. 1-11.

Non-Final Rejection in U.S. Appl. No. 13/633,563; dated Oct. 6, 2015, pp. 1-12.

Non-Final Rejection issued in U.S. Appl. No. 14/303,895; dated Sep. 9, 2015, pp. 1-12.

International Search Report by the ISA for International Application No. PCT/EP2015/079285; dated Mar. 9, 2016, pp. 1-7.

Extended European Search Report for European Application No. 15 15 9064.3; dated Oct. 19, 2015, pp. 1-4.

English Translation of TIPO Search Report for ROC Patent Application No. 101130936, dated Dec. 1, 2015, one page.

English translation of the TIPO Search Report for ROC Patent Application No. 104116749, dated Feb. 22, 2016, one page.

English translation of the TIPO Search Report for ROC Patent Application No. 101131466 dated Mar. 2, 2016, one page.

Final-Rejection issued in U.S. Appl. No. 13/432,811; dated Feb. 10, 2016, pp. 1-9.

Final Rejection issued in U.S. Appl. No. 13/467,707; dated Feb. 12, 2016, pp. 1-12.

UK Prospective Diabetes Study (UKPDS) Group 28: A randomized trial of efficacy of early addition of metformin in sulfonylurea-treated type 2 diabetes. Diabetes Care 1998; 21(1):87-92 (Jan. 1998).

van Gaal et al., "Exploiting the antidiabetic properties of incretins to treat type 2 diabetes mellitus: glucagon-like peptide 1 receptor agonists or insulin for patients with inadequate glycemic control," European Journal of Endocrinology 158(6):773-84 (Jun. 2008).

van Gaal & De Leeuw, "Rationale and options for combination treatment of type 2 diabetes." Diabletologia 46 (Supplement 1):M44-M50 (Mar. 2003).

Wahlin-Boll et al., "Impaired effect of sulfonylurea following increased dosage." Eur J Clin Pharmacol 22(1):21-25 (1982).

Werner, "Preclinical pharmacology of the new GLP-1 receptor agonist AVE0010", Ann. Endocrinol. (Paris), 69 (2):164-65 (Apr. 2008).

Wikipedia® entry for "Stratified sampling" Retrieved on Mar. 28, 2017, pp. 1-4.

Williams, "Macrovascular disease in Diabetes." In handbook of Diabetes. 2nd ed. Williams G, Pickup JC, Eds. Oxford, UK, Blackwell Science Chapter 20; pp. 152-160 (2010).

Yki-Järvinen, "Combination Therapies with insulin in type 2 diabetes." Diabetes Care 24(4):758-67 (Apr. 2001).

Yki-Järvinen et al., "Comparison of Bedtime insulin regimes in patients with type 2 diabetes mellitus." Annals of Internal Medicine 130(5):389-96 (Mar. 1999).

Zinman et al., "The Effect of Adding Exenatide to a Thiazolidinedione in Suboptimally Controlled Type 2 Diabetes" Annals of Internal Medicine, 146(7):477-85 (Apr. 2007).

Definition of "Phase" Clinical Trials.gov NIH, accessed Mar. 16, 2016, one page.

Johnson et al., "Diabetes, Insulin Resistance, and Metabolic Syndrome in Horses" Journal of Diabetes Science and Technology, 6(3):534-40 (May 2012).

Final Rejection issued in U.S. Appl. No. 14/303,895; dated Apr. 27, 2016, pp. 1-10.

Ahmad & Swann, and Bloomgren "Exenatide and rare adverse events." N Engl J Med 358(18):1969-72 (May 2008).

Albert-Ludwigs University Freiburg, Institute fur Medizinische Biometrie and Statistik "Non-Inferiority Trials" dated Mar. 29, 2017, one page.

American Diabetes Association Annual Scientific Sessions, "New Diabetes Compound AVE0010 Showed Clear Dose Response Results With Once-a-Day Injection in Phase IIb Study", published Jun. 9, 2008, two pages.

American Diabetes Association, "Standards of Medical Care in Diabetes." Diabetes Care 28(Supplement 1): S4-S36 (Jan. 2005).

American Diabetes Association, "Standards of Medical Care in Diabetes 2008." Diabetes Care 31(Supplement 1):S12-S54.

Bastyr et al., "Therapy focused on lowering postprandial glucose, not fasting glucose, may be superior for lowering HbA1c. IOEZ Study Group." Diabetes Care 23(9):1236-41 (Sep. 2000).

Bennett, "Impact of the new WHO classification and diagnostic criteria." Diabetes Obes Metab 1(Supplement 2):S1-S6 (1999).

Buse et al., "Effects of exenatide (Exendin-4) on glycemic control over 30 weeks in sulfonylurea-treated patients with type 2 diabetes." Diabetes Care 27(11):2628-35 (Nov. 2004).

BYETTA® Labeling Revision, pp. 1-24 (Jan. 11, 2008).

BYETTA® European Public Assessment Report (EPAR), pp. 1-36 (Feb. 16, 2012).

BYETTA® Prescribing Information, pp. 1-34 (Revised Oct. 2009).

Definition of "prevent" Dictionary.com; last accessed Sep. 29, 2016, pp. 1-6.

Definition of "induce" Dictionary.com; last accessed Sep. 29, 2016, pp. 1-6.

de la Loge et al., "Cross-cultural development and validation of a patient self-administered questionnaire to assess quality of life in upper gastrointestinal disorders: The PAGI-QOL." Quality of Life Research 13(10):1751-62 (Dec. 2004).

(56) References Cited

OTHER PUBLICATIONS

De Venciana et al., "Postprandial versus preprandial blood glucose monitoring in women with gestational diabetes mellitus requiring insulin therapy." N Engl J Med 333(19):1237-41 (Nov. 1995).
Donahue et al., "Postchallenge glucose concentration and coronary heart disease in men of Japanese ancestry. Honolulu Heart Program." Diabetes 36(6):689-92 (Jun. 1987).
Eckert et al., "Assessing the progression of Parkinson's disease: A metabolic network approach," Lancet Neural. 6 (10):926-32 (Oct. 2007).
European Medicines Agency, "Guideline on clinical investigation of medicinal products in the treatment of hypertension" (EMA/238/1995 Rev 3) pp. 1-18 (Nov. 18, 2010).
European Diabetes Policy Group, "A desktop guide to Type 2 diabetes mellitus." Diabetic Medicine 16 (9):716-730 (1999).
Forlenza et al., "Diagnosis and biomarkers of predementia in Alzheimer's disease," BMC Medicine 8:89 pp. 1-14 (Dec. 2010).
Gerich, "Insulin glargine: long-acting basal insulin analog for improved metabolic control." Curr Med Res Opin. 20 (1):31-37 (Jan. 2004).
Groop et al., "Dose-dependent effects on glyburide on insulin secretion and glucose uptake in humans." Diabetes Care 14(8):724-27 (Aug. 1991).
Groop, "Sulfonylureas in NIDDM." Diabetes Care 15(6):737-54 (Jun. 1992).
Halimi, "DPP-4 inhibitors and GLP-1 analogues: for whom? Which place for incretins in the management of type 2 diabetic patients?", Diabetes & Metabolism 34(Supplement 2):S91-S95 (Feb. 2008).
Heine & Dekker, "Beyond postprandial hyperglycemia: metabolic factors associated with cardiovascular disease." Diabetologia 45(4):461-75 (Apr. 2002).
Heine et al., "Exenatide versus insulin glargine in patients with suboptimally controlled type 2 diabetes." Ann Intern Med. 143(8):559-69 (Oct. 2005).
Hillier & Pedula, "Characteristics of an adult population with newly diagnosed Type 2 Diabetes. The relation of obesity and age of onset." Diabetes Care 24(9):1522-27 (Sep. 2001).
Hollander & Kushner, "Type 2 Diabetes Comorbidities and Treatment Challenges: Rationale for DPP4-Inhibitors" Postgraduate Medicine, 122(3):71-80 (May 2010).
Januvia—EPAR Summary for the Public, pp. 1-3 (Aug. 2012).
Karasik et al., "Sitagliptin, a DPP-4 inhibitor for the treatment of patients with type 2 diabetes: a review of recent clinical trials," Current Medical Research and Opinion 24(2):489-96 (Jan. 2008).
Lepore et al., "Pharmacokinetics and pharmacodynamics of subcutaneous injection of long-acting human insulin analog glargine, NPH insulin, and ultralente human insulin and continuous subcutaneous infusion of insulin lispro." Diabetes 49(12):2142-48 (Dec. 2000).
Mac Conell et al., "Exenatide resulted in significantly greater improvements in posprandial glycaemic control compared to sitagliptin," Diabetologia 51(Supplement 1) p. S348, Abstract 872, one page (2008).
Mainous et al., "Impact of the population at risk of diabetes on projections of diabetes burden in the United States: an epidemic on the way." Diabetologia 50(5):934-40 (May 2007; Epub Nov. 21, 2006).
Matthews et al., "Homeostasis model assessment: insulin resistance and β-cell function from fasting plasma glucose and insulin concentrations in man." Diabetologia 28(7):412-419 (Jul. 1985).
Miller et al., "Type 2 diabetes in the child and adolescent", In: Lifshitz F (ed) Pediatric Endocrinology: 5th edition, vol. 1, New York, Marcel Dekker, pp. 169-188 (2007).
Monnier et al., "Contribution of fasting and postprandial plasma glucose increments to the overall diurnal hyperglycemia of type 2 diabetic patients: variations with increasing levels of HbA1c." Diabetes Care 26(3):881-85 (Mar. 2003).
Mudaliar & Edelman, "Insulin therapy in type 2 diabetes." Endocrinol Metab Clin North Am. 30(4):935-82 (Dec. 2001).

Nathan et al., "Medical Management of Hyperglycemia in Type 2 Diabetes: A Consensus Algorithm for the Initiation and Adjustment of Therapy. A Consensus statement of the American Diabetes Association and the European Association for the Study of Diabetes." Diabetes Care 31(1):173-75 (Jan. 2008).
Nathan et al., "Translating the A1c Assay Into Estimated Average Glucose values." Diabetes Care 31(8):1473-78 (Aug. 2008; Epub Jun. 7, 2008).
Nauck et al., "Effects of Glucagon-Like Peptide 1 on Counterregulatory Hormone Responses, Cognitive Functions, and Insulin Secretion during Hyperinsulinemic, Stepped Hypoglycemic Clamp Experiments in Healthy Volunteers." Journal of Clin. Endocrinol.& Metab. 87(3):1239-46 (Mar. 2002).
Nauck et al., "Efficacy and safety of the dipeptidyl peptidase-4 inhibitor, sitagliptin, compared with the sulfonylurea, glipizide, in patients with type 2 diabetes inadequately controlled on metformin alone: a randomized, double-blind, non-inferiority trial," Diabetes, Obesity and Metabolism, 9(2):194-205 (Mar. 2007).
Riddle et al., "The treat-to-target trial: randomized addition of glargine or human NPH insulin to oral therapy of type 2 diabetes patients." Diabetes Care 26(11):3080-86 (Nov. 2003).
Riddle, "Combined Therapy With Insulin Plus Oral Agents: Is There Any Advantage?" Diabetes Care 31(Supplement 2):S125-S130 (Feb. 2008).
Riddle, "Timely initiation of basal insulin." Am J Med 116(Suppl 3A):3S-9S (Feb. 2004).
Sacks et al., "Guidelines and Recommendations for Laboratory Analysis in the Diagnosis and Management of Diabetes Mellitus." Clinical Chemistry 48(3):436-72 (Mar. 2002).
Sanofi Presentation, "Natixis Conference on Diabetes" Pierre Chancel, pp. 1-23, Nov. 8, 2011.
Zealand Pharma Press Release entitled "Sanofi-Aventis finalize phase IIa clinical study with GLP-1 agonist for type 2 diabetes licensed from Zealand Pharma" dated Mar. 3, 2005, one page.
Sloop et al., "Glucagon as a target for the treatment of Type 2 diabetes." Expert Opin Ther Targets. 9(3):593-600 (Jun. 2005).
Spasov & Chepurnova, "Scientific Approaches to Combination Therapy for Type 2 Diabetes Mellitus," Bulletin of Volgograd State Medical University,1(37):8-10 (2011). See English Absract.
Stumvoll et al., "Type 2 diabetes: Principles of pathogenesis and therapy." Lancet 365(9467):1333-46 (Apr. 2005).
U.S. Appl. No. 15/073,364, filed Mar. 17, 2016, Belder et al.
U.S. Appl. No. 15/068,286, filed Mar. 11, 2016, Roy et al.
Seino et al., and the Committee of Japan Diabetes Society on the diagnostic criteria of diabetes mellitus. "Report of the committee on the classification and diagnostic criteria of diabetes mellitus." Journal of the Japan Diabetes Society. 53:450-467 (2010). In Japanese, English translation of selected passages provided.
Ganz et al., "The association of body mass index with the risk of type 2 diabetes: a case-control study nested in an electronic health records system in the United States." Diabetology & Metabolic Syndrome, 6:50, pp. 1-8 (Apr. 2014).
Mokdad et al., "The association of body mass index with the risk of type 2 diabetes: a case-control study nested in an electronic health records system in the United States." JAMA, 289(1):76-79 (Jan. 2003).
Abraira et al., "Glycaemic separation and risk factor control in the Veterans Affairs Diabetes Trial: an interim report" Diabetes Obes Metab 11(2):150-56 (2009; Epub Jul. 29, 2008).
Aguilar, "Heart failure and diabetes: Time to pay attention" American Heart Journal, 162(5):795-97 (Nov. 2011).
American Diabetes Association, "Diagnosis and Classification of Diabetes Mellitus", Diabetes Care, 37 (Supplement 1):S81-S90 (Jan. 2014).
American Diabetes Association, "Standards of Medical Care in Diabetes-2011," Diabetes Care, Jan. 2011, vol. 34 (Suppl 1), pp. S11-S61.
Ampudia-Blasco et al., "Basal Plus Basal-Bolus approach in type 2 diabetes" Diabetes Technol Ther. 13 Suppl1: S75-83 (Jun. 2011).
Atkinson et al., "Validation of a general measure of treatment satisfaction, the Treatment Satisfaction Questionnaire for Medication (TSQM), using a national panel study of chronic disease" Health Qual Life Outcomes, 2:12, pp. 1-13 Feb. 2004).

(56) References Cited

OTHER PUBLICATIONS

Beckman et al., "Diabetes and atherosclerosis: epidemiology, pathophysiology, and management" JAMA 287 (19):2570-81 (May 2002).
Bell G.I., et al., "Sequence of the Human Insulin Gene,"Journal of Nature, 1980, vol. 284 (5751), pp. 26-32.
Bentley-Lewis et al., "Rationale, design, and baseline characteristics in Evaluation of LIXisenatide in Acute Coronary Syndrome, a long-term cardiovascular end point trial of lixisenatide versus placebo" American Heart Journal, 169(5):631-38 (May 2015; Epub Feb. 11, 2015).
Brazier et al., "Testing the validity of the Euroqol and comparing it with the SF-36 health survey questionnaire," Qual Life Res 2(3):169-80 (Jun. 1993).
Byetta® Product information, EMA pp. 1-2, accessed Jun. 10, 2016.
Byetta® Summary of product characteristics, ANNEX I, pp. 1-71, (2011).
Canadian Cardiovascular Society Grading of Angina Pectoris, From http://www.sscts.org/pages/Classificationanginaccs.aspx. Accessed May 27, 2016, one page.
Cannon et al., "Intensive versus Moderate Lipid Lowering with Statins after Acute Coronary Syndromes." New England Journal Medicine, Apr. 2004; Epub Mar. 8, 2004, 2004, vol. 350 (15), pp. 1495-1504.
Classification of Functional Capacity and Objective Assessment, My.AmericanHeart, 1994—last accessed Oct. 23, 2015, pp. 1-2.
Clinical Trials Archive for Trial No. NCT00688701 updated Sep. 30, 2012. Accessed at: https://clinicaltrials.gov/archive/NCT00688701/2012.09.30/changes Accessed on Jun. 2, 2016, pp. 1-5 submitted.
Clinical Trials History for Trial No. NCT00688701 last updated Mar. 25, 2014. Accessed at https://clinicaltrials.gov/archive/NCT00688701 Accessed on Jun. 2, 2016, pp. 1-2 submitted.
Charbonnel et al., "Efficacy and safety of the dipeptidyl peptidase-4 inhibitor sitagliptin added to ongoing metformin therapy in patients with type 2 diabetes inadequately controlled with metformin alone." Diabetes Care 29(12):2638-43 (Dec. 2006).
Coutinho et al., "The relationship between glucose and incident cardiovascular events. A metaregression analysis of published data from 20 studies of 95,783 individuals followed for 12.4 years." Diabetes Care 22(2):233-40 (Feb. 1999).
D'Alessio et al., "The role of dysregulated glucagon secretion in type 2 diabetes" Diabetes, Obesity and Metabolism, 13(Supppl. 1):126-132 (Oct. 2011).
Das et al., "The British Cardiac Society Working Group Definition of Myocardial Infarction: Implications for Practice," Heart, 92(1):21-26, (Jan. 2006; Epub Apr. 14, 2005).
De Lemos et al., "Early intensive vs. a delayed conservative simvastatin strategy in patients with acute coronary Syndromes: phase Z of the A to Z trial." JAMA 292(11):1307-16 (Sep. 2004; Epub Aug. 30, 2004).
Definition of "Combination", Concise Oxford English Dictionary, edited by A. Stevenson and M. Waite, Oxford University press, 12th Edition, Aug. 2011, 4 pages submitted, see p. 285.
Degn et al., "Effect of Intravenous Infusion of Exenatide (Synthetic Exendin-4) on Glucose-Dependent Insulin Secretion and Counterregulation During Hypoglycemia." Diabetes 53(9):2397-2403 (Sep. 2004).
Del Prato & Tiengo, The importance of first-phase insulin secretion: implications for the therapy of type 2 diabetes mellitus. Diabetes Metab Res. Rev. 17(3):164-74 (May-Jun. 2001).
Del Prato et al., "Global Partnership for Effective Diabetes Management Tailoring treatment to the individual in type 2 diabetes practical guidance from the Global partnership for effective diabetes management" Int J Clin Pract 64 (3):295-304 (Feb. 2010).
DeWITT & Hirsch, "Outpatient insulin therapy in type 1 and type 2 diabetes mellitus: scientific review." JAMA 289 17):2254-64 (May 2003).
Diabetes Control and Complications Trial, Epidemiology of Diabetes Interventions and Complications Research Group, "Intensive Diabetes Treatment and Cardiovascular Disease in Patients with Type 1 Diabetes," New England Journal Medicine, Dec. 2005, vol. 353 (25), pp. 2643-2259.
Diabetes Control and Complications Trial, "Intensive diabetes therapy and carotid intima-media thickness in type 1 diabetes," New England Journal Medicine, Jun. 2003, vol. 348 (23), pp. 2294-2303.
Dinneen & Gerstein, "The association of microalbuminuria and mortality in non-insulin dependent diabetes mellitus. A systematic overview of the literature." Arch Intern Med 157(13):1413-8 (Jul. 1997).
Dolan, "Modeling valuations for EuroQol health states." Med Care 35(11):1095-1108 (Nov. 1997).
Dombrowsky & Barrett, "Type II diabetes mellitus in children: Analysis of prevalence based on the pediatric heath information system (PHIS) database" American College of Clinical Pharmacology Annual Meeting, Bethesda, Maryland (Sep. 22-24, 2013).
Dunning & Gerich, "The Role of alpha-cell Dysregulation in Fasting and Postprandial Hyperglycemia in Type 2 Diabetes and Therapeutic Implications" Endocrine Reviews 28(3):253-83 (Apr. 2007).
European Medicines Agency, "Note for guidance on non-clinical safety studies for the conduct of human clinical Trials and marketing authorization for pharmaceuticals," Jul. 2008, pp. 1-22.
Encyclopedia of Drugs, "Metformin" Moscow, Drug Register of 2001, p. 549, English translation provided pp. 1-2.
European Medicines Agency, Committee for Medicinal Products for Human Use (CHMP), "Assessment Report—Lyxumia", Nov. 28, 2012, pp. 1-81.
European Public Assessment Report (EPAR) Optisulin, EPAR Summary for the Public. Feb. 2009, pp. 1-3.
EuroQol Group, "EuroQol—a new facility for the measurement of health-related quality of life." Health policy (Amsterdam, Netherlands) 16(3):199-208 (Dec. 1990).
Extended European Search Report for European Application No. 14 19 7685; dated Aug. 10, 2015, pp. 1-4.
Extended European Search Report for European Application No. 14 19 7685; dated Oct. 6, 2015, pp. 1-4.
Extended European Search Report for European Application No. 15 15 1488.2; dated Jul. 7, 2015, pp. 1-8.
Faichney et al. "Metformin in Type 1 diabetes: Is This a Good or Bad Idea? "Diabetes Care, 2003, vol. 26 (5), pp. 1655.
FDA—Food and Drug Administration, CFR—Code of Federal Regulations Title 21, Chapter 1, Subchapter D, Part 312.21, "Phases of an investigation," Apr. 1, 2015, pp. 1-2.
FDA—Food and Drug Administration. Guidance for Industry—Diabetes Mellitus: Developing Drugs and Therapeutic Biologics for Treatment and Prevention. pp. 1-34 (Feb. 2008).
Final Rejection issued in U.S. Appl. No. 13/123,835; dated Nov. 18, 2015, pp. 1-16.
Final Rejection issued in U.S. Appl. No. 13/382,442; dated Sep. 21, 2016, pp. 1-32.
Final Office Action issued in U.S. Appl. No. 12/617,805; dated May 25, 2016, pp. 1-9.
Final Rejection in U.S. Appl. No. 13/633,496; dated Aug. 26, 2015, pp. 1-16.
Final Rejection in U.S. Appl. No. 13/633,496; dated Oct. 13, 2016, pp. 1-10.
Final Rejection in U.S. Appl. No. 13/633,563; dated Apr. 8, 2016, pp. 1-12.
Final Rejection issued in U.S. Appl. No. 13/509,507; dated May 13, 2016, pp. 1-11.
Non-Final Rejection issued in U.S. Appl. No. 13/509,507; dated Sep. 21, 2016, pp. 1-7.
Final Rejection issued in U.S. Appl. No. 14/172,151; dated Jan. 4, 2016, pp. 1-20.
Non-Final Rejection issued in U.S. Appl. No. 14/172,151; dated Jan. 19, 2017, pp. 1-20.
Non-Final Rejection issued in U.S. Appl. No. 13/467,707; dated Nov. 7, 2016, pp. 1-17.
Non-Final Rejection in U.S. Appl. No. 13/633,563; dated Oct. 5, 2016, pp. 1-12.
Non-Final Rejection issued in U.S. Appl. No. 14/303,895; dated Mar. 24, 2017, pp. 1-17.

(56) References Cited

OTHER PUBLICATIONS

Non-Final Rejection issued in U.S. Appl. No. 14/965,586; dated Mar. 22, 2017, pp. 1-17.
Non-Final Rejection issued in U.S. Appl. No. 15/068,286; dated Apr. 11, 2017, pp. 1-12.
Forman et al., "Higher Levels of Albuminuria within the Normal Range Predict Incident Hypertension." Journal of American Social Nephrology, Oct. 2008, vol. 19 (10), pp. 1983-1988.
Game, "Novel hypoglycaemic agents: Considerations in patients with chronic kidney disease" Nephron Clin Pract.126(1):14-18 (Jan. 11, 2014).
GenBank: AAA52578.1 "GM-CSF [*Homo sapiens*]" dated Nov. 8, 1994; accessed Jan. 18, 2017, one page.
GenBank: AAA59149.1 "Interleukin 4 [*Homo sapiens*]" dated Jan. 6, 1995; accessed Jan. 18, 2017, one page.
Gen Bank: AAP20099.1 "Interferon Alpha 2B [*Homo sapiens*]" dated Apr. 30, 2003; accessed Jan. 18, 2017, one page.
Gerstein et al., "Albuminuria and risk of cardiovascular events, death, and heart failure in diabetic and nondiabetic Individuals." JAMA 286(4):421-6 (Jul. 2001 ).
Giacometti et al., "In vitro activity of the histatin derivative P-113 against multidrug-resistant pathogens responsible or pneumonia in immunocompromised patients." 49 (3):1249-52 (Mar. 2005).
Giorda et al., "Pharmacokinetics, safety, and efficacy of DPP-4 inhibitors and GLP-1 receptor agonists in patients with type 2 diabetes mellitus and renal or hepatic impairment. A systematic review of the literature." Endocrine 46(3):406-19 (Aug. 2014; epub Feb. 8, 2014).
Glucophage XR, Product Information, Bristol-Meyers Squibb Company (Jan. 2009).
Gromada et al., "Alpha-Cells of the Endocrine Pancreas: 35 Years of Research but the Enigma Remains" Endocrine Reviews 28(1):84-116 (Jan. 2007).
Harkavyi & Whitton, "Glucagon-like peptide 1 receptor stimulation as a means of neuroprotection" British Journal of Pharmacology 159(3):495-501 (2010; Epub Jan. 29, 2010).
Hasslacher et al., "Diabetic kidney disease" Expand Clin Endocrinol Diabetes 122(7):391-94 (Jul. 2014).
Hinnen D.A., "Therapeutic Options for the Management of Postprandial Glucose in Patients With Type 2 Diabetes on Basal Insulin," Clinical Diabetes, 2015, vol. 33 (4), pp. 175-180.
Holman et al., "Three-year efficacy of complex insulin regimens in type 2 diabetes." N Engl J Med. 361 (18):1736-47 (Oct. 2009; Epub Oct. 22, 2009).
Hubschle et al., "Anti-atherosclerotic activity of lixisenatide in ApoE knockout mice" Abstract 809, Diabetologia, 55 (Supplement 1 ):S334 (Oct. 2012).
IDF, International Diabetes Federation Guideline Development Group, "Guideline for management of postmeal glucose in diabetes," Diabetes Research Clinical Practice, 2012, pp. 1-13.
International Search Report by the ISA for International Application No. PCT/EP2009/000018; dated Jun. 30, 2009, pp. 1-8.
International Search Report by the ISA for International Application No. PCT/EP2016/050804; dated Mar. 4, 2016, pp. 1-4.
International Search Report by the ISA for International Application No. PCT/EP2016/055267; dated Jun. 7, 2016, pp. 1-7.
International Search Report by the ISA for International Application No. PCT/EP2016/055267; dated May 20, 2016, pp. 1-7.
International Search Report by the ISA for International Application No. PCT/EP2016/055954; dated Sep. 9, 2016, pp. 1-12.
Inzucchi et al., "Management of hyperglycaemia in type 2 diabetes: a patient-centered approach. Position statement of the American Diabetes Association (ADA) and the European Association for the Study of Diabetes (EASD)." Diabetologia. 55(6):1577-96 (Jun. 2012; Epub Apr. 20, 2012).
Janka et al., "Comparison of basal insulin added to oral agents versus twice-daily premixed insulin as initial insulin therapy for type 2 diabetes." Diabetes Care 28(2):254-59 (Feb. 2005).

Juniper et al., "Determining a minimal important change in a disease-specific quality of life questionnaire." J Clin Epidemiol47(1):81-87 (Jan. 1994).
Katz et al., "The clinical burden of type 2 diabetes in patients with acute coronary syndromes: Prognosis and implications for short- and long-term management" Diabetes and Vascular Disease Research, 11 (6):395-409 (Nov. 2014).
Kelly et al., "Systematic Review: Glucose Control and Cardiovascular Disease in Type 2 Diabetes." Annals Internal Medicine, 2009, vol. 151 (6), pp. 394-403, (Sep. 2009; Epub Jul. 20, 2009).
Kendall et al., "Clinical Application of Incretin-Based Therapy: Therapeutic Potential, Patient Selection and Clinical Use." European Journal of Internal Medicine, Jul. 2009, vol. 20 (Suppl 2), pp. S329-S339.
Khaw et al., "Glycated Haemoglobin, Diabetes, and Mortality in Men in Norfolk Cohort of European Prospective Investigation of Cancer and Nutrition (EPIC Norfolk)." BMJ, Jan. 2001, vol. 322 (7277), pp. 15-18.
King et al., Global burden of diabetes, 1995-2025. Prevalence, numerical estimates and projections. Diabetes Care 21(9):1414-31 (Sep. 1998).
Kolotkin et al., "Assessing impact of weight on quality of life." Obes Res. 3(1 ):49-56 (Jan. 1995).
Kolotkin et al., "Development of a brief measure to assess quality of life in obesity." Obes Res. 9(2):102-11 (Feb. 2001).
Kondrat'ev VA Methodical Guidelines, May 7, 2010, p. 5 (in Russian only), found on Mar. 24, 2016, found from Internet: StudFields.ru>preview/4510743).
Korytkowski, "When oral agents fail: practical barriers to starting insulin." Int J Obes Relat Metab Disord. 26 Suppl 3 :S18-24 (Sep. 2002).
Lantus® Drug Description, downloaded Nov. 12, 2015, one page.
Lovshin & Drucker, "Incretin-based therapy for type 2 diabetes mellitus." Nat. Rev. Endocrinol. 5(5):262-69 (May 2009).
Madsbad, "Impact of Postprandial Glucose Control on Diabetes-Related Complications: How is the Evidence Evolving?" Journal of Diabetes and Its Complications, 2016, vol. 30, pp. 374-385, Available online Oct. 9, 2015.
McFarlane, "Insulin therapy and type 2 diabetes: management of weight gain," J Clin Hypertens (Greenwich). 11(10):601-7 (Oct. 2009).
Meadows et al., "Adaptation of the diabetes health profile (DHP-1) for use with patients with Type 2 diabetes mellitus: psychometric evaluation and cross-cultural comparison," Diabet. Med. 17(8):572-80 (Aug. 2000).
Meadows et al, "The diabetes health profile (DHP): a new instrument for assessing the psychosocial profile of insulin requiring patients: development and psychometric evaluation," Qual. Life Res. 5(2):242-54 (Apr. 1996).
Meier et al., "Contrasting Effects of Lixisenatide and Liraglutide on Postprandial Glycemic Control, Gastric Emptying, and Safety Parameters in Patients With Type 2 Diabetes on Optimized Insulin Glargine With or Without Metformin: A Randomized, Open-Label Trial" Diabetes Care 38(7):1263-73 (Jul. 2015).
Meier et al., "Effect of lixisenatide vs liraglutide on glycaemic control, gastric emptying and safety parameters in optimised insuline glargine type 2 diabetes mellitus +/− metformin" Abstract and Poster 926, 50th EASD Annual Meeting, Vienna, Austria Sep. 15-19, 2014, pp. 1-3.
Meigs et al., "Body Mass Index, Metabolic Syndrome, and Risk of Type 2 Diabetes or Cardiovascular Disease" Journal of Clinical Endocrinology & Metabolism, 91(8):2906-12 (Aug. 2006).
Merck Index, "Metformin", The Merck Index, 15th Edition (2013), RSC Publishing, 4 pages submitted, see entry 6009, p. 1102.
Miyazaki et al., "Improved Glycemic Control and Enhanced Insulin Sensitivity in Type 2 Diabetic Subjects Treated with Pioglitazone", Diabetes Care, Apr. 2001, vol. 24(4), pp. 710-719.
Monnier & Colette, "Addition of rapid-acting insulin to basal insulin therapy in type 2 diabetes: indications and modalities." Diabetes Metab 32(1):7-13 (Feb. 2006).
Monnier et al., "Postprandial and Basal Glucose in Type 2 Diabetes: Assessment and Respective Impacts" Diabetes Technology & Therapeutics, 2011, vol. 13 (Suppl 1 ), pp. S25-S32.

(56) References Cited

OTHER PUBLICATIONS

Nathan et al., "Modem-day clinical course of type 1 diabetes mellitus after 30 years' duration: the diabetes control and complications trial/epidemiology of diabetes interventions and complications and Pittsburgh epidemiology of diabetes complications experience (1983-2005)." Arch Intern Med. 169(14):1307-16 (Jul. 2009).
NCT00976937, ClinicaiTrials.gov, "24-week Study Comparing Lixisenatide (AVE001 0) to Sitagliptin as add-on to Metformin in Obese Type 2 Diabetic Patients Younger Than 50," last updated Mar. 10, 2014, Retrieved Aug. 31, 2016, pp. 1-5.
Nihonn-Iyakuhin-shu Iryoyaku "Pioglitazone hydrochloride, Insulin sensitizing hypoglycemic agent" 2009 Edition, Jiho Inc. p. 1901 (2009). English summary submitted.
Non-Final Rejection in U.S. Appl. No. 13/633,496; dated Apr. 21, 2016, pp. 1-12.
Non-Final Rejection issued in U.S. Appl. No. 13/467,707; dated Jun. 30, 2016, pp. 1-9.
Nowels et al., "Validation of the EQ-50 quality of life instrument in patients after myocardial infarction." Qual Life Res 14(1):95-105 (Feb. 2005).
Ohkubo et al., "Intensive insulin therapy prevents the progression of diabetic microvascular complications in Japanese patients with non-insulin-dependent diabetes mellitus: a randomized prospective 6-year study." Diabetes Res Clin Pract 28(2):103-17 (May 1995).
Osterbye et al., "Sulfatide Promotes the Folding of Proinsulin, Preserves Insulin Crystals, and Mediates Its Monomerization, "Journal of Glycobiology, 2001, vol. 11(6), pp. 473-479.
Paniker et al., "Beneficial effects of triple drug combination of pioglitazone with glibenclamide and metformin in type 2 diabetes mellitus patients on insulin therapy," J Assoc Physicians India, 51:1061-64 (Nov. 2003).
Park et al., "Long-Term Treatment of Glucagon-Like Peptide-1 Analog Exendin-4 Ameliorates Diabetic Nephropathy through Improving Metabolic Anomalies in db/db Mice." Journal American Society Nephrology, 2007, vol. 18 (4), pp. 1227-1238, Apr. 2007; Epub Mar. 14, 2007.
Partial International Search Report by the ISA for International Application No. PCT/EP2016/055954; dated Jun. 21, 2016, pp. 1-6.
Patel et al., "Stability Considerations for Biopharmaceuticals: Overview of Protein and Peptide Degradation Pathways" Available online at: http://www.bioprocessint.com/manufacturing/formulation/biopharmaceutical-product-stability-considerations-part-1/, 23 pages (2011).
Petersen & Christensen, Clinical potential of lixisenatide once daily treatment for type 2 diabetes mellitus Diabetes, Metabolic Syndrome and Obesity: Targets and Therapy, 6:217-31 (Jun. 2013).
Petrie, "The cardiovascular safety of incretin-based therapies: a review of the evidence" Cardiovascular Diabetology, 12(1):130, 12 pages (Sep. 2013).
Pinget et al., "Efficacy and safety of lixisenatide once daily versus placebo in type 2 diabetes insufficiently controlled on pioglitazone (GetGoal-P)," Diabetes, Obesity and Metabolism, 2013, vol. 15 (11), pp. 1000-1007.
Pi-Sunyer, "The Impact of Weight Gain on Motivation, Compliance, and Metabolic Control in Patients with Type 2 Diabetes Mellitus." Postgrad Med. 121(5):94-107 (Sep. 2009).
Raman & Heptulla, "New potential adjuncts to treatment of children with type 1 diabetes mellitus" Pediatric Research, 65(4):370-74 (Apr. 2009).
Ratner et al., "Efficacy and safety of lixisenatide once-daily versus placebo in patients with type 2 diabetes mellitus insufficiently controlled on sulfonylurea +/− metformin (GetGoal-S)" Presentation Abstract for Presentation No. 785. 47th EASD Annual Meeting, Lisbon, Sep. 12-16, 2011, pp. 1-3.
Ray et al., "Effect of intensive control of glucose on cardiovascular outcomes and death in patients with diabetes mellitus: a meta-analysis of randomized controlled trials." Lancet 373(9677):1765-72 (May 2009).
Register of medicaments (RM), 2003, issue 10, p. 517.

Remington: The Science and Practice of Pharmacy, Twentieth Edition, Lippincott Williams & Wilkins, USA, "Oral Hypoglycemic and Hyperglycemic Drugs" 4 pages; (2000).
Remington: The Science and Practice of Pharmacy, Twentieth Edition, Lippincott Williams & Wilkins, USA, "Pancreatic Disorders" and "Metformin Hydrochloride" 5 pages; (2000).
Rosenstock et al., Advancing Basal Insulin Glargine with Prandial Lixisenatide QD vs. Insulin Glulisine QD or TID in T2DM: The GetGoalDuo2 Evidence-Based Trial (NCT01768559). Poster 107-LB, Presented on Sunday, Jun. 7, 2015, 75th Scientific Sessions of the American Diabetes Association, Boston, Massachusetts Jun. 5-9, 2015.
Rothstein et al., "Anticandida activity is retained in P-113, a 12-amino-acid fragment of histatin 5." Antimicrob Agents Chemother. 45(5):1367-73 (May 2001).
RPMI-1640 Media Formulation, Sigma Aldrich, accessed on Jul. 10, 2016, pp. 1-5.
Ruetten et al., "Protective effects of the GLP-1 receptor agonist lixisenatide on ischaemia-reperfusion-induced myocardial infarction in an isolated rat heart model" Diabetologia, Abstract 810, 54(Supplement 1):S329 (Sep. 2011).
Russell-Jones & Khan, "Insulin-associated weight gain in diabetes: causes, effects and coping strategies." Diabetes Obes Metab. 9(6):799-812 (Nov. 2007).
Russell-Jones, "Current developments in the treatment of diabetes: the incretin therapies" Br J Diabetes Vase Dis. 10:21-30 (Feb. 2010).
Sanofi, "A randomized, double-blind, placebo controlled trial to assess safety, tolerability, pharmacokinetics and pharmacodynamics of lixisentatide in pediatric (10-17 years old) and adult patients with type 2 diabetes", Sanofi, p. 1-12 (2015). retrieved from the internet: http://en.sanofi.com/img/contentlstudy/PKD11475_summary.pdf (issued Jan. 13, 2015; retrieved on Jun. 16, 2015).
Sanofi Press Release entitled "Sanofi Announces Top-Line Results for Cardiovascular Outcomes Study of Lyxumia® (lixisenatide)." dated Mar. 19, 2015, Paris, France, pp. 1-2.
Schernthaner et al., "Is the ADA/EASD algorithm for the management of type 2 diabetes (Jan. 2009) based on evidence or opinion? A critical analysis." Diabetologia.53(7):1258-69 (Jul. 2010; Epub Mar. 31, 2010).
Seino et al., "Lixisenatide significantly improves glycemic control in Asian patients with T2DM insufficiently controlled on basal insulin± SU." Diabetes, Abstract book for 71st Scientific Session. p. A76; Abstract 278-0R (2011).
Shaw et al., "US valuation of the EQ-5D health states: development and testing of the D1 valuation model." Med Care 43(3):203-20 (Mar. 2005).
Shehadeh et al., "Can GLP-1 preparations be used in children and adolescents with diabetes mellitus?" Pediatric Endocrinology Reviews, 11(3):324-47 (Mar. 2014).
Sillars et al., "Sulphonylurea-metformin combination therapy, cardiovascular disease and allcause mortality: the Fremantle Diabetes Study." Diabetes Obes Metab. 12(9):757-65 (Sep. 2010).
Spertus et al., "Monitoring the quality of life in patients with coronary heart disease." Am J Cardiol. 74(12):1240-44 (Dec. 1994).
Spertus et al., "Development and Evaluation of the Seattle Anginal Questionnaire: a New Functional Status Measure for Coronary Artery Disease." Journal American College of Cardiology, 25(2):333-341 (Feb. 1995).
Spertus et al., "Health Status Predicts Long-Term Outcome in Outpatients with Coronary Disease." Circulation, 106(1):43-49 (Jul. 2002).
Standardized Definitions for Cardiovascular Outcomes Trials: Draft Recommendations. Division of Metabolism and Endocrinology Products. Center for Drug Evaluation and Research (CDER). pp. 1-34, (Mar. 24, 2010).
Tanner & Davies, "Clinical longitudinal standards for height and height velocity for North American children." J Pediatr. 107(3):317-29 (Sep. 1985).
The Advance Collaborative Group, "Intensive Blood Glucose Control and Vascular Outcomes in Patients with Type 2 Diabetes." New England Journal of Medicine, 358(24):2560-72 (Jun. 2008).

(56) References Cited

OTHER PUBLICATIONS

The Criteria Committee of the New York Heart Association, "Nomenclature and Criteria for Diagnosis of Diseases of the Heart and Great Vessels." 9th edition. Boston, Mass: Little, Brown & Co; pp. 253-256 (1994).
Tirosh et al., "Normal Fasting Plasma Glucose Levels and Type 2 Diabetes in Young Men" New England Journal of Medicine, 353(14):1454-62 (Oct. 2005).
UK Prospective Diabetes Study (UKPDS) Group, "Tight Blood Pressure Control and Risk of Macrovascular and Microvascular Complications in Type 2 Diabetes (UKPDS 38)," BMJ, 317:703-13 (Sep. 1998).
Vilsboll et al., "Liraglutide, a Long-Acting Human Glucagon-Like Peptide-1 Analog, Given as Monotherapy Significantly Improves Glycemic Control and Lowers Body Weight Without Risk of Hypoglycemia in Patients With Type 2 Diabetes," Journal of Diabetes Care, 30(6):1608-10 (2007).
Weir "Glucagon-like peptide-1 (7-37) actions on endocrine pancreas." Diabetes 38(3):338-42 (Mar. 1989).
Werner et al., "The GLP-1 Receptor Agonist AVE0010 Abolishes OGTT-Induces Blood Glucose Excursion in Healthy, Normoglycemic Dog without Risk of Hypoglycemia" Diabetes, 56 (Supplement 1):A129 (Jun. 2007). Abstract Submitted.
WHO, World Health Organization Media Center. Diabetes Fact Sheet. Available from: http://www.who.int/mediacentre/factsheets/fs312/en/index.html. Accessed Jun. 13, 2016, pp. 1-6.
WHO, World Health Organization Media Center. Obesity and overweight, Fact Sheet No. 311. Updated Jan. 2015, pp. 1-5.
Wikipedia® Entry for "Body Mass Index" Retrieved from the Internet: https://en.wikipedia.org/wiki/Body mass_index, 2016, pp. 1-14, retrieved Feb. 26, 2016.
Wikipedia® Entry for "Metformin" Retrieved from the Internet: https://en.wikipedia.org/wiki/Metformin 2016, pp. 1-21, retrieved Apr. 11, 2016.
Wikipedia® Entry for "Pioglitazone" Retrieved from the Internet: https://en.wikipedia.org/wiki/Pioglitazone 2016, pp. 1-3, retrieved Apr. 11, 2016.
Wikipedia® Entry for "Lixisenatide" Retrieved from the Internet: https://en.wikipedia.org/wiki/Lixisenatidehttps://en.wikipedia.org/wiki/Lixisenatide, pp. 1-2, updated Dec. 2015.
Wild et al., "Global prevalence of diabetes: estimates for the year 2000 and projections for 2030." Diabetes Care 27 (5):1047-53 (May 2004).
Williams et al., "Macrovascular disease in Diabetes." In handbook of Diabetes. 2nd ed. Williams G, Pickup JC, Eds. Oxford, UK, Blackwell Science pp. 151-158 (1999).
Wivioti et al., "Greater Clinical Benefit of More Intensive Oral Anti platelet Therapy With Prasugrel in Patients With Diabetes Mellitus in the Trial to Assess Improvement in Therapeutic Outcomes by Optimizing Platelet Inhibition With Prasugrel-Thrombolysis in Myocardial Infarction 38," Circulation, 118(16):1626-36, (Oct. 2008; Epub Aug. 31, 2008).
Wohlfart et al., "Cardioprotective effects of lixisenatide in rat myocardial ischemia-reperfusion injury studies" Journal of Translational Medicine, 11(1):84, 12 pages (Mar. 2013).
Wolever et al., "Second-meal effect: low-glycemic-index foods eaten at dinner improve subsequent breakfast glycemic response." Am J Clin Nutr 48(4):1041-47 (Oct. 1988).
World Health Organisation Report on "Definition and Diagnosis of Diabetes Mellitus and Intermediate Hyperglycemia: Report of a WHO/IDF Consultation," pp. 1-50 (2006).
Wright et al., U.K. Prospective Diabetes Study Group. "Sulfonylurea inadequacy: efficacy of addition of insulin over years in patients with type 2 diabetes in the UK. Prospective Diabetes Study (UKPDS 57)." Diabetes Care 25(2):330-36 (Feb. 2002).
Yusuf et al., "Effects of Clopidogrel in Addition to Aspirin in Patients with Acute Coronary Syndromes without ST-Segment Elevation." New England Journal Medical, 345(7):494-502 (Aug. 2001).

Zealand Pharma Company Announcement "Zealand Pharma, Additional positive results from Global Phase III program with -3-lixisenatide for type 2 diabetes", Apr. 12, 2011, pp. 1-3, URL, http://files.shareholder.com/downloads/ABEA-58QR0J/0x0x458202/3ccd84a6-5f99-451a-ada0-0a8282da3dad/ZEAL_News_2011_4_12Company_Releases.pdf.
Zeitler et al., "ISPAD Clinical Practice Consensus Guidelines 2014. Type 2 diabetes in the child and adolescent." Pediatr Diabetes 15(Suppl20):26-46 (Sep. 2014).
Zimmet et al., "Global and societal implications of the diabetes epidemic." Nature 414(6865):782-87 (Dec. 2001).
Zimmet et al., "The metabolic syndrome in children and adolescents." Lancet 369(9579):2059-61 (Jun. 2007).
Zoungas et al., "Combined Effects of Routine Blood Pressure Lowering and Intensive Glucose Control on Macrovascular and Microvascular Outcomes in Patients With Type 2 Diabetes. New results from the Advance trial." Diabetes Care, 32(11):2068-74 (Nov. 2009; Epub Aug. 3, 2009).
Li & Holscher, "Common pathological processes in Alzheimer disease and type 2 diabetes: A review" Brain Research Reviews, 56:384-402 (2007).
Lill, "Production of fast-acting insulins and delayed-release insulins—how can this problem be solved by technology? Insulin formulations," Pharmazie in unserer Zeit 30(1):56-61 (2001). (English Translation Included).
"Lixisenatide, Chemical Structure CID 16139342, Pubchem, accessed Feb. 5, 2015 at URLpubchem.ncbi.nlm.nih.gov/summary/summary.cgi?sid=135267128&viewopt=Deposited, pp. 1-3.".
Liu & Ruus, Abstract "Pharmacokinetics and Safety of the GLP-1 Agonist AVE0010 in Patients with Renal Impairment," Diabetes 58 (Suppl. 1): Abstract 557-P for the 69th Scientific Session of the American Diabetes Association Jun. 5-9, 2009, New Orleans, Louisiana, pp. 1-2.
Lotharius et al., "Effect of Mutant a-Synuclein on Dopamine Homeostasis in a New Human Mesencephalic Cell Line," Journal of Biological Chemistry, 277:38884-94 (2002).
Lotharius et al., "Progressive Degeneration of Human Mesencephalic Neuron-Derived Cells Triggered by Dopamine-Dependent Oxidative Stress Is Dependent onthe Mixed-Lineage Kinase Pathway," Journal of Neuroscience, 25:6329-42 (2005).
Lyxumia® ANNEX I—Summary of product characteristics. Date of first authorisation: Feb. 1, 2013, pp. 1-92.
Lyxumia® Product Information—European Medicines Agency, first published Mar. 14, 2013, pp. 1-2.
Lyxumia 10 micrograms solution for injection, Summary of Product Characteristics, updated Oct. 31, 2014, pp. 1-12.
Mancuso et al., "Clinical features and pathogenesis of Alzheimer's disease: involvement of mitochondria and mitochondrial DNA," Adv Exp Med Biol., 685:34-44 (2010).
Marbury, et al., "A Pilot Study to Examine the Feasability of Insulin Glargine in Subjects With Impaired Fasting Glucose, Impaired Glucose Tolerance or New-Onset Type 2 Diabetes", Experimental and Clinical Endocrinology & Diabetes: Official Journal, German Society of Endocrinology and German Diabetes Associate, 116(5):282-88 (May 2008).
Margolis, "Diagnosis of Huntington's Disease,"Ciin. Chem. 49:1726-32 (2003).
Markussen et al., "Soluble, prolonged-acting insulin derivatives. I. Degree of protraction and crystallizabity of insulins substituted in the termini of the B-chain," Prot. Eng. 1(3), 1987, pp. 205-213.
Markussen et al., "Soluble, prolonged-acting insulin derivatives. II. Degree of protraction and crystallizability of insulins substituted in positions A17, B8, B13, B27 and B30," Prot. Eng. 1(3), 1987, pp. 215-223.
Markussen et al., "Soluble, prolonged-acting insulin derivatives. III. Degree of protraction, crystallizability and chemical stability of insulins substituted in positions A21, B13, B23, B27 and B30," Prot. Eng. 2(2), 1988, pp. 157-166.
Martin et al. "Neurodegenation in excitotoxcity, global cerebral ischemia, and target deprivation: A perspective on the contributions of aptopsis and necrosis," Brain Res. Bull, 46:281-309 (1998).

(56) References Cited

OTHER PUBLICATIONS

Martin et al., "Exendin-4 improves glycemic control, ameliorates brain and pancreatic pathologies and extends survival in a mouse model of Huntington's Disease" Diabetes (2009) pp. 318-328, vol. 58, No. 2.
Mattson "Calcium and neurodegeneration." Aging Cell 6:337-50 (2007).
McClean et al., "The diabetes drug Liraglutide prevents degenerative processes in a mouse model of Alzheimer's disease" Journal of Neuroscience 31(17):6587-94 (2011).
McClean. et al., "Glucagon-like peptide-1 analogues enhance synaptic plasticity in the brain: A link between diabetes and Alzheimer's disease" European Journal of Pharmacology (2010) pp. 158-162, vol. 630.
Mecklenburg & Guinn, "Complications of insulin pump therapy: the effect of insulin preparation," Diabetes Care 8 (4):367-70 (1985).
Medline Plus, "Obesity" available at http://www.nlm.nih.gov/medlineplus/obesity.html, Retrieved Aug. 22, 2013, one page.
Meier, "GLP-1 receptor agonists for individualized treatment of type 2 diabetes mellitus." Nat. Rev. Endocrinol. 8:728-42 (2012).
Mikhail, "Is liraglutide a useful addition to diabetes therapy?" Endocr Practice 16(6):1028-37 (Nov.-Dec. 2010).
Monnier et al., The loss of postprandial glycemic control precedes stepwise deterioration of fasting with worsening diabetes. Diabetes Care. 30(2):263-69 (2007).
Moreno-Gonzalez et al., "Extracellular Amyloid-β and Cytotoxic Glial Activation Induce Significant Entorhinal Neuron Loss in Young PS1M146LJAPP751SL Mice" Journal of Alzheimer's Disease 18:755-776 (2009).
Moretto et al., "Efficacy and Tolerability of Exenatide Monotherapy Over 24 Weeks in Antidiabetic Drug-Naive Patients with Type 2 Diabetes: A Randomized, Double-Blind, Placebo-Controlled, Parallel-Group Study", Clinical Therapeutics, 30(8)1448-60 (Aug. 2008).
Muzaffar et al., "The Mechanism of Enhanced Insulin Amyloid Fibril Formation by NaCIIs Better Explained by a Conformational Change Model," PLoS One, 2011 Nov. 21, pp. 1-11, 6(11):e27906.
Nakagawa et al., "Receptor gene expression of glucagon-like peptide-1, but not of glucose-dependent insulinotropic polypeptide, in rat nodose ganglion cells" Auton Neurosci (2004) pp. 36-43, vol. 110.
Nathan et al., "Management of hyperglycaemia in type 2 diabetes mellitus: a consensus algorithm for the initiation and adjustment of therapy. Update regarding the thiazolidinediones." Diabetologia. 51(1):8-11 (2008).
Nauck et al., "Comparative evaluation of incretin-based antidiabetic medications and alternative therapies to be added to melformin in the case of monotherapy failure," Journal of Diabetes Investigation 1(1-2):24-36 (Feb.-Apr. 2010).
NCT00715624 Clinical Trials.gov "GLP-1 Receptor Agonist Lixisenatide in Patients With Type 2 Diabetes for Glycemic Control and Safety Evaluation, on Top of Basal Insulin (GetGoal-L)" (2008-2014), p. 1-6 (Feb. 2011).
NCT00976937, ClinicalTrials.gov, "24-week Study Comparing Lixisenatide (AVE0010) to Sitagliptin as add-on to Metformin in Obese Type 2 Diabetic Patients Younger Than 50," May 6, 2011, Retrieved Nov. 7, 2011, pp. 1-4.
NCT00299871, ClinicalTrials.gov, "Dose Ranging Study of the GLP-1 Agonist AVE0010 in Metformin-Treated Subjects With Type 2 Diabetes Mellitus," Jun. 22, 2010, Retrieved Nov. 7, 2011, pp. 1-5.
NCT00712673, Clinical Trials.gov, "GLP-A Agonist AVE0010 (Morning or Evening) in Patients with Type 2 Diabetes for Glycemic Control and Safety Evaluation, on Top of Metformin", Mar. 22, 2011, pp. 1-4.
NCT00975286, Clinical Trials.gov, "24-week Treatment with Lixisenalide in Type 2 Diabetes Insufficiently Controlled With Melformin and Insulin Glargine", Aug. 8, 2011, pp. 1-4.

NCT00688701 Clinical Trials.gov "GLP-1 Receptor Agonist Lixisenatide in Patients with Type 2 Diabetes for Glycemic Control and Safety Evaluation in Monotherapy (GetGoal-Mono)" accessed Jul. 27, 2014; pp. 1-5.
NCT02058147 ClinicalTrials.gov "Efficacy and Safety of Insulin Glargine/Lixisenatide Fixed Ratio Combination Compared to Insulin Glargine Alone and Lixisenatide Alone on Top Metformin in Patients With T2DM (LixLan-O)" first received by ClinicalTrials.gov on Feb. 6, 2014, pp. 1-3.
NCT02058160 ClinicalTrials.gov "Efficacy and Safety of the Insulin Glargine/Lixisenatide Fixed Ratio Combination Versus Insulin Glargine in Patients With Type 2 Diabetes (LixiLan-L)" first received by ClinicalTrials.gov on Feb. 6, 2014, pp. 1-3.
NCT01195454, NIH Clinical Trials, "Euglycemic clamp dose-response study comparing insulin glargine U300 with Lantus U100" last updated Dec. 13, 2010, pp. 1-4.
NCT00763815, ClinicalTrials.gov, U.S. National Institutes of Health: "GLP-1 Agonist AVE0010 in Patients With Type 2 Diabetes for Glycemic Control and Safety Evaluation on Top of Pioglitazone (GetGoal-P)" pp. 1-8 (Jun. 27, 2011).
NCT01255163, ClinicalTrials.gov "A Clinical Trial of Exendin-4 for the Treatment of Alzheimer's Disease" accessed Aug. 8, 2011, pp. 1-7.
NCT01174810, ClinicalTrials.gov "Exendin-4 as a Treatment for Parkinson's Disease—Pilot Study" accessed Aug. 8, 2011, pp. 1-5.
EFC10780 (Sanofi study), "A randomized, double-blind, double-dummy, 2-arm parallel-group, multicenter 24-week study comparing the efficacy and safety of AVE0010 to sitagliptin as add-on to metformin in obese type 2 diabetic patients younger than 50 and not adequately controlled with metformin (EFC10780)" p. 1-4 (Jan. 29, 2014).
EFC10781 Clinical Trials, "24-week Treatment With Lixisenatide in Type 2 Diabetes Insufficiently Controlled With Metformin and Insulin Glargine" ClinicalTrials.gov; EFC10781 pp. 1-5 (Sep. 2009).
EFC6018; Clinical trial EudraCT 2007-005887-29, "GetGoal-Mono" accessed Jul. 27, 2014; pp. 1-16.
EFC6017; Clinical Trial Eudra CT No. 2007-005884-92, accessed Apr. 24, 2015, one page.
Neidle, "18.2 Failure Modes in the Discovery Process" Cancer Drug Design and Discovery, Elsevier/Academic Press, pp. 427-431 (2008).
Nettleton et al. "Characterization of the Oligomeric States of Insulin in Self-Assembly and Amyloid Fibril Formation by Mass Spectrometry," Biophysical J., v79, 2000, p. 1053-1065.
Christensen et al. "Lixisenatide for type 2 diabetes mellitus," Expert Opin. 20(4):549-57 (Epub Mar. 11, 2011).
Christensen et al., "Lixisenatide, a Novel GLP-1 Receptor Agonist for the Treatment of Type 2 Diabetes Mellitus", IDrugs: The Investigational Drugs Journal 12(8):503-13 (Aug. 2009).
Cochran et al., "The Use of U-500 in Patients with Extreme Insulin Resistance" Diabetes Care, 28(5):1240-44 (2005).
Colino et al., "Therapy with insulin glargine (Lantus) in toddlers, children and adolescents with type 1 diabetes," Diabetes Research and Clinical Practice (2005), vol. 70, pp. 1-7.
Community register of medicinal products for human use, Chemical Subgroup A10BX, "Lyxumia" European Commision—Public Health, (May 2, 2013) 1 page.
Colclough et al., Abstract "Levels of FPG and HbA1c Control and the Relationship to BMI in T2D Patients Treated with Basal Insulin and OAD Therapy." Abstract 2416-PO; Presented at the 72nd Scientific Session at the American Diabetes Association Meeting, 2012, A609, one page.
Craig et al., "ISPAD Clinical Practice Consensus Guidelines 2014 Compendium—Definition, epidemiology, and classification of diabetes in children and adolescents." Pediatric Diabetes, 15(Suppl. 20):4-17 (2014).
Crapo et al., "Postprandial plasma-glucose and -insulin responses to different complex carbohydrates," Diabetes 26 (12):1178-83 (Dec. 1977).
Croom et al., "Liraglutide A Review of its Use in Type 2 Diabetes Mellitus," Drugs, 69(14):1985-2004 (2009).

(56) References Cited

OTHER PUBLICATIONS

Fieller, Symposium on Interval Estimation; "Some Problems with Interval Estimation" Journal of the Royal Statistical Society 16(2):175-85 (1954).
Cryer "Hypoglycemia is the limiting factor in the management of diabetes," Diabetes Metab. Res. Rev. 15(1):42-46 (Jan.-Feb. 1999).
Cvetkovic et al., "Exenatide A Review of Its Use in Patients with Type 2 Diabetes Mellitus (as an Adjunct to Metformin and/or a Sulfonylurea)," Drugs, 67(6):935-54 (2007).
Czech et al., "Proteolytical processing of mutated human amyloid precursor protein in transgenic mice" Molecular Brain Research 47:108-116 (1997).
D'Alessio et al., "GLP-1 Receptor Agonists: Strategies for PPG Control," Medical Nursing Edu., 3:1-26 (Jan. 2011).
Database, Adiscti, "A randomized, 4-sequence, cross-over, double bind, dose response study of 0.4, 0.6 and 0.09 U/kg insluin glarine U300 compared to 0.4 U/kg Lantus U100 in patients with diabetes mellitus type I using euglycemic clamp technique" last updated Dec. 16, 2010, pp. 1-4.
Davis How to Convert mg to mmol/L, available online at http://www.ehow.com/how_8498850_convert mg-mmoll.html (accessed on Nov. 11, 2015).
de Arriba et al., "Carbonyl stress and NMDA receptor activation contribute to methylglyoxal neurotoxicity" Free Radical Biology & Medicine, 40:779-90 (2006).
Definition of palliative, http://medicaldictionary.thefreedictionary.com/, accessed on Nov. 6, 2014, pp. 1-2.
Definition of sphincter of pancreatic duct in the Medical Dictionary, http://medicaldictionary.thefreedictionary.com/, accessed on May 22, 2014, pp. 1-2.
DeFronzo "Effects of Exenatide (Exendin-4) on Glycemic Control and Weight Over 30 Weeks in Metformin-Treated Patients with Type 2 Diabetes", Diabetes Care 28(5):1092-1100 (May 2005).
DeFronzo "Pathogenesis of Type 2 Diabetes Implications for Metformin" Short Communication, Drugs 1999; 58(Suppl 1):29-30 (Sep. 1999).
DeFronzo "Pharmacologic Therapy for Type 2 Diabetes Mellitus." Ann Int Med. 131:281-303 (1999).
Delatour et al., "Alzheimer pathology disorganizes cortico-cortical circuitry: direct evidence from a transgenic animal model" Neurobiology of Disease, 16:41-47 (2004).
De Le Pena, "Pharmacokinetics and Pharmadynamics of High-Dose Human Regular U-500 Insulin Versus Human Regular U-1 00 Insulin in Healthy Obese Subjects" Diabetes Care, 34(12):2496-501 (2011).
De Rosa, et al. "Intranasal administration of nerve growth factor (NGF) rescues recognition memory deficits in A D11 anti-NGF transgenic mice." Proc Natl Acad. Sci., 102:3811-6 (2005).
DeWitt, "Case Study: Treating New On-Set Catabolic Type 2 Diabetes With Glargine and Lispro", Clinical Diabetes vol. 24, No. 4, pp. 180-1 (Oct. 2006).
deVries et al., "Sequential intensification of metformin treatment in type 2 diabetes with liraglutide followed by randomized addition of basal insulin prompted by A1C targets." Diabetes Care 35:1446-54 (2012).
Diabetes Prevention Program Research Group. "Reduction in the incidence of type 2 diabetes with lifestyle intervention or metformin." N. Engl J. Med. 346(6):393-403 (2002).
Donelli, "Plastic Biliary Stent Occlusion: Factors Involved and Possible Preventive Approaches," Clinical Medicine & Research 5(1):53-60 (Mar. 2007).
Dormandy et al., "Secondary prevention of macrovascular events in patients with type 2 diabetes in the PROactive Study (PROspective pioglitAzone Clinical Trial in macrovascular Events): a randomised controlled trial," Lancet. 366 (9493):1279-89 (Oct. 8, 2005).
Doyle et al., "Mechanisms of action of glucagon-like peptide 1 in the pancreas" Pharmacal Ther. (Mar. 2007) pp. 546-593, vol. 113, No. 3.

Drucker et al., "The incretin system: glucagon-like peptide-1 receptor agonists and dipeptidyl peptidase-4 inhibitors in type 2 diabetes." Lancet; 368(9548):1696-705 (Nov. 11, 2006).
Dubois et al., "Revising the definition of Alzheimer's disease: a new lexicon." Lancet Neural. 9: 1118-27 (2010).
During et al., "Glucagon-like peptide-1 receptor is involved in learning and neuroprotection" Nat Med (2003) pp. 1173-1179, vol. 9.
Dunn et al., "Insulin Glargine: An Updated Review of its Use in the Management of Diabetes Mellitus" Drugs 63 (16):1743-1778 (2003).
Eckert et al., "Alzheimer's Disease-like Alterations in Peripheral Cells from Presenilin-1 Transgenic Mice" Neurobiology of Disease 8, 331-342 (2001).
EMA Press Release, "European Medicines Agency recommends suspension of Avandia, Avandamet and Avaglim" pp. 1-2 (Sep. 23, 2010).
European Medicines Agency—Science Medicines Health, "Guideline on clinical investigation of medicinal products in the treatment of diabetes mellitus" Committee for Medicinal Products for Human Use, Jan. 20, 2010, pp. 1-19.
Executive Summary, Standards of Medical Care in Diabetes—2009' Diabetes Care, 32(Suppl. 1):S6-S12 (Jan. 2009).
Ex Parte Herrmann, Appeal No. 2009-001777 U.S. Appl. No. 10/616,457 (B. Pai. dated Nov. 13, 2009).
Fabunmi et al., "Patient characteristics, drug adherence patterns, and hypoglycemia costs for patients with type 2 diabetes mellitus newly initiated on exenatide or insulin glargine." Curr Med Res Opin. 25(3):777-86 (2009).
Faivre et al., "Effect of GIP Analogues in Neuronal Signalling, Cell Proliferation and Learning and Memory." Regulatory Peptides; 164(1):40-41 (Sep. 9, 2010, published online Aug. 20, 2010).
FDA Guidance for Industry, US Department of Health and Human Services, Food and Drug Administration, Center for Drug Evaluation and Research (COER), pp. 1-11, Feb. 2014.
FDA Frequently Asked Questions about Combination Products; accessed from www.fda.gov/CombinationProducts/AboutCombinationProducts/usm101496.1/htm, 2009 downloaded Jul. 13, 2012, pp. 1-18.
FDA label of Apidra®, May 2014, pp. 1-35.
FDA label of Humalog®, Mar. 2013, pp. 1-27.
FDA label of Lantus®, Oct. 2013, pp. 1-44.
Afiren, "GLP-1 for type 2 diabetes", Experimental Cell Research, 317(9):1239-45 (Jan. 2011).
American Diabetes Association, "Standards of Medical Care in Diabetes—2017" Diabetes Care 40(Supplement 1):S1-S142 (Jan. 2017).
Bergenstal et al., "Type 2 Diabetes: Assessing the Relative Risks and Benefits of Glucose-lowering Medications" The American Journal of Medicine 123(4):e9-e18 (Apr. 2010).
Byetta® Summary of Product Characteristics, updated Jul. 22, 2016, last accessed Jul. 31, 2017, pp. 1-13.
Berard et al., "Canadian Diabetes Association 2008 Clinical Practice Guidelines for the Prevention and Management of Diabetes in Canada." Canadian Journal of Diabetes 32(Supplement 1):1-215 (Sep. 2008).
Correa, "Pautas para el examen de patentes farmaceuticas. Una perspectiva desde la Salud Publica. Documento de Trabajo" Universidad de Buenos Aires, Mar. 2008, see English on pp. 19-20, pp. 1-66.
Definition of "reduce" Dictionary.com; last accessed Aug. 13, 2017, pp. 1-4.
Denker et al., "Exenatide (Exendin-4)-Induced Pancreatitis: A case report" Diabetes Care 29(2):471 (Feb. 2006).
Distiller et al., Abstract and Poster: "Pharmacokinetics and Pharmacodynamics of a New GLP-1 Agonist AVE0010 in Type 2 Diabetes Patients" Meeting: 68th Scientific Sessions (Jun. 2008) Abstract and Poster No: 520-P.
Godoy-Matos, "The role of glucagon on type 2 diabetes at a glance," Diabetology & Metabolic Syndrome 6:91, pp. 1-5 (Aug. 2014).
Home et al., "Management of type 2 diabetes: updated NICE guidance" BMJ 336: 1306-1308 (Jun. 2008).

(56) References Cited

OTHER PUBLICATIONS

Ismail-Beigi et al., "Individulaizing Glycemic Targets in Type 2 Diabetes Mellitus: Implications of Recent Clinical Trials" Annals of Internal Medicine 154(8):554-559 (Apr. 2011).
Lee et al., "Goals of Glycemic Control in Frail Older Patients with Diabetes" JAMA 305(13):1350-51 (Apr. 2011).
Lyxumia, European Commission—Public Health; Chemical Subgroup A10BX, Community Register of Medicinal Products for Human Use, p. 1-2 (May 2, 2013; last updated Oct. 29, 2014).
Nathan et al., "Medical Management of Hyperglycemia in Type 2 Diabetes: A Consensus Algorithm for the Initiation and Adjustment of Therapy" Diabetologia 52:17-30 (2009: Epub Oct. 22, 2008).
NCT00866658 ClinicalTrials.gov, "GLP-1 agonist AVE0010 in patients with type 2 diabetes for glycemic control and safety evaluation, on top of basil insulin +/- sulfonylurea" p. 1-3, accessed Mar. 16, 2016 (updated Aug. 3, 2010).
Nice, National Institute for Health and Care Excellence, "Type 2 diabetes in adults: management" pp. 1-45 (Dec. 2, 2015).
Rodbard et al., "Statement by an American Association of Clinical Endocrinologists/American College of Endocrinology Consensus Panel on Type 2 Diabetes Mellitus: An Algorithm for Glycemic Control" Endocrine Practice 15(6):540-59 (Sep./Oct. 2009).
Sanofi-aventis Press Release, "Once Daily Lixisenatide in Combination with Basal Insulin Demonstrates Significant Improvement in Glucose Control" Paris, France (Sep. 30, 2010) pp. 1-3.
Sutter Medical Foundation, "Type 2 Diabetes Adult Outpatient Insulin Guidelines" Feb. 2011, pp. 1-6.
Non-Final Rejection in U.S. Appl. No. 13/633,496; dated May 25, 2017, pp. 1-10.
Non-Final Rejection issued in U.S. Appl. No. 15/197,378; dated Jun. 15, 2017, pp. 1-13.
Non-Final Office Action issued in U.S. Appl. No. 15/275,867; dated Jun. 1, 2017; pp. 1-11.
Non-Final Office Action issued in U.S. Appl. No. 15/340,969; dated Jul. 24, 2017, pp. 1-6.
Bucceri et al., "Gallbladder and gastric emptying: relationship to cholecystokininemia in diabetics." Eur. J. Intern. Med. 13(2):123-28 (Mar. 2002).
Clinical Trials Archive for Trial No. NCT00763815 updated Feb. 21, 2014. Accessed at https://clinicaltrials.gov/archive/NCT00763815/2014_02_21/changes Accessed on Nov. 13, 2017. pp. 1-13.
FDA, "Guidance of Industry—Bioequivalence studies with pharmacokinetic endpoints for drugs submitted under an ANDA" Draft Guidance by the U.S. Department of Health and Human Services, Food and Drug Administration, Center for Drug Evaluation and Research (CDER), Dec. 2013, pp. 1-24.
Gillies et al, "Insulin Glargine" Drugs 59(2)L253-60 (Feb. 2000).
Gualandi-Signorini & Giorgi, "Insulin formulations—a review" European Review for Medical and Pharmacological Sciences 5:73-83 (2001).
Lantus® 100U/mlsolution for injection (insulin glargine); published in vol. 24 No. 9 of Pract. Diab. Int. Nov./Dec. 2007, p. 472.
Lawson et al., "Coordination of gastric and gallbladder emptying after ingestion of a regular meal." Gastroenterology. 85(4):866-70 (Oct. 1983).
NCT00715624 Clinical Trials.gov "GLP-1 Agonist AVE0010 in Patients With Type 2 Diabetes for Glycemic Control and Safety Evaluation, on Top of Basal Insulin" (updated Mar. 2, 2011), p. 1-3.
NCT01195454, NIH Clinical Trials, "Euglycemic clamp dose-response study comparing insulin glargine U300 with Lantus U100" last updated Sep. 3, 2010, pp. 1-3.
Profile of Lantus® (insulin glargine injection) 100 units/ml vs. NPH in patients with type 1 diabetes; https://www.lantus.com/hcp/aboutlantus/vs-nph, pp. 1-4, last accessed Feb. 19, 2016.
Rosenstock et al., "Reduced Hypoglycemia Risk with Insulin Glargine: A meta-analysis comparing insulin glargine with human NPH insulin in type 2 diabetes" Diabetes Care 28(4):950-55 (Apr. 2005).
Shi, "The Newest Handbook of Clinical Drugs" Military Medical Science Press, p. 809, (Jan. 2008). English translation submitted.

Tang, "Biotech Drugs—Introduction and Practice Handbook" Chemical Industry Press, pp. 635-36, (Jan. 2008). English translation submitted.
Wikipedia® entry for "Standard deviation" Retrieved on Oct. 10, 2017, pp. 1-3.
Final Office Action issued in U.S. Appl. No. 13/123,835; dated Feb. 12, 2013, pp. 1-13.
Non-Final Rejection issued in U.S. Appl. No. 13/382,442; dated Sep. 20, 2017, pp. 1-28.
Final Office Action from U.S. Appl. No. 12/617,805; dated Jan. 12, 2012, pp. 1-14.
Non-Final Rejection issued is U.S. Appl. No. 15/595,929; dated Sep. 20, 2017, pp. 1-9.
Final Rejection issued in U.S. Appl. No. 14/172,151; dated Jul. 20, 2015, pp. 1-18.
Final Rejection issued in U.S. Appl. No. 13/700,631; dated Apr. 13, 2015, pp. 1-19.
Non-Final Rejection issued in U.S. Appl. No. 15/237,285; dated Sep. 29, 2017, pp. 1-10.
Non-Final Rejection issued in U.S. Appl. No. 15/144,270; dated Dec. 13, 2017, pp. 1-25.
Final-Rejection issued in U.S. Appl. No. 13/432,811; dated Dec. 12, 2014, pp. 1-8.
Final Rejection issued in U.S. Appl. No. 13/469,633; dated Jan. 23, 2015, pp. 1-12.
Non-Final Office Action issued in U.S. Appl. No. 15/146,255; dated Sep. 18, 2017, pp. 1-10.
Final Rejection in U.S. Appl. No. 13/633,563; dated Apr. 28, 2017, pp. 1-12.
Non-Final Rejection issued in U.S. Appl. No. 14/995,910; dated Dec. 11, 2017, pp. 1-7.
Non-Final Rejection issued in U.S. Appl. No. 15/073,364; dated Nov. 9, 2017, pp. 1-8.
Extended European Search Report for European Application No. 16 19 0103.8; dated Jun. 23, 2017, pp. 1-5.
Extended European Search Report for European Application No. 17 20 2727.8; dated Dec. 20, 2017, pp. 1-9.
Search Report in Chinese Patent Application No. 201410818149.0; dated Jan. 10, 2017, pp. 1-3. English translation submitted.
U.S. Appl. No. 13/123,835, filed Sep. 30, 2011, Werner et al.
U.S. Appl. No. 15/803,589, filed Nov. 3, 2017, Hagendorf et al.
U.S. Appl. No. 14/172,151, filed Feb. 4, 2014, Bley et al.
U.S. Appl. No. 12/617,805, filed Nov. 13, 2009, Silvestre et al.
U.S. Appl. No. 12/617,811, filed Nov. 13, 2009, Silvestre et al.
U.S. Appl. No. 14/220,562, filed Mar. 20, 2014, Becker et al.
U.S. Appl. No. 13/700,631, filed Dec. 28, 2012, Becker et al.
U.S. Appl. No. 13/819,114, filed Apr. 29, 2013, Boka et al.
U.S. Appl. No. 13/363,956, filed Feb. 1, 2012, Silvestre et al.
U.S. Appl. No. 13/432,811, filed Mar. 28, 2012, Boka et al.
U.S. Appl. No. 13/469,633, filed May 11, 2012, Ruus et al.
U.S. Appl. No. 13/467,707, filed May 9, 2012, Niemoller et al.
U.S. Appl. No. 15/730,033, filed Oct. 11, 2017, Niemoller et al.
U.S. Appl. No. 13/468,422, filed May 10, 2012, Silvestre et al.
U.S. Appl. No. 13/467,757, filed May 9, 2012, Silvestre et al.
U.S. Appl. No. 13/595,590, filed Aug. 27, 2012, Niemoller et al.
U.S. Appl. No. 13/602,913, filed Sep. 4, 2012, Hess et al.
U.S. Appl. No. 13/633,563, filed Oct. 2, 2012, Stechl et al.
U.S. Appl. No. 13/633,496, filed Oct. 2, 2012, Stechl et al.
U.S. Appl. No. 13/661,476, filed Oct. 26, 2012, Silvestre et al.
U.S. Appl. No. 14/303,895, filed Jun. 13, 2014, Souhami et al.
U.S. Appl. No. 15/340,969, filed Nov. 1, 2016, Werner et al.
U.S. Appl. No. 15/595,929, filed May 15, 2017, Brunner-Schwarz et al.
U.S. Appl. No. 15/275,867, filed Sep. 26, 2016, Silvestre et al.
U.S. Appl. No. 15/237,285, filed Aug. 15, 2016, Boka et al.
U.S. Appl. No. 15/411,557, filed Jan. 20, 2017, Boka et al.
U.S. Appl. No. 15/197,378, filed Jun. 29, 2016, Niemöller et al.
U.S. Appl. No. 15/657,683, filed Jul. 24, 2017, Souhami et al.
U.S. Appl. No. 15/646,760, filed Jul. 11, 2017, Roy et al.
U.S. Appl. No. 15/146,255, filed May 4, 2016, Hess et al.
U.S. Appl. No. 15/144,270, filed May 20, 2016, Silvestre et al.

\* cited by examiner

PHARMACEUTICAL COMPOSITION COMPRISING A GLP-1 AGONIST, AN INSULIN AND METHIONINE

The present application relates to a liquid composition comprising a GLP-1 agonist or/and a pharmacologically tolerable salt thereof, an insulin or/and a pharmacologically tolerable salt thereof, and, optionally, at least one pharmaceutically acceptable excipient, wherein the composition comprises methionine.

The present application further relates to the composition according to the present invention for treating diabetes mellitus. The present application further relates to the use of a composition according to the present invention in the manufacture of a pharmaceutical for treating diabetes mellitus. The present application further relates to a method for manufacturing a composition according to the present invention, comprising formulating a GLP-1 agonist or/and a pharmacologically tolerable salt thereof with an insulin or/and a pharmaceutically acceptable salt thereof, methionine, and, optionally, at least one pharmaceutically acceptable excipient. The present application further relates to a method for treating a patient with a composition according to the present invention, comprising administering the composition to the patient.

Customary compositions of insulin and GLP-1 compounds comprise an isotonicity agent, a buffer for adjusting the pH, and a preservative. A further frequently used constituent of insulin compositions is zinc, which forms a complex with insulin. This results in a delayed action of insulin being achieved.

WO 2003/020201 (Eli Lilly) relates to a liquid pre-mixed formulation comprising a GLP-1 compound and a basal insulin. A specific formulation contains Val$^8$-GLP-1 or exendin-4, insulin NPH, glycerol as an isotonicity agent, m-cresol and phenol as preservatives, and a phosphate buffer at a pH of 7.6 or 8. Another formulation comprises exendin-4 or Val$^8$-Glu$^{22}$GLP-1(7-37)OH, insulin glargine (Lantus), zinc, glycerol and mannitol as isotonicity agents, m-cresol as a preservative, zinc, and sodium acetate, pH 4.

WO 2004/035623 (Zealand Pharmaceuticals) discloses a liquid composition comprising a stabilized exendin, 50 mM histidine, 100 to 200 mM sucrose, mannitol or other acceptable sugar, 20 mM methionine, 20 mM asparagine-glutamine or Asp, at a pH of 5.3. Stabilization is effected by certain modifications of the amino acid building blocks of exendin-4(1-39), for example, at positions Gln13, Met14, Trp25, or Asn28. This composition does not comprise insulin.

WO 2005/046716 (Novo Nordisk) discloses liquid compositions which comprise liraglutide and insulin aspart, a buffer with a pH of 7.7, poloxamer 188 as a surfactant, phenol, propylene glycol, and, optionally, zinc. Without poloxamer 188, the compositions were unstable. With polysorbate 20, stabilization was achieved.

WO 2006/029634 (Novo Nordisk) relates to liquid pharmaceutical compositions which comprise an insulinotropic peptide (GLP-1 agonist), an insulin peptide, and a ligand for His$^{B10}$ (ligand of His at position 10 of the B chain of insulin). The composition can comprise polysorbate-20 or poloxamer 188 as a surfactant. Specific compositions disclosed in this document comprise human insulin or human B28 Asp insulin (insulin aspart), liraglutide (GLP-1 agonist), glycerol as an isotonicity agent, zinc acetate, pH 7.4 or 7.9. Depending on the amount of insulin used or of liraglutide, these compositions were, in part, already unstable after 15 days of storage at room temperature. Stability of these compositions was achieved by adding a ligand for His$^{B10}$. Further formulations consisted of liraglutide, insulin aspart or detemir, propylene glycol, phenol, and phosphate buffer, pH 7.7. These compositions were practically immediately unstable. Adding poloxamer-188 or polysorbate-20 and a ligand for His$^{B10}$ led to stabilization.

WO 2006/051103 (Novo Nordisk) discloses liquid compositions which comprise detemir (a basal insulin), liraglutide (GLP-1 compound), and poloxamer 188 or polysorbate 20 as a surfactant. Further constituents are phenol, NaCl, propylene glycol, zinc acetate, and sodium phosphate buffer or glycylglycine buffer (pH 7.7). m-Cresol is present in some of these compositions. By adding poloxamer 188 or polysorbate 20, the compositions could be stabilized.

WO 2008/124522 (Biodel) relates to compositions which comprise an insulin, a zinc chelator (e.g., EDTA or EGTA), and a GLP-1 analog.

About 120 million people around the world suffer from diabetes mellitus. These include about 12 million type I diabetics, for whom replacement of the deficient endocrine insulin secretion is the only possible therapy at present. Those affected are dependent on insulin injections for life, usually several times a day. Type II diabetes contrasts with type I diabetes in that there is not always a deficiency of insulin, but in a large number of cases, especially at the advanced stage, treatment with insulin, where appropriate in combination with an oral antidiabetic, is considered the most advantageous form of therapy.

In healthy individuals, release of insulin by the pancreas is strictly coupled to the blood glucose concentration. Elevated blood glucose levels, like those occurring after meals, are quickly compensated by a corresponding rise in insulin secretion. In the fasting state, the plasma insulin level falls to a basal value which is sufficient to ensure a continuous supply of glucose to insulin-sensitive organs and tissues, and to keep hepatic glucose production low in the night. The replacement of the endogenous insulin secretion by exogenous, usually subcutaneous administration of insulin does not in general come close to the above-described quality of the physiological regulation of blood glucose. Frequently there are instances of blood glucose being thrown off-track, either upwardly or downwardly, and in their most severe forms these instances may be life-threatening. In addition, however, blood glucose levels which are elevated over years, without initial symptoms, constitute a considerable health risk. The large-scale DCCT study in the USA (The Diabetes Control and Complications Trial Research Group (1993), N. Engl. J. Med. 329, 977-986) showed unambiguously that chronically elevated blood glucose levels are responsible for the development of late diabetic complications. Late diabetic complications are microvascular and macrovascular damage which is manifested in certain circumstances as retinopathy, nephropathy, or neuropathy, and leads to blindness, renal failure, and loss of extremities, and, in addition, is associated with an increased risk of cardiovascular disorders. From this it can be inferred that an improved therapy of diabetes must be aimed primarily at keeping blood glucose as closely as possible within the physiological range. According to the concept of intensified insulin therapy, this is to be achieved by means of injections, several times a day, of fast-acting and slow-acting insulin preparations. Fast-acting formulations are given at meal times, in order to compensate the postprandial rise in blood glucose. Slow-acting basal insulins are intended to ensure the basic supply of insulin, especially during the night, without leading to hypoglycemia.

Insulin is a polypeptide composed of 51 amino acids which are divided between two amino acid chains: the A chain, with 21 amino acids, and the B chain, with 30 amino acids. The chains are linked together by 2 disulfide bridges. Insulin preparations have been employed for many years in diabetes therapy. Such preparations use not only naturally occurring insulins but also, more recently, insulin derivatives and insulin analogs.

Insulin analogs are analogs of naturally occurring insulins, namely human insulin or animal insulins, which differ by replacement of at least one naturally occurring amino acid residue by other amino acids and/or by addition/deletion of at least one amino acid residue, from the corresponding, otherwise identical, naturally occurring insulin. The amino acids in question may also be amino acids which do not occur naturally.

Insulin derivatives are derivatives of naturally occurring insulin or of an insulin analog which are obtained by chemical modification. The chemical modification may consist, for example, in the addition of one or more defined chemical groups onto one or more amino acids. Generally speaking, the activity of insulin derivatives and insulin analogs is somewhat altered as compared with human insulin.

Insulin analogs with an accelerated onset of action are described in EP 0 214 826, EP 0 375 437, and EP 0 678 522. EP 0 124 826 relates, among other things, to replacements of B27 and B28. EP 0 678 522 describes insulin analogs which have different amino acids in position B29, preferably proline, but not glutamic acid. EP 0 375 437 encompasses insulin analogs with lysine or arginine at B28, which may optionally also be modified at B3 and/or A21.

EP 0 419 504 discloses insulin analogs which are protected from chemical modifications by modification of asparagine in B3 and of at least one further amino acid at positions A5, A15, A18 or A21.

WO 92/00321 describes insulin analogs in which at least one amino acid in positions B1-B6 has been replaced by lysine or arginine. Such insulins, according to WO 92/00321, have an extended effect. A delayed effect is also exhibited by the insulin analogs described in EP-A 0 368 187.

The commercially available preparations of naturally occurring insulins for insulin replacement differ in the origin of the insulin (e.g., bovine, porcine, human insulin) and also in their composition, and thereby the activity profile (onset and duration of action) may be influenced. Through combination of different insulin products it is possible to obtain any of a very wide variety of activity profiles and to bring about very largely physiological blood sugar values. Recombinant DNA technology nowadays allows the preparation of modified insulins of this kind. They include insulin glargine (Gly(A21)-Arg(B31)-Arg(B32) human insulin, Lantus), with an extended duration of action. Insulin glargine is injected in the form of a clear, acidic solution, and owing to its dissolution properties is precipitated, in the physiological pH range of the subcutaneous tissue, as a stable hexamer association. Insulin glargine is injected once a day and is notable in comparison with other long-active insulins for its flat serum profile and the associated reduction in the risk of night hypoglycemias (Schubert-Zsilavecz et al., 2:125-130 (2001)).

The specific preparation of insulin glargine that leads to the prolonged duration of action is characterized by a clear solution with an acidic pH.

Exendins are a group of peptides which can lower blood glucose concentrations. Exendins have a certain similarity to the sequence of GLP-1(7-36) (53%, Goke et al. J. Biol Chem 268, 19650-55). Exendin-3 and exendin-4 stimulate an increase in cellular cAMP production in the acinar cells of the guinea pig pancreas by interacting with exendin receptors (Raufman, 1996, Reg. Peptides 61:1-18). Exendin-3, in contrast to exendin-4, effects an increase in the release of amylase in the acinar cells of the pancreas. Exendins act as GLP-1 agonists.

Glucagon-like peptide 1 (GLP-1) is an endocrine hormone which enhances the insulin response following oral intake of glucose or fat. In general, GLP-1 lowers glucagon concentrations, slows gastric emptying, stimulates (pro) insulin synthesis, enhances sensitivity to insulin, and stimulates insulin-independent glycogen synthesis (Hoist (1999), Curr. Med. Chem. 6:1005, Nauck et al. (1997) Exp Clin Endocrinol Diabetes 105: 187, Lopez-Delgado et al. (1998) Endocrinology 139:2811). Human GLP-1 has 37 amino acid residues (Heinrich et al., Endocrinol. 115:2176 (1984), Uttenthal et al., J Clin Endocrinol Metabol (1985) 61:472). Active fragments of GLP-1 include GLP-1 (7-36) and GLP-1(7-37).

Exendin-3, exendin-4 and exendin agonists have been proposed for treating diabetes mellitus and preventing hyperglycemia, by reducing gastric motility and gastric emptying (U.S. Pat. No. 5,424,286 and WO98/05351).

Exendin analogs can be characterized by amino acid substitutions and/or C-terminal truncation of the native exendin-4 sequence. Such exendin analogs are described in WO 99/07404, WO 99/25727, and WO 99/25728.

Solid-phase synthesis of AVE0010 is described in WO 01/04156 A1. AVE0010 has the sequence: desPro$^{36}$exendin-4(1-39)-Lys$_6$-NH$_2$. This substance is published as SEQ ID NO:93 in WO 01/04156:

(SEQ ID NO: 1)
H-G-E-G-T-F-T-S-D-L-S-K-Q-M-E-E-A-V-R-L-F-I-E-

W-L-K-N-G-G-P-S-S-G-A-P-P-S-K-K-K-K-K-K-NH$_2$

Exendin-4 (39 AS) has the sequence:

(SEQ ID NO: 2)
H-G-E-G-T-F-T-S-D-L-S-K-Q-M-E-E-A-V-R-L-F-I-E-

W-L-K-N-G-G-P-S-S-G-A-P-P-P-S-NH$_2$

Exendin-3 has the sequence (J. Bio. Chem., 267, 1992, 7402-7405):

(SEQ ID NO: 3)
H-His-Ser-Asp-Gly-Thr-Phe-Thr-Ser-Asp-Leu-Ser-Lys-

Gln-Met-Glu-Glu-Glu-Ala-Val-Arg-Leu-Phe-Ile-Glu-

Trp-Leu-Lys-Asn-Gly-Gly-Pro-Ser-Ser-Gly-Ala-Pro-

Pro-Pro-Ser-NH$_2$

GLP-1 has the sequence:

(SEQ ID NO: 4)
H-A-E-G-T-F-T-S-D-V-S-S-Y-L-E-G-Q-A-A-K-E-F-I-A-W-

L-V-K-G-R-NH$_2$

It is an object of the present invention to increase the stability of liquid formulations comprising a GLP-1 agonist and an insulin. More particularly, it is an object of the present invention to improve physical and chemical integrity. We have found that this object is achieved by formulating the GLP-1 agonist and the insulin with methionine.

It was found that methionine is able to increase the storage stability of a composition comprising a GLP-1 agonist such as AVE0010 and an insulin such as insulin glargine. Methionine does not affect the physical integrity of these compositions.

The stability of pharmaceutically active polypeptides can be impaired by various mechanisms. These include pH, temperature, light, and the effects of certain constituents.

In connection with the present invention, it was found that a range of customary constituents of insulin formulations or of formulations of GLP-1 agonists are disadvantageous for the chemical or/and physical integrity and the storage stability of formulations which comprise an insulin and a GLP-1 agonist. These are, for example, acetate, polysorbate 20, polysorbate 80, poloxamer 188, benzalkonium chloride, and lysine. The compositions according to the present invention are therefore preferably free of these constituents.

The present invention accordingly provides for a liquid composition comprising a GLP-1 agonist or/and a pharmacologically tolerable salt thereof, an insulin or/and a pharmacologically tolerable salt thereof, and, optionally, at least one pharmaceutically acceptable excipient, wherein the composition comprises methionine.

The composition according to the present invention preferably comprises methionine in an amount ranging from 0.5 mg/mL to 20 mg/mL, more preferably in an amount ranging from 1 mg/mL to 5 mg/mL, especially preferably in an amount of 3.0 mg/mL. Methionine in the D-form can be used. Likewise, methionine in the L-form can be used. Likewise, mixtures of the D-form and the L-form in any desired proportions can be used.

More particularly, the composition according to the present invention is free of surfactants, such as polyols and partial and fatty acid esters and ethers of polyhydric alcohols such as those of glycerol and sorbitol. The compositions according to the present invention are more particularly free of partial and fatty acid esters and ethers of glycerol and sorbitol selected from the group consisting of Span®, Tween®, Myrj®, Brij®, Cremophor®. Furthermore, the compositions according to the present invention are more particularly free of polyols selected from the group consisting of polypropylene glycols, polyethylene glycols, poloxamers, Pluronics, Tetronics. More particularly, the composition according to the present invention is free of at least one substance selected from the group consisting of polysorbate, polysorbate and poloxamer.

More particularly, the composition according to the present invention is substantially free, preferably free, of polysorbate, such as, for example, polysorbate 20.

More particularly, the composition according to the present invention is substantially free, preferably free, of polysorbate 80.

More particularly, the composition according to the present invention is substantially free, preferably free, of poloxamer, such as, for example, poloxamer 188.

More particularly, the composition according to the present invention is substantially free, preferably free, of benzalkonium chloride.

More particularly, the composition according to the present invention is substantially free, preferably free, of histidine.

More particularly, the composition according to the present invention is substantially free, preferably free, of EDTA, more particularly sodium EDTA.

More particularly, the composition according to the present invention is substantially free, preferably free, of histidine and sodium EDTA.

The composition according to the present invention can comprise one or more substances which are customarily used to buffer the pH (buffer substances). Examples of such buffer substances are acetate, citrate, and phosphate. More particularly, the composition according to the present invention can comprise one or more substances which are customarily used to buffer the pH in an amount which is sufficient, for example, as a counterion for the GLP-1 agonist or/and the insulin. The composition according to the present invention can comprise one or more buffer substances, for example, each in an amount of up to 1 mg/ml, up to 0.5 mg/ml, up to 0.1 mg/ml, up to 0.05 mg/ml, up to 0.02 mg/ml, or up to 0.01 mg/ml. The composition according to the present invention can likewise be substantially free of buffer substances. Preferably, the composition according to the present invention is free of buffer substances.

The composition according to the present invention can comprise acetate, for example, in an amount of up to 1 mg/ml, up to 0.5 mg/ml, up to 0.1 mg/ml, up to 0.05 mg/ml, up to 0.02 mg/ml, or up to 0.01 mg/ml. These amounts are, for example, sufficient as a counterion for the GLP-1 agonist. Likewise, the composition according to the present invention can be substantially free of acetate. Preferably, the composition according to the present invention is free of acetate.

The composition according to the present invention can comprise citrate, for example, in an amount of up to 1 mg/ml, up to 0.5 mg/ml, up to 0.1 mg/ml, up to 0.05 mg/ml, up to 0.02 mg/ml, or up to 0.01 mg/ml. These amounts are, for example, sufficient as a counterion for the GLP-1 agonist. Likewise, the composition according to the present invention can be substantially free of citrate. Preferably, the composition according to the present invention is free of citrate.

The composition according to the present invention can comprise phosphate, for example, in an amount of up to 1 mg/ml, up to 0.5 mg/ml, up to 0.1 mg/ml, up to 0.05 mg/ml, up to 0.02 mg/ml, or up to 0.01 mg/ml. These amounts are, for example, sufficient as a counterion for the GLP-1 agonist. Likewise, the composition according to the present invention can be substantially free of phosphate. Preferably, the composition according to the present invention is free of phosphate.

The pharmaceutical composition of the present invention can have an acidic or physiological pH. An acidic pH range is preferably in the range of pH 1-6.8, pH 3.5-6.8, or pH 3.5-5. A physiological pH is preferably in the range of pH 2.5-8.5, more preferably pH 4.0 to 8.5, even more preferably pH 6.0 to 8.5. Especially preferred is a pH of approximately 4.5. For pH adjustment, physiologically safe dilute acids (typically HCl) and alkalis (typically NaOH) are suitable.

The composition according to the present invention can comprise a suitable preservative. Suitable preservatives are, for example, phenol, m-cresol, benzyl alcohol, and/or p-hydroxybenzoate esters. m-Cresol is preferred. However, a preservative can also be omitted.

The composition according to the present invention can comprise zinc ions. The concentration of the zinc ions is preferably in the range from 1 µg/ml to 2 mg/ml, more preferably in the range from 5 µg to 200 µg zinc/ml, more particularly at a maximum of 0.06 mg/ml, especially preferably at 0.06 mg/ml.

Furthermore, the composition according to the present invention can comprise suitable isotonicity agents. Suitable isotonicity agents are, for example, glycerol, dextrose, lactose, sorbitol, mannitol, glucose, NaCl, calcium or magnesium compounds such as CaCl$_2$ etc. The concentrations of glycerol, dextrose, lactose, sorbitol, mannitol, and glucose are customarily in the range of 100-250 mM, NaCl in a concentration of up to 150 mM. Glycerol is preferred. More particularly, 85% glycerol at 20.0 mg/ml is preferred.

The composition according to the present invention can further comprise further additives, such as salts, which retard the release of at least one insulin, Preferably, the composition is free of these additives.

More particularly, the composition is intended for parenteral administration. The composition according to the present invention is preferably an injectable composition, more preferably for subcutaneous injection. More particularly, the composition of the present invention is suitable for injection once a day.

More particularly, the formulation according to the present invention has, after storage for 1 month, 2 months, 4 months, or 6 months at a temperature of +5° C. or 25° C., an activity of at least 80%, at least 90%, at least 95%, or at least 98% of the activity at the start of storage.

In the present application, "activity" can mean the activity of the insulin which is used in the formulation according to the present invention. Methods for determining the activity of insulin are known to a person skilled in the art.

In the present application, "activity" can likewise mean the activity of the GLP-1 agonist which is used in the formulation according to the present invention. Methods for determining the activity of a GLP-1 agonist are known to a person skilled in the art.

More particularly, the formulation according to the present invention exhibits chemical integrity after storage for 1 month, 2 months, 4 months, or 6 months. Chemical integrity means, more particularly, that after storage at a temperature of +5° C., 25° C., or 40° C. the formulation comprises at least 80%, at least 90%, at least 95%, or at least 98% of the active ingredient, compared with the start of storage, in a substantially chemically unchanged form.

Chemical integrity can mean the chemical integrity of the GLP-1 agonist. GLP-1 agonists may comprise a methionine residue (e.g. position 14 in AVE0010). Chemical integrity of the GLP-1 agonist means, more particularly, that oxidation of the methionine residue is prevented.

Chemical integrity can likewise mean the chemical integrity of the insulin.

Preferably, chemical integrity means the integrity of the insulin and the GLP-1 agonist.

More particularly, the formulation according to the present invention exhibits physical integrity after storage for 1 month, 2 months, 4 months, or 6 months. Physical integrity means, more particularly, that after storage at a temperature of +5° C., 25° C., or 40° C. the formulation comprises at least 80%, at least 90%, at least 95%, or at least 98% of the active ingredient, compared with the start of storage, in a substantially physically unchanged form.

Physical integrity can mean the integrity of the GLP-1 agonist. Likewise, physical integrity can mean the integrity of the insulin. Physical integrity means, more particularly, that the GLP-1 agonist or/and the insulin does/do not form aggregates, such as, for example, fibrils.

Preferably, physical integrity means the integrity of the insulin and the GLP-1 agonist.

The GLP-1 agonist is preferably selected from the group consisting of exendin-3 and analogs and derivates thereof, exendin-4 and analogs and derivates thereof, and in which case the GLP-1 agonist is more preferably selected from the group consisting of AVE0010 and exendin-4.

Exendin-3, analogs and derivates of exendin-3, exendin-4, and analogs and derivates of exendin-4 can be found in WO 01/04156, WO 98/30231, U.S. Pat. No. 5,424,286, EP application 99 610043.4, and WO 2004/005342. These documents are incorporated herein by reference. The exendin-3, exendin-4, and analogs and derivates thereof described in these documents can be synthesized by means of the methods described therein, after which modifications are optionally carried out.

The sequences of AVE0010 (SEQ ID NO:1), exendin-4 (SEQ ID NO:2), and exendin-3 (SEQ ID NO:3) show a high degree of similarity. The sequences of AVE0010 and exendin-4 are identical at positions 1-37. Sequence 1-39 from exendin-4 is at 37 of the 39 positions (94%) identical to the exendin-3 sequence at positions 48-86. With reference to the sequences, a person skilled in the art can readily convert the positions specified herein, which relate to a particular sequence (e.g. to the sequence of AVE0010 or exendin-4), to other sequences.

Analogs and derivates of exendin-3 or/and exendin-4 contain more particularly a modified amino acid sequence. For example, single amino acids can be deleted (e.g. desPro36, desPro37, desAsp28, desMet(O) 14 in exendin-4 and the corresponding positions in exendin-3). Likewise, single positions can be substituted (e.g. Met(O)$^{14}$, Trp(O$_2$)$^{25}$, IsoAsp$^{28}$, Asp$^{28}$ Pro$^{38}$ in exendin-4 and the corresponding positions in exendin-3), in which case unnatural amino acids such as Met(O) (methionine sulfoxide or methionine sulfone), Trp(O$_2$) (N-formylkynurenine), or/and IsoAsp (β-aspartate or isoaspartate) can also be used. Unnatural amino acids can be readily inserted, in the form of corresponding amino acid building blocks, into the sequence.

Furthermore, the C-terminus or/and the N-terminus can be modified, for example, by an additional sequence such as -(Lys)-, -(Lys)$_2$-, -(Lys)$_3$-, -(Lys)$_4$-, -(Lys)$_5$-, -(Lys)$_6$-, -Asn-(Glu)$_5$-, in which case -(Lys)$_4$-, -(Lys)$_5$-, -(Lys)$_6$-, -Asn-(Glu)$_5$- are preferred. The carboxyl group at the C-terminus is preferably modified to an amide group (—NH$_2$). Optionally, modification of the C-terminus or/and of the N-terminus is carried out as a further step after completion of synthesis.

Pharmaceutically tolerable salts can be manufactured in a further step after completion of the synthesis cycles of the method according to the present invention. The manufacture of pharmaceutically tolerable salts of peptides is known to a person skilled in the art. A preferred pharmaceutically tolerable salt is acetate.

The GLP-1 agonist is preferably selected from the group consisting of exendin-4, analogs and derivates of exendin-4, and pharmacologically tolerable salts thereof.

A further preferred GLP-1 agonist is an analog of exendin-4 selected from the group consisting of:
H-desPro$^{36}$-exendin-4-Lys$_6$-NH$_2$,
H-des(Pro$^{36,37}$)-exendin-4-Lys$_4$-NH$_2$,
H-des(Pro$^{36,37}$)-exendin-4-Lys$_5$-NH$_2$ and pharmacologically tolerable salts thereof.

A further preferred GLP-1 agonist is an analog of exendin-4 selected from the group consisting of:
des Pro$^{36}$[Asp$^{28}$]exendin-4 (1-39),
desPro$^{36}$[IsoAsp$^{28}$]exendin-4 (1-39),
desPro$^{36}$[Met(O)$^{14}$,Asp$^{28}$]exendin-4 (1-39),
desPro$^{36}$[Met(O)$^{14}$,IsoAsp$^{28}$]exendin-4 (1-39),
desPro$^{36}$[Trp(O$_2$)$^{25}$,Asp$^{28}$]exendin-2 (1-39),
desPro$^{36}$[Trp(O$_2$)$^{25}$,IsoAsp$^{28}$]exendin-2 (1-39), desPro$^{36}$[Met(O)$^{14}$Trp(O$_2$)$^{26}$,Asp$^{28}$]exendin-4 (1-39),
desPro$^{36}$[Met(O)$^{14}$Trp(O$_2$)$^{25}$,IsoAsp$^{28}$]exendin-4(1-39) and pharmacologically tolerable salts thereof.

A further preferred GLP-1 agonist is an analog of exendin-4 selected from a group as described in the previous paragraph, wherein the peptide -Lys$_6$-NH$_2$ is attached to the C-termini of the analogs of exendin-4.

A further preferred GLP-1 agonist is an analog of exendin-4 selected from the group consisting of:
H-(Lys)$_6$-desPro$^{36}$[Asp$^{28}$]exendin-4(1-39)-Lys$_6$-NH$_2$,
desAsp$^{28}$Pro$^{36}$,Pro$^{37}$,Pro$^{38}$exendin-4(1-39)-NH$_2$,
H-(Lys)$_6$-desPro$^{36}$,Pro$^{37}$,Pro$^{38}$[Asp$^{28}$]exendin-4(1-39)-NH$_2$,
H-Asn-(Glu)$_5$desPro$^{36}$,Pro$^{37}$,Pro$^{38}$[Asp$^{28}$]exendin-4(1-39)-NH$_2$,
desPro$^{36}$,Pro$^{37}$,Pro$^{38}$[Asp$^{28}$]exendin-4(1-39)-(Lys)$_6$-NH$_2$,
H-(Lys)$_6$-desPro$^{36}$,Pro$^{37}$,Pro$^{38}$[Asp$^{28}$]exendin-4(1-39)-(Lys)$_6$-NH$_2$,
H-Asn-(Glu)$_5$-desPro$^{36}$,Pro$^{37}$,Pro$^{38}$[Asp$^{28}$]exendin-4(1-39)-(Lys)$_6$-NH$_2$,
H-(Lys)$_6$-desPro$^{36}$[Trp(O$_2$)$^{26}$,Asp$^{28}$]exendin-4(1-39)-Lys$_6$-NH$_2$,
H-desAsp$^{28}$Pro$^{36}$,Pro$^{37}$,Pro$^{38}$[Trp(O$_2$)$^{25}$]exendin-4(1-39)-NH$_2$,
H-(Lys)$_6$-desPro$^{36}$,Pro$^{37}$,Pro$^{38}$[Trp(O$_2$)$^{26}$,Asp$^{28}$]exendin-4(1-39)-NH$_2$,
H-Asn-(Glu)$_5$-desPro$^{36}$,Pro$^{37}$,Pro$^{38}$[Trp(O$_2$)$^{25}$,Asp$^{28}$]exendin-4(1-39)-NH$_2$,
desPro$^{36}$,Pro$^{37}$,Pro$^{38}$[Trp(O$_2$)$^{25}$,Asp$^{28}$]exendin-4(1-39)-(Lys)$_6$-NH$_2$,
H-(Lys)$_6$-desPro$^{36}$,Pro$^{37}$,Pro$^{38}$[Trp(O$_2$)$^{25}$,Asp$^{28}$]exendin-4(1-39)-(Lys)$_6$-NH$_2$,
H-Asn-(Glu)$_5$-desPro$^{36}$,Pro$^{37}$,Pro$^{38}$[Trp(O$_2$)$^{25}$,Asp$^{28}$]exendin-4(1-39)-(Lys)$_6$-NH$_2$,
H-(Lys)$_6$-desPro$^{36}$[Met(O)$^{14}$,Asp$^{28}$]exendin-4(1-39)-Lys$_6$-NH$_2$,
desMet(O)$^{14}$ Asp$^{28}$ Pro$^{36}$,Pro$^{37}$,Pro$^{38}$exendin-4(1-39)-NH$_2$,
H-(Lys)$_6$-desPro$^{36}$, Pro$^{37}$,Pro$^{38}$[Met(O)$^{14}$,Asp$^{28}$]exendin-4(1-39)-NH$_2$,
H-Asn-(Glu)$_5$-desPro$^{36}$,Pro$^{37}$,Pro$^{38}$[Met(O)$^{14}$,Asp$^{28}$]exendin-4(1-39)-NH$_2$,
desPro$^{36}$,Pro$^{37}$,Pro$^{38}$[Met(O)$^{14}$,Asp$^{28}$]exendin-4(1-39)-(Lys)$_6$-NH$_2$,
H-(Lys)$_6$-desPro$^{36}$,Pro$^{37}$,Pro$^{38}$[Met(O)$^{14}$,Asp$^{28}$]exendin-4(1-39)-Lys$_6$-NH$_2$,
H-Asn-(Glu)$_5$-desPro$^{36}$,Pro$^{37}$,Pro$^{38}$[Met(O)$^{14}$,Asp$^{28}$]exendin-4(1-39)-(Lys)$_6$NH$_2$,
H-(Lys)$_6$-desPro$^{36}$[Met(O)$^{14}$, Trp(O$_2$)$^{26}$,Asp$^{28}$]exendin-4(1-39)-Lys$_6$-NH$_2$,
desAsp$^{28}$Pro$^{36}$,Pro$^{37}$,Pro$^{38}$[Met(O)$^{14}$, Trp(O$_2$)$^{25}$]exendin-4(1-39)-NH$_2$,
H-(Lys)$_6$-desPro$^{36}$,Pro$^{37}$,Pro$^{38}$[Met(O)$^{14}$, Trp(O$_2$)$_{25}$,Asp$^{28}$]exendin-4(1-39)-NH$_2$,
H-Asn-(Glu)$_5$-desPro$^{36}$,Pro$^{37}$,Pro$^{38}$[Met(O)$^{14}$,Asp$^{8}$]exendin-4(1-39)-NH$_2$,
desPro$^{36}$,Pro$^{37}$,Pro$^{38}$[Met(O)$^{14}$, Trp(O$_2$)$^{25}$,Asp$^{28}$]exendin-4(1-39)-(Lys)$_6$NH$_2$,
H-(Lys)$_6$-desPro$^{36}$,Pro$^{37}$,Pro$^{38}$[Met(O)$^{14}$,Trp(O$_2$)$^{25}$,Asp$^{28}$]exendin-4(1-39)-(Lys)$_6$-NH$_2$,
H-Asn-(Glu)$_5$-desPro$^{36}$,Pro$^{37}$,Pro$^{38}$[Met(O)$^{14}$,Trp(O$_2$)$^{25}$, Asp$^{28}$]exendin-4(1-39)-(Lys)$_6$-NH$_2$ and pharmacologically tolerable salts thereof.

Likewise, the GLP-1 agonist can be selected from the group consisting of GLP-1 and analogs and derivates of GLP-1. A further preferred GLP-1 agonist is selected from the group consisting of Arg$^{34}$,Lys$^{26}$(N$^\epsilon$(γ-glutamyl(N$^\alpha$-hexadecanoyl)))GLP-1(7-37) [liraglutide] and a pharmacologically tolerable salt thereof.

A further preferred GLP-1 agonist is AVE0010. AVE0010 has the sequence desPro$^{36}$exendin-4(1-39)-Lys$_6$-NH$_2$ (SEQ ID NO:1). Likewise, pharmacologically tolerable salts of AVE0010 are preferred.

The GLP-1 agonist, for example AVE0010, is more particularly used in an amount ranging from 0.01 mg/ml to 0.5 mg/ml or 0.05 mg/ml to 1.5 mg/ml.

In the present application, the term "insulin" encompasses not only unmodified insulins but also insulin analogs, insulin derivatives, and insulin metabolites. The compositions according to the present invention comprise one or more independently selected from the group consisting of insulins (e.g., unmodified insulins), insulin analogs, insulin derivatives, and insulin metabolites, and any desired combinations thereof.

The at least one insulin may independently be selected from the group consisting of bovine insulins, analogs, derivatives, and metabolites thereof, porcine insulins, analogs, derivatives, and metabolites thereof, and human insulins, analogs, derivatives, and metabolites thereof. Preferably, the at least one insulin is independently selected from human insulins, analogs, derivatives, and metabolites thereof.

Furthermore, an insulin according to the present invention may be selected independently from unmodified insulins, more particularly from bovine insulins, porcine insulins, and human insulins.

The at least one insulin may independently be selected from the group consisting of bovine insulins, porcine insulins, and human insulins. More preferably, the at least one insulin is independently selected from human insulins. An insulin according to the present invention may be selected from unmodified insulins, more particularly from bovine insulins, porcine insulins, and human insulins.

Insulin derivatives according to the present invention are derivatives of a naturally occurring insulin and/or an insulin analog, which are obtained by chemical modification. The chemical modification may consist, for example, in the addition of one or more defined chemical groups onto one or more amino acids.

Insulin analogs which are described in EP 0 214 826, EP 0 375 437, EP 0 678 522, EP 0 419 504, WO 92/00321, EP-A 0 368 187, and WO2009/063072 may be part of the compositions according to the present invention. The documents EP 0 214 826, EP 0 375 437, EP 0 678 522, EP 0 419 504, WO 92/00321, EP-A 0 368 187, and WO 2009/063072 are included herein by reference.

One preferred insulin analog according to the present invention may be selected from the group consisting of Gly(A21)-Arg(B31)-Arg(B32) human insulin (insulin glargine), Lys(B3)-Glu(B29) human insulin; Lys$^{B28}$Pro$^{B29}$ human insulin (insulin lyspro), B28 Asp human insulin (insulin aspart), human insulin in which proline in position B28 has been substituted by Asp, Lys, Leu, Val or Ala and where Lys in position B29 may be substituted by Pro; AlaB26 human insulin; des(B28-B30) human insulin; des (B27) human insulin or B29Lys(ϵ-tetradecanoyl),des(B30) human insulin (insulin detemir), N$^{\epsilon B29}$-tetradecanoyl des (B30) human insulin, N$^{\epsilon B29}$-(N$^\alpha$-(HOOC(CH$_2$)$_{14}$CO)-γ-Glu) desB30 human insulin, Lys$^{B29}$(N$^\epsilon$ lithocholyl-γ-Glu)-des(B30) human insulin, N$^{\epsilon B29}$-ω-carboxypentadecanoyl-γ-L-glutaylamide desB30 human insulin, and N$^{\epsilon B29}$-ω-carboxypentadecanoyl-γ-amino-butanoyl des(B30) human insulin.

A preferred insulin derivative according to the present invention may be selected from the group consisting of B29-N-myristoyl-des(B30) human insulin, B29-N-palmitoyl-des(B30) human insulin, B29-N-myristoyl human insulin, B29-N-palmitoyl human insulin, B28-N-myristoyl $Lys^{B28}Pro^{B29}$ human insulin, B28-N-palmitoyl-$Lys^{B28}Pro^{B29}$ human insulin, B30-N-myristoyl-$Thr^{B29}Lys^{B30}$ human insulin, B30-N-palmitoyl-$Thr^{B29}Lys^{B39}$ human insulin, B29-N-(N-palmitoyl-Y-glutamyl)-des(B30) human insulin, B29-N-(N-lithocholyl-Y-glutamyl)-des(B30) human insulin, B29-N-(ω-carboxyheptadecanoyl)-des(B30) human insulin and B29-N-(ω-carboxyheptadecanoyl) human insulin, $N^{\epsilon B29}$-tetradecanoyl des(B30) human insulin, $N^{\epsilon B29}$-($N^{\alpha}$-(HOOC$(CH_2)_{14}$CO)-γ-Glu) des B30 human insulin, $Lys^{B29}(N^{\epsilon}$ lithocholyl-γ-Glu)-des(B30) human insulin, $N^{\epsilon B29}$-ω-carboxypentadecanoyl-γ-L-glutaylamide desB30 human insulin, and $N^{\epsilon B29}$-ω-carboxypentadecanoyl-γ-amino-butanoyl des(B30) human insulin.

A more highly preferred insulin derivative according to the present invention is selected from the group consisting of Gly(A21)-Arg(B31)-Arg(B32) human insulin, $Lys^{B28}Pro^{B29}$ human insulin (insulin lyspro), B28 Asp human insulin (insulin aspart), B29Lys(ε-tetradecanoyl),desB30 human insulin (insulin detemir).

The compositions according to the present invention contain 60-6000 nmol/ml, preferably 240-3000 nmol/ml, of an insulin as defined herein. Depending on the insulin used, a concentration of 240-3000 nmol/ml corresponds approximately to a concentration of 1.4-35 mg/ml or 40-500 units/ml.

The present invention particularly preferably provides a composition as described herein comprising at least one insulin independently selected from $Lys^{B28}Pro^{B29}$ human insulin (insulin lyspro), B28 Asp human insulin (insulin aspart), B29Lys(ε-tetradecanoyl),desB30 human insulin (insulin detemir), and insulin glargine (Gly(A21)-Arg(B31)-Arg(B32) human insulin), and comprising AVE0010 and/or a pharmacologically tolerable salt thereof. The present invention further particularly preferably provides a composition as described herein comprising insulin glargine (Gly(A21)-Arg(B31)-Arg(B32) human insulin) and AVE0010 (desPro$^{36}$exendin-4(1-39)-Lys$_6$-NH$_2$) and/or a pharmacologically tolerable salt thereof. These particularly preferred compositions preferably have an acidic pH of 1-6.8, more preferably pH 3.5-6.8, even more preferably pH 3.5-4.5.

In a particular embodiment, the formulation according to the present invention comprises the following constituents:
(a) desPro$^{36}$exendin-4(1-39)-Lys$_6$-NH$_2$,
(b) Gly(A21)-Arg(B31)-Arg(B32) human insulin,
(c) zinc chloride,
(d) m-cresol,
(e) L-methionine,
(f) glycerol,
(g) hydrochloric acid, if adjustment to a pH of approximately 4.5 is required,
(h) NaOH solution, if adjustment to a pH of approximately 4.5 is required, and
(i) water.

More particularly, the formulation according to the present invention consists of the constituents mentioned in (a) to (i). Optionally, m-cresol can be omitted. Hence the formulation according to the present invention then consists of constituents (a) to (c) and (e) to (i).

The present invention further provides a combination of at least two formulations according to the present invention. In this case, a first and a second composition and, optionally, at least one further pharmaceutical composition are provided, each comprising the insulin and the GLP-1 agonist.

Therefore, the present invention provides a combination comprising a first pharmaceutical composition and a second pharmaceutical composition, and, optionally, at least one further pharmaceutical composition, each comprising at least one insulin and at least one GLP-1 agonist, and containing the at least one insulin and/or the at least one GLP-1 agonist in different weight fractions relative to the total weight of the composition.

In the present application, "optionally, at least one further pharmaceutical composition" means that the combination according to the present invention, in addition to the first and second pharmaceutical compositions, may comprise at least one further pharmaceutical composition. Hence, the combination according to the present invention may comprise, for example, 3, 4, 5, 6, 7, 8, 9, 10 or more pharmaceutical compositions according to the present invention.

Preferred combinations are those which comprise a first and a second pharmaceutical composition according to the present invention.

Likewise preferred are combinations which comprise a first, a second, and a third pharmaceutical composition according to the present invention.

Likewise preferred are combinations which comprise a first, a second, a third, and a fourth pharmaceutical composition according to the present invention.

Likewise preferred are combinations which comprise a first, a second, a third, a fourth, and a fifth pharmaceutical composition.

The weight fractions of the at least one insulin and of the at least one GLP-1 agonist may be selected in the first pharmaceutical composition, the second pharmaceutical composition, and, where used, the at least one further pharmaceutical composition in such a way that the pharmaceutical compositions contain different ratios of insulin to GLP-1 agonist, based on the weight fraction.

In this case, the first composition may contain the smallest ratio and the second composition the next-greater ratio. Where at least one further composition is present, it may contain the next-greater ratio. Where a further composition is present as well, it may contain the next-greater ratio in turn. The compositions may therefore contain ratios of insulin to GLP-1 agonist, based on the weight fraction, that increase from the first to the second and, where used, further compositions.

The weight fraction of one of the two active ingredients, i.e., of the at least one insulin or of the at least one GLP-1 agonist, in the first pharmaceutical composition, the second pharmaceutical composition, and, where used, the at least one further pharmaceutical composition is preferably selected in each case such that the predetermined dose of this active ingredient can be administered by administering a defined volume of the first, second and/or at least one further composition. With particular preference, this active ingredient is the at least one insulin.

The weight fraction of the other of the two active ingredients, i.e., of the at least one insulin or of the at least one GLP-1 agonist, in the first pharmaceutical composition, the second pharmaceutical composition, and, where used, the at least one further pharmaceutical composition is preferably selected such that the ratios of insulin to GLP-1 agonist, based on the weight fraction, increase from the first to the second and, where used, further compositions. With particular preference, this active ingredient is the at least one GLP-1 agonist.

Furthermore, the weight fraction of the other of the two active ingredients in the pharmaceutical compositions is determined such that one of the pharmaceutical compositions can be selected in such a way that the dose of the first of the two active ingredients that is to be administered and the dose of the second active ingredient that is to be administered are given in a defined volume. Hence, a pharmaceutical composition is selected which contains the desired ratio.

Theoretically, it would be possible to provide a pharmaceutical composition for each individual therapeutically desired ratio of the weight fractions of the at least one insulin to the at least one GLP-1 agonist, in order to obtain an optimum dosage, tailored to requirements, for both active ingredients for every patient.

In the present invention, a particular number of pharmaceutical compositions is sufficient in order to cover the dosages needed in practice for the two active ingredients. For each patient, a defined dosage range is defined within a therapeutically rational interval for each of the two active ingredients. The dose to be administered ought hereby to fluctuate essentially within this dosage range for a particular patient, without any overdosing or underdosing.

Since it is primarily the amount of insulin that must be adapted and precisely dosed to the individual patient, the concentration range of the GLP-1 agonist allows a pharmaceutical composition according to the present invention that contains a defined ratio of at least one insulin to the at least one GLP-1 agonist to cover a therapeutic range of insulin doses simultaneously with the associated, synergistic amount of GLP-1 agonist. The ratio can be selected such that every desired insulin dose has its corresponding dose of the at least one GLP-1 agonist, which is situated within the desired range, e.g.; the synergistic range. As set out earlier on above, the ratios of the first, second, and, where used, at least one further composition of the pharmaceutical may also be chosen such that the ratios increase from the first to the second and, where used, the at least one further composition. If the dose of the GLP-1 agonist at the desired insulin dose of a composition (e.g., of the first composition) is outside (generally above) the desired dosage range of the GLP-1 agonist, then the next composition (e.g., the second composition) or a further composition with a greater ratio of the at least one insulin to the at least one GLP-1 agonist is selected for use, in which the amount of the GLP-1 agonist at the desired insulin dose lies within the desired range. The ratios of the first, second, and, where used, at least one further composition of the combination may further be chosen such that the ranges of the insulin dosages which correspond to the desired dosages of the at least one GLP-1 agonist border one another and/or overlap one another. Preferably, the ranges overlap. Overlapping means more particularly that it is possible to select at least two compositions which, at the desired dose of the at least one insulin, each contain an amount of the at least one GLP-1 agonist which lies within the desired dosage range.

For example, 3 compositions are sufficient to adjust the dose of the at least one insulin for an individual patient to a level selected from the range from 15 to 80 units of insulin and at the same time to dose the GLP-1 agonist with an amount within the range from 10 to 20 µg (see FIG. 4).

It is also possible to provide a combination according to the present invention in which the ratio is selected such that for each desired dosage of the GLP-1 agonist there is a corresponding dosage of the at least one insulin which lies within the desired range. The ratios of the first, second, and, where used, at least one further composition of the pharmaceutical may also be chosen such that the ranges of the dosages of the GLP-1 agonist that correspond to the desired dosages of the at least one insulin border one another and/or overlap one another. Preferably, the ranges overlap. Overlapping in this context means more particularly that it is possible to select at least two compositions which, at the desired dosage of the at least one GLP-1 agonist, each contain an amount of the at least one insulin that lies within the desired dosage range.

Preferably, the combination according to the present invention contains not more than 10 pharmaceutical compositions as defined above, more preferably not more than 5, not more than 4, not more than 3 or 2 pharmaceutical compositions.

The compositions according to the present invention may contain the at least one GLP-1 agonist in, in each case, identical or different weight fractions. For example, at least two of the compositions according to the present invention may contain the at least one GLP-1 agonist in a substantially identical weight fraction.

It is preferred for the first, second, and, where used, further composition(s) to contain the at least one GLP-1 agonist in a substantially identical weight fraction and the at least one insulin in different weight fractions.

The compositions according to the present invention may, however, also contain the at least one insulin in, in each case, identical or different weight fractions. For example, at least two of the compositions according to the present invention may contain the at least one insulin in a substantially identical weight fraction.

It is especially preferred for the first, second, and, where used, further composition(s) to contain the at least one insulin in a substantially identical weight fraction and the at least one GLP-1 agonist in different weight fractions.

A first preferred composition according to the present invention comprises:

| | |
|---|---|
| (a) AVE0010 | approximately 0.025 mg |
| (b) insulin glargine | approximately 3.64 mg |
| (c) zinc chloride | approximately 0.06 mg |
| (d) 85% glycerol | approximately 20.0 mg |
| (e) m-cresol | approximately 2.7 mg |
| (f) L-methionine | approximately 3.0 mg |
| (g) NaOH | q.s. pH 4.5 |
| (h) HCl, 36% | q.s. pH 4.5 |
| (i) water | ad 1 mL |

A second preferred composition according to the present invention comprises:

| | |
|---|---|
| (a) AVE0010 | approximately 0.04 mg |
| (b) insulin glargine | approximately 3.64 mg |
| (c) zinc chloride | approximately 0.06 mg |
| (d) 85% glycerol | approximately 20.0 mg |
| (e) m-cresol | approximately 2.7 mg |
| (f) L-methionine | approximately 3.0 mg |
| (g) NaOH | q.s. pH 4.5 |
| (h) HCl, 36% | q.s. pH 4.5 |
| (i) water | ad 1 mL |

A third preferred composition according to the present invention comprises:

| | |
|---|---|
| (a) AVE0010 | approximately 0.066 mg |
| (b) insulin glargine | approximately 3.64 mg |
| (c) zinc chloride | approximately 0.06 mg |

-continued

|   |   |
|---|---|
| (d) 85% glycerol | approximately 20.0 mg |
| (e) m-cresol | approximately 2.7 mg |
| (f) L-methionine | approximately 3.0 mg |
| (g) NaOH | q.s. pH 4.5 |
| (h) HCl, 36% | q.s. pH 4.5 |
| (i) water | ad 1 mL |

A fourth preferred composition according to the present invention comprises:

|   |   |
|---|---|
| (a) AVE0010 | approximately 0.1 mg |
| (b) insulin glargine | approximately 3.64 mg |
| (c) zinc chloride | approximately 0.06 mg |
| (d) 85% glycerol | approximately 20.0 mg |
| (e) m-cresol | approximately 2.7 mg |
| (f) L-methionine | approximately 3.0 mg |
| (g) NaOH | q.s. pH 4.5 |
| (h) HCl, 36% | q.s. pH 4.5 |
| (i) water | ad 1 mL |

Especially preferred is a combination comprising at least 2, 3, or 4 of the first, second, third, and fourth preferred composition mentioned.

In the present application, "approximately" means that the constituents can be present, for example, within the ranges of ±10, ±20, or ±30 around the specified values in the compositions according to the present invention or/and the combinations; preference is give to ±10.

When the composition according to the present invention or the combination comprises more than one insulin, these insulins are selected independently of one another.

When the composition according to the present invention or the combination comprises more than one GLP-1 agonist, these GLP-1 agonists are selected independently of one another.

The combination according to the present invention is provided more particularly as a pharmaceutical.

The present invention additionally provides a kit comprising a combination according to the present invention comprising at least one, not more than four, composition(s) according to the present invention and also, optionally, Lantus®. The kit according to the present invention may be intended for use by medical staff or by persons without specialist medical training, more particularly by the patients themselves or helpers such as relatives. In the kit according to the present invention, the individual pharmaceutical compositions comprising the combination according to the present invention are assembled in separate packs, and so the patient is able to select the composition appropriate to the current requirement and to administer an amount in line with that requirement. The kit according to the present invention comprises, for example, the combination according to the present invention in the form of a set of syringes, glass ampoules, and/or pens which contain at least one of the compositions according to the present invention, optionally in combination with the composition of Lantus®.

Suitable packaging is a syringe or a glass vessel with a suitable closure, from which individual therapeutically effective doses can be withdrawn as needed. Equally suitable are injection pens for administering insulin; such pens comprise a container (e.g. a cartridge) which contains a pharmaceutical composition according to the present invention.

More particularly, the kit according to the present invention is an injection pen consisting of two separate containers from which, in each case, individual therapeutic doses can be withdrawn as needed. Equally, the kit is a syringe consisting of two containers in which the second container is equipped as a reservoir needle.

In the present invention, the kit preferably consists of a combination of a first formulation, which comprises the GLP-1 agonist, an insulin, glycerol, zinc chloride, optionally m-cresol, L-methionine at a pH of 4.5 in water, and a second formulation, which preferably comprises an insulin, glycerol, zinc chloride, and m-cresol at a pH of 4.5 in water.

The first formulation may preferably have the following composition:

|   |   |   |
|---|---|---|
| (a) AVE0010 | approximately 0.4 mg | or approximately 0.8 mg |
| (b) insulin glargine | approximately 3.64 mg | |
| (c) zinc chloride | approximately 0.06 mg | |
| (d) 85% glycerol | approximately 20.0 mg | |
| (e) m-cresol | 0.0 mg | or approximately 2.7 mg |
| (f) L-methionine | approximately 3.0 mg | |
| (g) NaOH | q.s. pH 4.5 | |
| (h) HCl, 36% | q.s. pH 4.5 | |
| (i) water | ad 1 ml. | |

The second formulation may preferably have the following composition:

|   |   |
|---|---|
| (a) insulin glargine | approximately 3.64 mg |
| (b) zinc chloride | approximately 0.06 mg |
| (c) 85% glycerol | approximately 20.0 mg |
| (d) m-cresol | approximately 2.7 mg |
| (e) NaOH | q.s. pH 4.5 |
| (f) HCl, 36% | q.s. pH 4.5 |
| (g) water | ad 1 ml. |

The present invention further provides for a method for treating a patient with a composition according to the present invention, comprising administering the composition to the patient.

The present invention yet further provides a method for treating a patient with a combination according to the present invention or with a kit as described herein. More particularly, this method comprises the administration of a combination according to the present invention comprising a first pharmaceutical composition and a second pharmaceutical composition, and, optionally, at least one further pharmaceutical composition, each comprising at least one insulin and at least one GLP-1 agonist, and comprising the at least one insulin and/or the at least one GLP-1 agonist in different weight fractions relative to the total weight of the composition, said method comprising:
- (a) selecting a dose of the at least one insulin that is to be administered,
- (b) selecting a dose of the at least one GLP-1 agonist that is to be administered,
- (c) selecting a composition from the first, second, and, where used, at least one further composition of the pharmaceutical that comprises the doses from (a) and (b) in a concentration such that the doses from (a) and (b) are present in the same volume, and
- (d) determining and administering an amount which corresponds to the doses from (a) and (b).

The dose according to step (a) and/or step (b) is determined according to the individual requirement of the patients.

Step (c) of the treatment method according to the present invention can be carried out by referring to a table. This table may be part of the combination according to the present invention, of the pharmaceutical according to the present invention, or of the kit according to the present invention. Example 2 contains an example of a table according to the present invention.

The composition according to the present invention, the combination according to the present invention, the pharmaceutical according to the present invention, or/and the kit according to the present invention is/are intended more particularly for treating diabetes mellitus, more particularly for treating type I or type II diabetes mellitus. Further possible indications are symptoms which are associated with diabetes mellitus. Preferably, the composition according to the present invention is used to control the fasting, post-prandial, or/and postabsorptive plasma glucose concentration, to improve glucose tolerance, to prevent hypoglycemia, to prevent functional loss of the β-cells of the pancreas, to effect weight loss, or/and to prevent weight gain.

The present invention further provides for the use of a composition according to the present invention, a combination according to the present invention, or a kit according to the present invention in the manufacture of a pharmaceutical for treating diabetes mellitus, more particularly type I or type II, or/and the symptoms associated with it, as described herein.

The present invention further provides a method for manufacturing a composition according to the present invention, a combination according to the present invention, or/and a kit according to the present invention, comprising formulating a GLP-1 agonist or/and a pharmacologically tolerable salt thereof with an insulin or/and a pharmaceutically acceptable salt thereof, methionine, and, optionally, at least one pharmaceutically acceptable excipient.

The present invention further provides a method for manufacturing a composition according to the present invention, comprising formulating a GLP-1 agonist or/and a pharmacologically tolerable salt thereof with methionine and, optionally, at least one pharmaceutically acceptable excipient.

The present invention further provides for the use of the compositions according to the invention together with the administration of metformin, insulin glargine, or AVE0010, more particularly in an add-on therapy for administering metformin, insulin glargine, or AVE0010.

More particularly, the composition comprises des Pro$^{36}$ exendin-4(1-39)-Lys$_6$-NH$_2$ (AVE0010) and/or a pharmacologically tolerable salt thereof, insulin glargine and/or a pharmacologically tolerable salt thereof.

Especially preferred is the add-on therapy of the preferred composition in type II diabetes patients who cannot be sufficiently controlled with insulin glargine and/or AVE0010. Also contemplated are patients who are younger than 50 years and/or have a body mass index of at least 30.

In the present invention, the add-on therapy involves more particularly the treatment of type II diabetes with the composition according to the present invention as a supplement to metformin, AVE0010, and/or insulin glargine. The composition according to the present invention can be added in a time interval of 24 hours (once-a-day dosage). Metformin, insulin glargine, and AVE0010 can be administered by means of different routes of administration. Metformin can be administered orally, AVE0010 and insulin glargine, in each case, subcutaneously.

Patients treated with the add-on therapy according to the present invention can have an HbA1c value in the range of 7% to 10%. They are preferably in the age range of 18 to 50 years.

The use in the add-on therapy according to the present invention is more particularly applicable to patients in whom type II diabetes cannot be sufficiently controlled with metformin, AVE0010, or insulin glargine alone. The therapy is preferred in the case of insufficient control through insulin glargine or AVE0010.

The present invention further provides for the use of the composition according to the present invention as a supplement to a diet in order to control the blood sugar level in type II diabetes patients when the application of insulin glargine and AVE0010 is indicated.

More particularly, metformin is administered as follows: at least 1.0 g/day, preferably at least 1.5 g/day for 3 months.

The invention is further elucidated by the following figures and examples.

The frames show the values of the AVE0010 reference formulations at 25° C. and at 40° C.

Figure 3:
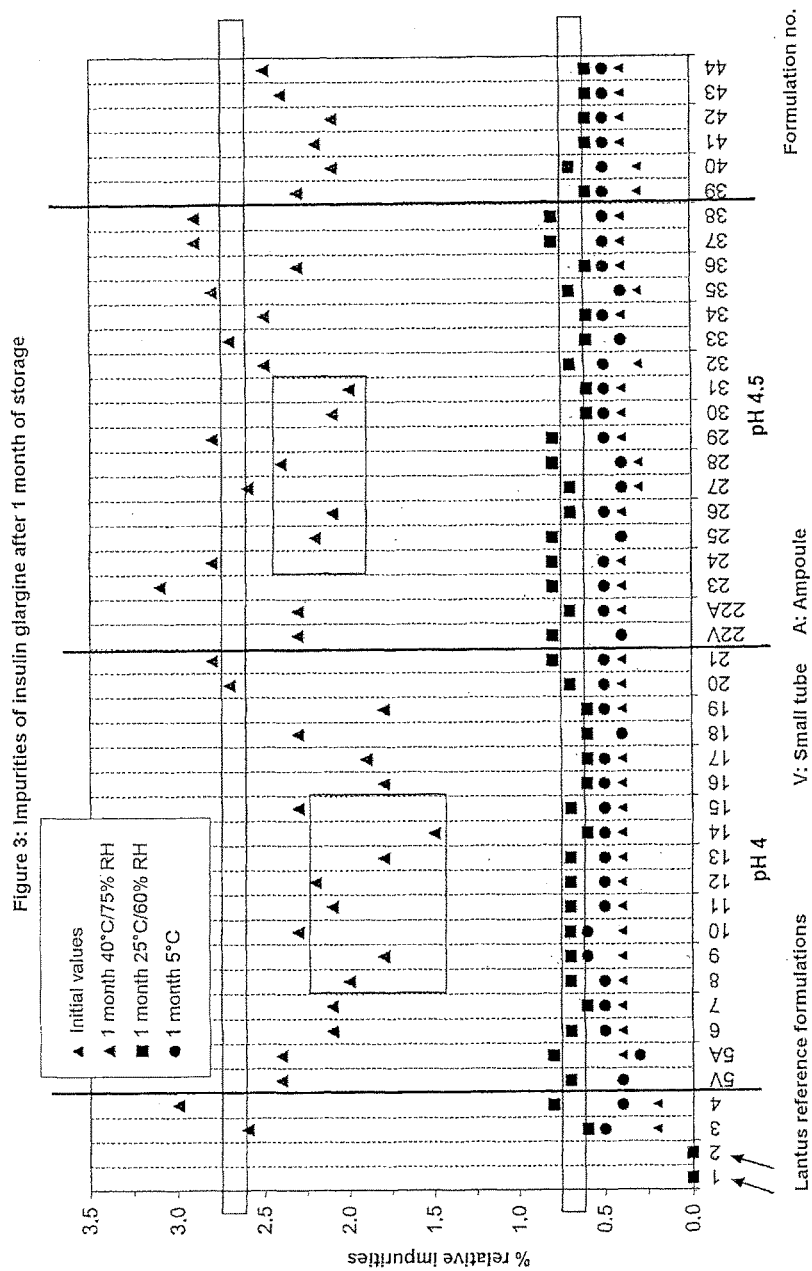

FIG. 3 shows the content of impurities of insulin glargine after 1 month of storage at different temperatures relative to the start of storage. The narrow frames show the values of the insulin glargine reference formulations at 25° C. and at 40° C. The broad frames indicate the formulations having the lowest fractions of AVE0010 impurities.

Figure 4:
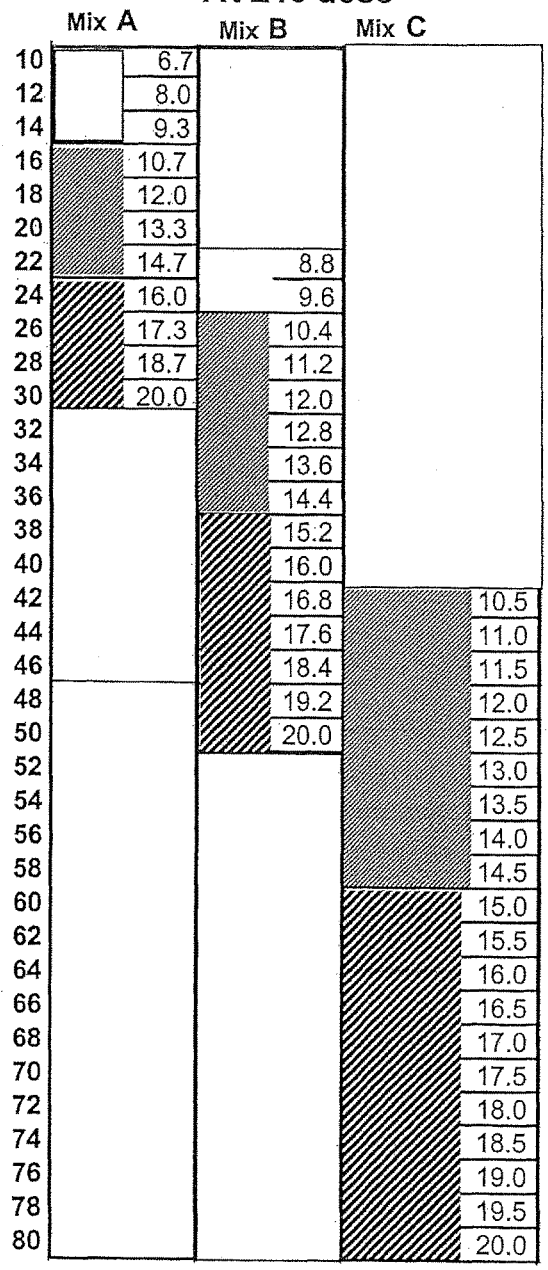

FIG. 4: the "3 pens cover all" concept.

EXAMPLE 1

1. Purpose of Study
The physical and chemical stability of compositions comprising a GLP-1 agonist (AVE0010) and an insulin (insulin glargine, Lantus) was tested.
2. Formulations Used
For the formulations tested, the substances were used in the following concentrations/amounts:

| Substance | Pharmacopeia | Manufacturer | Designation | Amount used [mg/mL] |
|---|---|---|---|---|
| Insulin glargine | | Sanofi-Aventis | | 3.63 |
| | | | | 7.27 |
| | | | | 10.67 |
| AVE0010 | | Poly Peptide LabTorrance CA, USA | | 0.1 |
| | | | | 0.025 |
| Methionine | USP | MP Biomedicals | | 3 |
| Zinc chloride | Ph. Eur., USP, BP | Merck | | 0.03 |
| | | | | 0.06 |
| | | | | 0.09 |

-continued

| Substance | Pharmacopeia | Manufacturer | Designation | Amount used [mg/mL] |
|---|---|---|---|---|
| Glycerol, 85% | Ph. Eur., JP | Hedinger, Stuttgart | | 20 |
| | | | | 18 |
| m-Cresol | Ph. Eur., USP | Hedinger, Stuttgart | | 2.7 |
| Polysorbate 20 | Ph. Eur., JP | Kolb | Tween 20 | 0.02 |
| Polysorbate 80 | Ph. Eur. | SEPPIC | Tween 80 | 0.02 |
| Poloxamer 188 | | BASF, Ludwigshafen | Lutrol F68 | 0.02 |
| Benzalkonium chloride | Ph. Eur., JP | Sigma-Aldrich | | 0.02 |
| L-Lysine | | Resum, F-Ham, Degussa | | 1.0 |
| | | | | 5.0 |
| Acetate | | | | 1.75 |
| | | | | 3.5 |
| NaOH | Ph. Eur., JP | Merck | | 0.1N, for adjusting to pH 4.0 or 4.5 |
| HCl | Ph. Eur., JP | Merck | | 0.1N, for adjusting to pH 4.0 or 4.5 |
| WfI | | | | Ad 1 mL |

When a factor is mentioned in conjunction with a constituent of a formulation (e.g., 1/2, 1/4, 2×, 3×, 5×, as in 1/2 acetate, 5× lysine, 2× Lantus, and 3× Lantus), the concentrations of the substance concerned were used at a reduced or increased concentration depending on the factor.

3. Test Method
3.1 Physical Stability
3.1.1 THT Test

Thioflavin T (THT) binds specifically to protein fibrils, which leads to a change in THT fluorescence. THT does not bind to AVE0010 or insulin. The kinetics of fibril formation can be measured in the presence of THT as the change in fluorescence. An increase in fluorescence corresponds to fibril formation. The shape of the curves allows conclusions about the tendency of a formulation to form fibrils.

Fluorescence measurements were carried out on a Tecan Infinite 200 fluorescence measurement instrument. For analysis of fibrillation kinetics, a Photomed FluoDia 770 high-temperature fluorescence microplate reader was used. The thioflavin T fluorescence spectra were carried out with a Tecan Infinite 200 fluorescence measurement instrument at 23° C. Insulin (900 µl) was mixed with 10 µl of thioflavin T (1 mM in H$_2$O). The mixture was then distributed into a black V-shaped 96-well plate from Biozym (100 µl per well). The emission of fluorescence was measured between 470 and 600 nm (in increments of 1 nm) after excitation at 450 nm with a gain of 100, an integration time of 200 µs, and 25 readings at room temperature.

The binding kinetics of thioflavin T were measured on a Photomed FluoDia 770 high-temperature fluorescence microplate reader. The instrument consists essentially of a 50 W quartz halogen lamp for excitation, filter wheels for excitation and emission which can each contain up to 4 filter sets, and a PMT detector. The heating plate for 96-well plates allows very high precision with regard to temperature (better than ±0.3° C.).

A solution (10 µl) of thioflavin T (10.1 mM in ultrapure water) was added to 1 ml of the formulations and gently mixed by inverting the small tubes several times. The mixture was then distributed into a black V-shaped 96-well plate from Biozym (100 µl per well, 8 wells per sample). All measurements were carried out with the following parameters:
Number of cycles: 181
Excitation filter: 450 nm
Interval: 1 min
Emission filter: 486 nm
Integration time: 20 ms
Temperature control: Standard temperature-control mode
Number of averagings: 4
Target temperature: 70° C.
Attenuation: 4

Fluorescence mean values were determined from 8 parallel measurements.

3.2 Chemical Stability

The formulations were tested for chemical stability after preparation (t0) or after storage for 1 month at 4° C., 25° C. (60% relative humidity), and 40° C. (75% relative humidity). The measurements were carried out on an HPLC instrument (model: alliance) from Water Systems, using the 100% peak area method. For separation, a gradient of 0.1% TFA and acetonitrile as the mobile phase and a C18 reversed-phase column (Jupiter) as the stationary phase were used. For analysis, the formulation was treated with a zinc acetate solution, which led to precipitation of insulin glargirie. The precipitates were centrifuged down, and only the supernatant was analyzed.

Impurities of insulin glargine: the amount of impurities was determined with an HPLC (Water Systems), using the 100% peak area method. For separation, a sodium phosphate-buffered solution (pH 2.5) with NaCl and acetonitrile gradients was used as the mobile phase. A C18 reversed-phase column (Supersher) was used as the stationary phase.

4. Summary of Experimental Data on Physical Stability

| Formulation | | | | THT 3 h, 70° C. relative fluorescence intensity |
|---|---|---|---|---|
| No. | Batch | Composition | pH | at 486 nm |
| 1 | 630 | AVE0010 standard, industrial scale | 4.5 | 536 |
| 2 | 567 | AVE0010 standard, fresh | 4 | 518 |
| 3 | 631 | Lantus standard, industrial scale | 4.0 | 2952 |
| 4 | 560 | Lantus standard, fresh | 4 | 1566 |
| 5 | 568 | Lantus form., AVE0010 | 4 | 2037 |
| 6 | 569 | Lantus form., AVE0010, ½ acetate buffer | 4 | 11763 |

-continued

| Formulation No. | Batch | Composition | pH | THT 3 h, 70° C. relative fluorescence intensity at 486 nm |
|---|---|---|---|---|
| 7 | 570 | Lantus form., AVE0010, acetate buffer | 4 | 69184 |
| 8 | 582 | Lantus form., AVE0010, methionine | 4 | 2053 |
| 9 | 583 | Lantus form., AVE0010, ½ acetate buffer, methionine | 4 | 18814 |
| 10 | 584 | Lantus form., AVE0010, polysorbate 20 | 4 | 8183 |
| 11 | 585 | Lantus form., AVE0010, polysorbate 20, methionine | 4 | 6731 |
| 12 | 586 | Lantus form., AVE0010, polysorbate 20, ½ acetate buffer | 4 | 13897 |
| 13 | 587 | Lantus form., AVE0010, polysorbate 20, ½ acetate buffer, methionine | 4 | 22200 |
| 14 | 588 | Lantus form., AVE0010, polysorbate 20, acetate buffer, methionine | 4 | 134093 |
| 15 | 590 | Lantus form., AVE0010, lysine | 4 | 3362 |
| 16 | 591 | Lantus form., AVE0010, lysine, ½ acetate buffer | 4 | 19677 |
| 17 | 592 | Lantus form., AVE0010, lysine, ½ acetate buffer, polysorbate 20 | 4 | 30176 |
| 18 | 593 | Lantus form., ¼ AVE0010 | 4 | 3107 |
| 19 | 594 | Lantus form., ¼ AVE0010, 5x lysine | 4 | 74662 |
| 20 | 595 | 2x Lantus AVE0010 | 4 | 4504 |
| 21 | 596 | 3x Lantus AVE0010 | 4 | 30251 |
| 22 | 604 | Lantus form., AVE0010 | 4.5 | 4357 |
| 23 | 605 | Lantus form., AVE0010, ½ acetate buffer | 4.5 | 36338 |
| 24 | 606 | Lantus form., AVE0010, acetate buffer | 4.5 | 72370 |
| 25 | 607 | Lantus form., AVE0010, methionine | 4.5 | 5429 |
| 26 | 608 | Lantus form., AVE0010, ½ acetate buffer, methionine | 4.5 | 34714 |
| 27 | 609 | Lantus form., AVE0010, polysorbate 20 | 4.5 | 1166 |
| 28 | 610 | Lantus form., AVE0010, polysorbate 20, methionine | 4.5 | 5564 |
| 29 | 611 | Lantus form., AVE0010, polysorbate 20, ½ acetate buffer | 4.5 | 12115 |
| 30 | 612 | Lantus form., AVE0010, polysorbate 20, ½ acetate buffer, methionine | 4.5 | 16397 |
| 31 | 613 | Lantus form., AVE0010, polysorbate 20, acetate buffer, methionine | 4.5 | 779 |
| 32 | 614 | Lantus form., AVE0010, lysine | 4.5 | 9726 |
| 33 | 615 | Lantus form., AVE0010, lysine, ½ acetate buffer | 4.5 | 74027 |
| 34 | 616 | Lantus form., AVE0010, lysine, ½ acetate buffer, polysorbate 20 | 4.5 | 9520 |
| 35 | 617 | Lantus form., ¼ x AVE0010 | 4.5 | 3713 |
| 36 | 618 | Lantus form., ¼ x AVE0010, 5x lysine | 4.5 | 83384 |
| 37 | 619 | 2x Lantus AVE0010 | 4.5 | 13120 |
| 38 | 620 | 3x Lantus AVE0010 | 4.5 | 41684 |
| 39 | 657 | Lantus form., AVE0010, polysorbate 80, methionine | 4 | 9309 |
| 40 | 658 | Lantus form., AVE0010, poloxamer 188, methionine | 4 | 767 |
| 41 | 659 | Lantus form., AVE0010, benzalkonium chloride, methionine | 4 | 1040 |
| 42 | 660 | Lantus form., AVE0010, polysorbate 80, methionine | 4.5 | 16803 |
| 43 | 661 | Lantus form., AVE0010, poloxamer 188, methionine | 4.5 | 689 |
| 44 | 662 | Lantus form., AVE0010, benzalkonium chloride, methionine | 4.5 | 942 |

5. THT Test

Methionine has no influence on the tendency to form fibrils. The formulations

| No. | Composition | Fluorescence intensity at 486 nm |
|---|---|---|
| 2 | AVE0010 standard | 518 |
| 4 | Lantus standard | 1566 |
| 8 | Lantus form., AVE0010, methionine, pH 4 | 2053 |
| 25 | Lantus form., AVE0010, methionine, pH 4.5 | 5429 | have fluorescence values like the reference formulations (no. 2 and 4). With values below approximately 6000, no tendency to form fibrils is present.

When AVE0010, Lantus, and methionine are combined with acetate buffer with or without polysorbate 20 at pH 4, there is a greater tendency to form fibrils:

| No. | Composition | Fluorescence intensity at 486 nm |
|---|---|---|
| 2 | AVE0010 standard | 518 |
| 4 | Lantus standard | 1566 |
| 9 | Lantus form., AVE0010, ½ acetate, Met, pH 4 | 18814 |
| 13 | Lantus form., AVE0010, polysorbate 20, ½ acetate, Met, pH 4 | 22200 |
| 14 | Lantus form., AVE0010, polysorbate 20, acetate, Met, pH 4 | 134093 |

The values for formulations 13 and 14 lie clearly above the threshold for a tendency to form fibrils.

6.1 Summary

Polysorbate 20 and polysorbate 80 can lead to turbidity, which is detectable in the double refraction test. Hence, both of these substances can lead to physical instability of a formulation of AVE0010 and insulin.

The addition of methionine does not lead to physical instability.

7. Chemical Stability 7.1 Stability at Time Point t0

The formulations which comprise methionine (with and without sodium acetate) have the lowest amounts of impurities (overall, approximately 1.2 to 1.5%). The following formulations have low amounts of impurities:

8 Lantus form., AVE0010, methionine, pH 4
9 Lantus form., AVE0010, 1/2 acetate buffer, methionine, pH 4
11 Lantus form., AVE0010, polysorbate 20, methionine, pH 4
13 Lantus form., AVE0010, 1/2 acetate buffer, polysorbate 20, methionine, pH 4
14 Lantus form., AVE0010, acetate buffer, polysorbate 20, methionine, pH 4
25 Lantus form., AVE0010, methionine, pH 4.5
26 Lantus form., AVE0010, 1/2 acetate buffer, methionine, pH 4.5
28 Lantus form., AVE0010, polysorbate 20, methionine, pH 4.5
30 Lantus form., AVE0010, 1/2 acetate buffer, polysorbate 20, methionine, pH 4.5
31 Lantus form., AVE0010, acetate buffer, polysorbate 20, methionine, pH 4.5

Formulations which did not comprise methionine showed a higher fraction of impurities.

Polysorbate 20 has no negative influence on the chemical stability of the formulations.

Acetate buffer has no negative influence on chemical stability when it is combined with methionine and polysorbate 20.

When lysine is present in the formulations, the sum of impurities is greater. The same is true for formulations which comprise polysorbate 80, poloxamer 188, and benzalkonium chloride.

Determining the impurities of insulin glargine revealed that all formulations had comparable amounts of impurities (0.3 to 0.4%).

7.2 Stability after 1 Month 7.2.1 Impurities of AVE0010

The content of oxidized methionine in the formulations was analyzed. The sequence of AVE0010 has one methionine residue at position 14. The sequence of insulin glargine has no methionine residues. Therefore, the content of oxidized methionine is indicative of oxidation of AVE0010 at the methionine residue. The data are summarized in FIG. 1. Overall, the data show that, without methionine at a pH of 4.5, the fraction of Met(ox) is higher than at pH 4.0. Without methionine as a constituent of the formulations, the fractions of Met(ox) are greatest when the content of insulin glargine is increased or the content of AVE0010 is reduced.

Generally, the greatest fractions of Met(ox) were measured after storage at 40° C./75% relative humidity. Here, the lowest fractions of Met(ox)-AVE0010 (<1%) are to be found in the formulations 8, 9, 11, 13, 14, 25, 26, 28, 30, and 31. The values of these formulations are in the range of the values for the AVE0010 reference formulations no. 1 and 2 (frame in FIG. 1).

Figure 2:
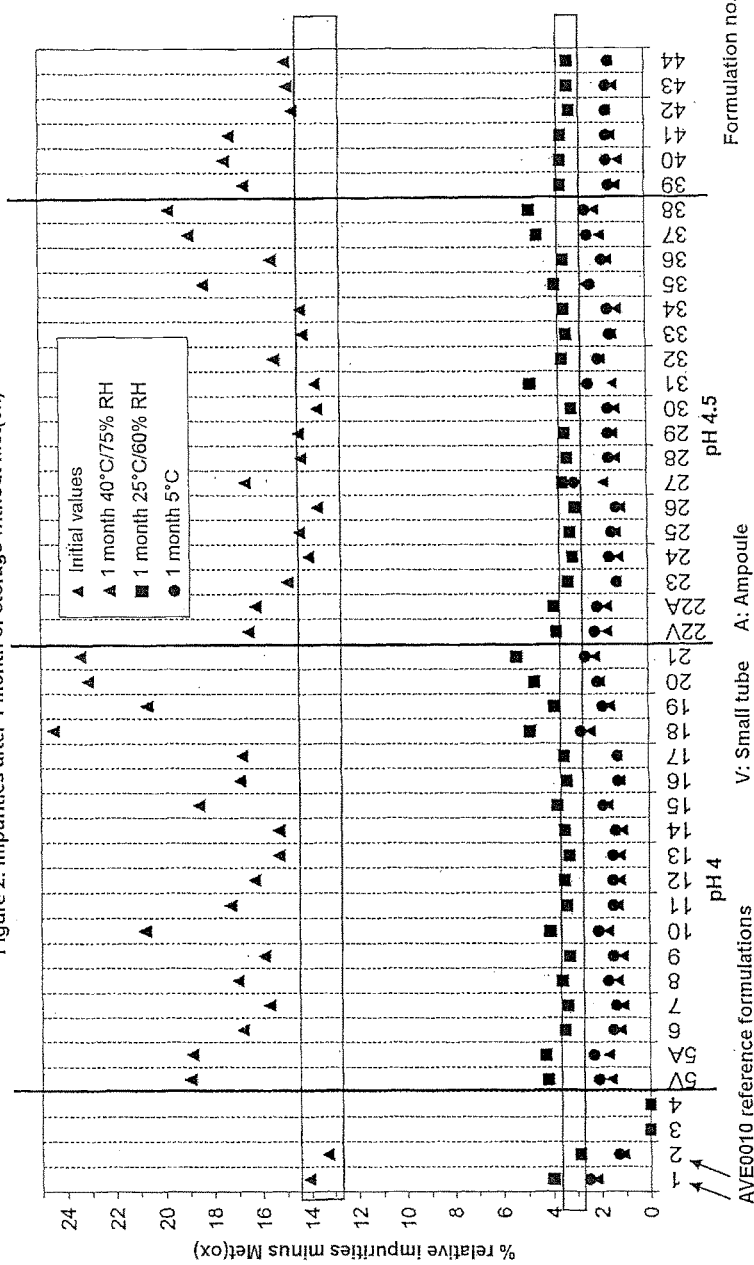
FIG. 2 shows the content of impurities of AVE0010 without Met(ox) after 1 month of storage at different temperatures relative to the start of storage.

The impurities of AVE0010 after 1 month without Met(ox) are represented in FIG. 2. The frames show the values of the AVE0010 reference formulations at 25° C. and at 40° C. Formulations which have the same or better impurity values than the AVE0010 reference formulations are within or below the frames. This is true for the formulations 24, 25, 26, 28, 29, 30, 31, 33, and 34 (40° C.). Impurity values which are above the impurity values of the AVE0010 reference formulations indicate impurities of insulin glargine. Generally, formulations having a pH of 4.5 have fewer impurities than at a pH of 4.0.

Figure 1:
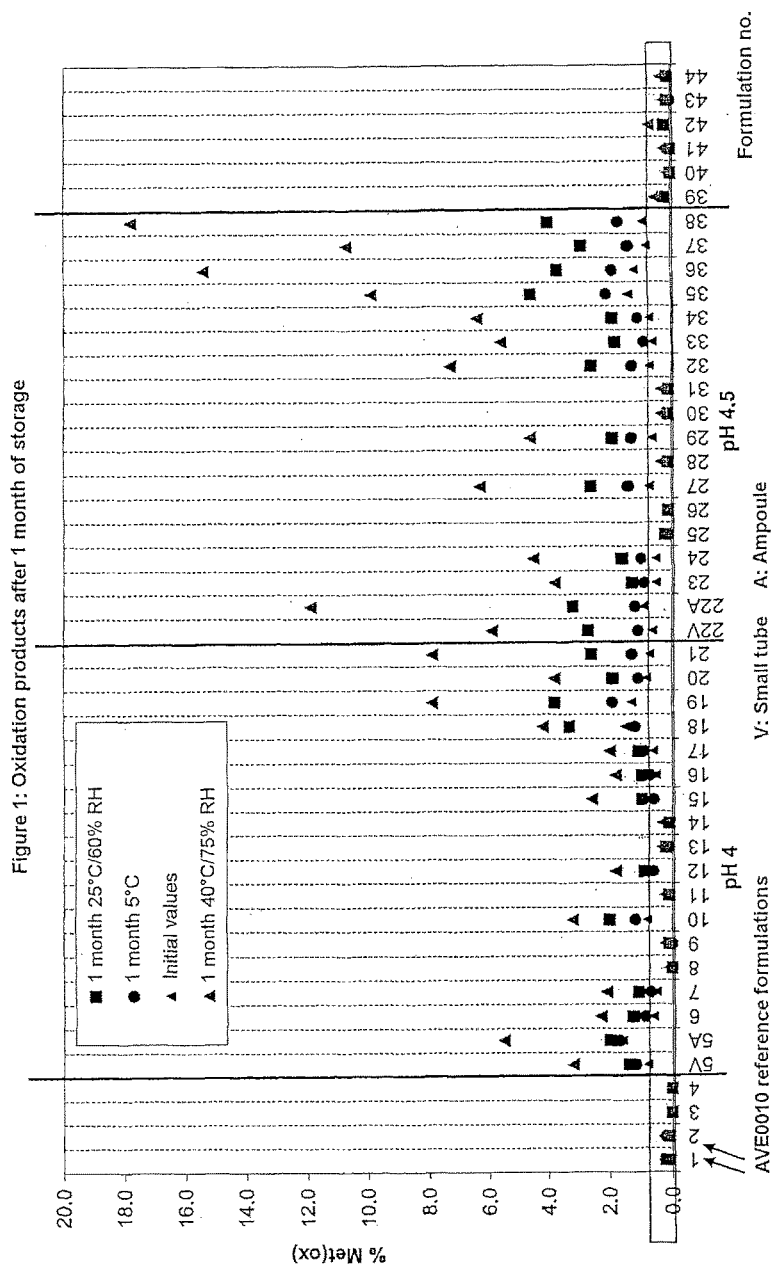
FIG. 1 shows the content of oxidized methionine Met(ox) in AVE0010 after 1 month of storage at different temperatures relative to the start of storage. The frame shows the values for the AVE0010 reference formulation no. 1 and 2.

The following formulations have, after storage for one month at 40° C., the lowest content of Met(ox) and, simultaneously, the lowest content of other impurities (comparison of FIGS. 1 and 2). They are better than or the same as the AVE0010 reference formulations:

25 Lantus form., AVE0010, methionine, pH 4.5
26 Lantus form., AVE0010, 1/2 acetate buffer, methionine, pH 4.5
28 Lantus form., AVE0010, polysorbate 20, methionine, pH 4.5
30 Lantus form., AVE0010, 1/2 acetate buffer, polysorbate 20, methionine, pH 4.5

These formulations also belonged to those formulations which have at time point t0 the lowest amounts of AVE0010 impurities. All formulations comprise methionine. Polysorbate 20 has no negative effects on the impurities.

The impurities of insulin glargine are represented in FIG. 3. Formulations 3 and 4 are the reference formulations for insulin glargine. The values of these formulations are indicated as narrow frames. All formulations which were identified with regard to AVE0010 impurities as the best formulations (broad frames, more particularly formulations 25, 26, 28, and 30) are, with regard to insulin glargine impurities, better than the insulin glargine reference formulations (approximately 1.5 to 2.4% at 40° C.).

Hence, it can be deduced from this experiment that methionine engenders an increased storage stability of a composition comprising an insulin (e.g., Lantus) and a GLP-1 agonist AVE0010). The addition of methionine engenders chemical integrity of this composition.

8. Conclusions

The data described herein lead to the following conclusions:

Methionine leads to an increased chemical stability and has no negative effects on the physical stability of formulations of a combination of a GLP-1 agonist, more particularly AVE0010, and an insulin, more particularly Lantus. Therefore, methionine is advantageous as a constituent of these compositions.

Acetate can lead to physical instability. This instability is greater with increasing acetate concentration. Therefore, formulations of a combination of a GLP-1 agonist, more particularly AVE0010, and an insulin, more particularly Lantus, which are free of acetate are advantageous compared with corresponding compositions which comprise acetate.

Polysorbate 20 has no negative influence on the physical and the chemical stability of formulations of a combination of a GLP-1 agonist, more particularly AVE0010, and an insulin, more particularly Lantus. By combining acetate at lower concentrations (1/2 acetate) with polysorbate 20, the negative effects of acetate can be partially compensated. In acetate-free compositions, the addition of polysorbate 20 does not lead to any advantages. Therefore, formulations of a combination of a GLP-1 agonist, more particularly AVE0010, and an insulin, more particularly Lantus, should be prepared which are free of polysorbate 20.

Lysine (at normal and higher concentrations), benzalkonium chloride, polysorbate 80, and poloxamer 188 already showed chemical instability at the beginning of the studies (t0). For lysine, this is also true for the results of the THT test.

EXAMPLE 2

The "3 pens cover all" concept (FIG. 4)
3 premix pens having 3 different predetermined proportions:
 (a) Mix A: 100 U Lantus+66.66 μg AVE0010 per mL
 (b) Mix B: 100 U Lantus+40 μg AVE0010 per mL
 (c) Mix C: 100 U Lantus+25 μg AVE0010 per mL
Use of the 3 premix pens: The exemplary table in FIG. 4 proceeds from a therapeutic range of 15 to 80 Upper dose of Lantus and 10 to 20 μg AVE0010. For a particular patient, a dose of Lantus to be administered is set or predetermined. The predetermined dose is looked up in the left-hand column. When a corresponding AVE0010 dose in the range from 10 to 20 μg is mentioned in the columns MIX A-MIX C, the corresponding MIX is selected, metered, and administered. The ranges are overlapping: for example, when 26 to 30 U Lantus is required, Mix A or MIX B (having a higher dose of AVE0010) could be selected. Accordingly, this is true for MIX B and C. If, for example, a dose of 50 U of insulin is determined, then 0.5 ml of MIX B or MIX C is to be metered. This dose contains 20 μg (MIX B) or 12.5 μg (MIX C) of AVE0010.
Conclusion: Assuming that a probable AVE0010 effect in the range from 10 to 15 μg and a therapeutic effect in the range from 15 to 22 μg is achieved, almost all patients who take Lantus doses of 15-80 U can likewise receive therapeutic doses of AVE0010 in the range from 10 to 20 μg when they use one of the three premix pens, which contain three different Lantus:AVE0010 ratios (Mix A, B, or C). Due to the broad range of possible ratios of Lantus to AVE0010, the ratios in the pens can be fine-tuned such that a desired dose of AVE0010 is included for every dose of Lantus in at least one pen.

The invention claimed is:

1. An aqueous liquid composition comprising the following constituents per 1 ml of the composition:
 (a) about 0.025 mg to about 0.1 mg desPro$^{36}$exendin-4 (1-39)-Lys$_6$-NH2 or a pharmacologically tolerable salt thereof;
 (b) about 3.64 mg insulin glargine or a pharmacologically tolerable salt thereof;
 (c) about 3.0 mg methionine
 (d) water is present in a quantity sufficient for the volume of the composition to total about 1 mL;
 (e) about 2.7 mg m-cresol;
 (f) about 20.0 mg 85% glycerol; and
 (g) about 0.06 mg zinc chloride,
wherein the composition has a pH in the range from 3.5 to 4.5, and wherein the composition comprises no buffer substances.

2. The aqueous liquid composition of claim 1, wherein the composition exhibits chemical integrity after storage for 6 months at a temperature of +25° C.

3. The aqueous liquid composition of claim 1, wherein the composition exhibits physical integrity after storage for 6 months at a temperature of +25° C.

4. The aqueous composition of claim 1, wherein the composition is suitable for parenteral an injectable composition.

5. The aqueous liquid composition of claim 1, wherein at least 80% of the composition's active ingredients are in a substantially chemically unchanged form after storage for 6 months at a temperature of +25° C.

6. The aqueous liquid composition of claim 1, wherein at least 80% of the composition's active ingredients are in a substantially physically unchanged form after storage for 6 months at a temperature of +25° C.

7. The aqueous liquid composition of claim 1, wherein the composition has a pH of 4.5.

8. The aqueous liquid composition of claim 1, wherein the composition comprises an oxidized content if about 1% or less after 1 month of storage.

9. The aqueous liquid composition of claim 1, wherein the composition is pharmacologically tolerable.

* * * * *